(12) United States Patent
Takahashi et al.

(10) Patent No.: US 12,351,601 B2
(45) Date of Patent: Jul. 8, 2025

(54) METHOD FOR PRODUCING PEPTIDE CONTINUOUSLY

(71) Applicant: AJINOMOTO CO., INC., Tokyo (JP)

(72) Inventors: Daisuke Takahashi, Kawasaki (JP); Metten Bert, Wettern (BE); Kimio Kawajiri, Kawasaki (JP); Ryotaro Nakaya, Wetteren (BE)

(73) Assignee: AJINOMOTO CO., INC., Tokyo (JP)

( * ) Notice: Subject to any disclaimer, the term of this patent is extended or adjusted under 35 U.S.C. 154(b) by 182 days.

(21) Appl. No.: 17/506,934

(22) Filed: Oct. 21, 2021

(65) Prior Publication Data
US 2022/0041648 A1 Feb. 10, 2022

Related U.S. Application Data

(63) Continuation of application No. PCT/JP2020/017670, filed on Apr. 24, 2020.

(30) Foreign Application Priority Data

Apr. 25, 2019 (JP) .................... 2019-084652

(51) Int. Cl.
C07K 1/06 (2006.01)
(52) U.S. Cl.
CPC .................... *C07K 1/062* (2013.01)
(58) Field of Classification Search
CPC .............. C07K 1/06; C07K 1/02; C07K 1/14
See application file for complete search history.

(56) References Cited

U.S. PATENT DOCUMENTS

| | | | |
|---|---|---|---|
| 2007/0066799 A1 | 3/2007 | Chiba et al. | |
| 2009/0299103 A1 | 12/2009 | Chiba et al. | |
| 2010/0029904 A1 | 2/2010 | Chiba et al. | |
| 2010/0240867 A1 | 9/2010 | Takahashi | |
| 2010/0249374 A1 | 9/2010 | Takahashi | |
| 2011/0160433 A1 | 6/2011 | Takahashi | |
| 2012/0059149 A1* | 3/2012 | Takahashi | C07C 217/58 564/321 |
| 2018/0215782 A1 | 8/2018 | Kono et al. | |
| 2019/0023726 A1 | 1/2019 | Yano et al. | |
| 2021/0139532 A1 | 5/2021 | Sljzljkl et al. | |

FOREIGN PATENT DOCUMENTS

| | | |
|---|---|---|
| JP | 2000-44493 A | 2/2000 |
| JP | 2004-35521 A | 2/2004 |
| JP | 2004-59509 A | 2/2004 |
| JP | 2007-186452 A | 7/2007 |
| WO | WO 03/018188 A1 | 3/2003 |
| WO | WO 2006/104166 A1 | 10/2006 |
| WO | WO 2007/034812 A1 | 3/2007 |
| WO | WO 2007/122847 A1 | 11/2007 |
| WO | WO 2010/104169 A1 | 9/2010 |
| WO | WO 2010/113939 A1 | 10/2010 |
| WO | WO 2011/078295 | 6/2011 |
| WO | WO 2011/078295 A1 | 6/2011 |
| WO | WO 2012/029794 A1 | 3/2012 |
| WO | WO 2016/140232 A1 | 9/2016 |
| WO | WO 2017/038650 A1 | 3/2017 |
| WO | WO 2019/009317 A1 | 1/2019 |
| WO | WO 2019/198833 A1 | 10/2019 |

OTHER PUBLICATIONS

International Search Report issued Jul. 21, 2020 in PCT/JP2020/017670, 3 pages.
Shinichiro Fuse et al., "Peptide Synthesis Utilizing Micro-flow Technology", Chemistry, An Asian Journal, 2018, vol. 13, No. 24, pp. 3818-3832.
Joshua Britton et al., "Multi-step continuous-flow synthesis", Chemical Society Reviews, 2017, vol. 46, pp. 1250-1271.
Liquid phase synthesis of peptides, non-official translation (Takumi, Masahiro et al., "Special issue, Nanotechnology supports chemical technology, Microreactor research development status and its perspectives", Kagaku Sochi) , Mar. 1, 2019, vol. 61, No. 3, pp. 17-22 (with partial English translation).
Shinichiro Fuse et al., "Efficient Amide Bond Formation through a Rapid and Strong Activation of Carboxylic Acids in a Microflow Reactor", Angew. Chem. Int. Ed. 2014, 53, pp. 851-855.

(Continued)

*Primary Examiner* — Sudhakar Katakam
(74) *Attorney, Agent, or Firm* — Oblon, McClelland, Maier & Neustadt, L.L.P.

(57) ABSTRACT

Peptides may be continuously produced by a method including the following steps (1), (A), (2), and (B):
(1) performing a condensation reaction in a flow reactor to obtain an N-protected C-protected peptide in which an N-terminal amino group and C-terminal are protected by protecting groups, a side chain functional group is optionally further protected by a protecting group, and at least one of the C-terminal or the side chain functional group is protected by a pseudo-solid-phase protecting group (N-protected C-protected peptide),
(A) washing a reaction mixture containing an N-protected C-protected peptide in a flow reactor and separating oil and water to separate an organic layer containing the N-protected C-protected peptide,
(2) subjecting an organic layer containing an N-protected C-protected peptide to a reaction to remove a protecting group of an N-terminal amino group in a flow reactor to obtain a C-protected peptide in which an N-terminal amino group is not protected, C-terminal is protected by a protecting group, a side chain functional group is optionally further protected by a protecting group, and at least one of the C-terminal or the side chain functional group is protected by a pseudo-solid-phase protecting group (N-unprotected C-protected peptide),
(B) subjecting a reaction mixture containing an N-unprotected C-protected peptide to washing and oil-water separation in a flow reactor to separate an organic layer containing the N-unprotected C-protected peptide.

15 Claims, No Drawings

(56) References Cited

OTHER PUBLICATIONS

Daisuke Takahashi, "Ajiphaser®: :A Highly Efficient Synthetic Method for One-Pot Peptide Elongation in the Solution Phase by an Fmoc Strategy", Angewandte Chemie International Edition, 2017, 56, pp. 7803-7807.

* cited by examiner

METHOD FOR PRODUCING PEPTIDE CONTINUOUSLY

CROSS REFERENCES TO RELATED APPLICATIONS

This application is a continuation of International Patent Application No. PCT/JP2020/017670, filed on Apr. 24, 202, and claims priority to Japanese Patent Application No. 2019-084652, filed on Apr. 25, 2019, both of which are incorporated herein by reference in their entireties.

BACKGROUND OF THE INVENTION

Field of the Invention

The present invention relates to methods for continuously producing peptides, and is useful in the field of peptide synthesis.

Discussion of the Background

Peptide synthesis is divided into a solid phase method and a liquid phase method based on the embodiment of C-protected peptide (C-protected amino acid at the time of dipeptide formation reaction).

In the solid phase method, peptide elongation is performed with the C-terminal of the peptide (or amino acid) bound to a solid support, and the target peptide is separated from the solid support in the final stage. Therefore, reagents and by-products remaining due to excess or non-reaction can be easily eliminated by washing the solid support. For this reason, the solid phase method is used in the industrial production of peptide drugs. However, since the reaction is limited to the surface of the solid support, problems occur in scale-up and reactivity.

In contrast, since the liquid phase method is easy to scale up and has relatively good reactivity, it can be a means for solving the above-mentioned problems in the solid phase method. However, in the liquid phase method, it is necessary to remove residual reagents and by-products each time in respective steps of the condensation reaction and the deprotection reaction, which in turn poses problems of complicated production steps and increase in the time required for production of the final pharmaceutical products. Even on a small scale for research use, the liquid phase method has a problem that the production step is complicated and the production requires time.

To solve the above-mentioned problems of the liquid phase method, use of a production method using a pseudo-solid-phase protecting group (see JP-A-2000-44493, WO 2006/104166, WO 2007/034812, WO 2007/122847, WO 2010/113939, WO 2010/104169, and WO 2011/078295, all of which are incorporated herein by reference in their entireties) that can perform isolation and purification by solid-liquid separation (that is, crystallization) was considered. However, when the isolation and purification method by crystallization is used, it is difficult to continuously produce peptides because the steps are non-continuous.

On the other hand, a production method using a pseudo-solid-phase protecting group, which includes conducting a reaction in a homogeneous liquid phase, and, after changing the solvent composition after the reaction, performing isolation and purification merely by extraction and washing, without requiring an operation for solid-liquid separation has been found (see WO 2012/029794, WO 2016/140232, WO 2003/018188, WO 2017/038650, and WO 2019/009317, all of which are incorporated herein by reference in their entireties). In peptide synthesis, the lipophilicity and the solubility in organic solvents (particularly, non-polar organic solvents) of the peptide of the production intermediate obtained in each step of the peptide elongation reaction are remarkably improved by protecting the C-terminal and/or a side chain functional group of an amino acid or peptide with a pseudo-solid-phase protecting group and purification can be performed only by an extraction washing operation. Therefore, according to this method, complicated and time-consuming operations such as solid-liquid separation and the like are not required, speed is improved, and efficiency and producibility are strikingly improved.

The above-mentioned production method using a pseudo-solid-phase protecting group is a very useful method which shows advantages of both the solid phase reaction and the liquid phase reaction, and draws attention also from an industrial aspect. However, when the purification step is performed by batch processing each time in a non-continuous flow, there remains a problem that purification takes time, and further improvement has been desired.

The peptide synthesis process in the above-mentioned liquid phase method described above is a synthetic process called "batch synthesis" that has been widely performed in the field of organic synthesis. In recent years, study of "flow synthesis" utilizing a flow reactor (particularly, flow microreactor) is also underway in the field of organic synthesis. The "flow synthesis" is said to have advantages such as shortening of synthesis time, ease of scale-up and the like. For example, regarding peptide synthesis, a continuous synthesizer for peptide synthesis utilizing a flow reactor has been proposed, which has an oil-water separation means for separating and removing unreacted aqueous phase components after synthesis (see JP-A-2007-186452, which is incorporated herein by reference in its entirety). In addition, as utilization of a flow reactor in peptide synthesis, studies have been conducted on short chain peptides having not more than 4 amino acid residues; however, the target compounds have been limited (see S. Fuse et al., Angew. Chem. Int. Ed. 2014, 53, 851-855, which is incorporated herein by reference in its entirety).

SUMMARY OF THE INVENTION

A major concern in applying flow synthesis in a flow reactor is a phenomenon called "clogging". If the resultant product is not sufficiently dissolved in a solvent and solids such as crystals are formed, the flow reactor will be clogged and the intended purpose cannot be achieved. Depending on the kind of protecting group during synthesis, sufficient solubility in a solvent cannot always be expected when the desired peptide has a particularly long chain. Thus, there is a growing concern on this point when applied to peptide synthesis.

JP-A-2007-186452, which is incorporated herein by reference in its entirety, discloses a continuous synthesizer for performing peptide synthesis utilizing a flow reactor, which has an oil-water separation means for separating and removing unreacted aqueous phase components after synthesis. However, it does not disclose a case of actual peptide synthesis, and does not clarify the scope of application or peptides with what chain length can be synthesized. As mentioned above, non-patent document 1 is known as an example of peptide synthesis actually using a flow reactor. However, the study was limited to short chain peptides with four or less amino acid residues, and the target compounds were limited.

For the establishment of continuous synthesis, it is essential to remove residual starting materials and residual reagents when used in excess, and reaction contaminants (By-Products) so as not to affect the next reaction. In the case of JP-A-2007-186452, which is incorporated herein by reference in its entirety, and S. Fuse et al., Angew. Chem. Int. Ed. 2014, 53, 851-855, which is incorporated herein by reference in its entirety, removal of the contaminants and the like is also considered to be difficult.

Furthermore, when synthesizing a peptide having a pseudo-solid-phase protecting group, since the resultant product has structural characteristics that have a so-called surfactant action, it is not separated, and therefore it is not clear whether the peptide as a resultant product (particularly when the peptide is elongated and becomes a long chain) can be separated into an organic layer as originally intended by the oil-water separation means disclosed in patent document 13.

The present inventors have found a means for synthesizing a desired peptide by combining, using a peptide protected by a pseudo-solid-phase protecting group, elongation of peptide chain in a flow reactor, washing to remove unreacted products and by-products from the resultant product in a flow reactor in each step, and layer separation by an oil-water separation means (in continuous flow, where necessary) so that solubility in a solvent can be maintained even when the peptide becomes a long chain, and reaction contaminants and the like can be removed easily. They have also surprisingly found that peptides can be synthesized and purified extremely efficiently (continuously in the entire flow of production, where necessary) because, regardless of the chain length of the peptide, the phenomenon of clogging does not occur in the flow reactor, the resultant product does not become micelles like surfactants even though it has a pseudo-solid-phase protecting group, and it is separated into an organic layer even by an oil-water separation means, which resulted in the completion of the present invention. Accordingly, the present invention provides the following.

(1) A method for producing a peptide, comprising the following step (A) and/or step (B):

(A)
a step of washing a reaction mixture comprising an N-protected C-protected peptide in which an N-terminal amino group and C-terminal are protected by protecting groups, a side chain functional group is optionally further protected by a protecting group, and at least one of the C-terminal or the side chain functional group is protected by a pseudo-solid-phase protecting group (N-protected C-protected peptide) in a flow reactor with water and/or a hydrophilic organic solvent in a continuous flow, and then purifying the N-protected C-protected peptide by partitioning in a continuous flow by an oil-water separation means and separating an organic layer containing the N-protected C-protected peptide, (B)
a step of washing a reaction mixture comprising a C-protected peptide in which an N-terminal amino group is not protected, C-terminal is protected by a protecting group, a side chain functional group is optionally further protected by a protecting group, and at least one of the C-terminal or the side chain functional group is protected by a pseudo-solid-phase protecting group (N-unprotected C-protected peptide) in a not protected, C-terminal is protected by a protecting group, a side chain functional group is optionally further protected by a protecting group, and at least one of the C-terminal or the side chain functional group is protected by a pseudo-solid-phase protecting group (N-unprotected C-protected peptide) in a flow reactor with water and/or a hydrophilic organic solvent in a continuous flow, and then purifying the N-unprotected C-protected peptide by partitioning in a continuous flow by an oil-water separation means and separating an organic layer containing the N-unprotected C-protected peptide.

(2) A method for producing a peptide, comprising the following steps (1), (A), (2), and (B):

(1)
a step of introducing a C-protected amino acid in which C-terminal is protected by a protecting group, a side chain functional group is optionally further protected by a protecting group, and at least one of the C-terminal or the side chain functional group is protected by a pseudo-solid-phase protecting group (C-protected amino acid), or a C-protected peptide in which C-terminal is protected by a protecting group, a side chain functional group is optionally further protected by a protecting group, and at least one of the C-terminal or the side chain functional group is protected by a pseudo-solid-phase protecting group (C-protected peptide); N-protected amino acid in which C-terminal is not protected, an N-terminal amino group is protected by a protecting group, and a side chain functional group is optionally further protected by a protecting group (N-protected amino acid), or an N-protected peptide in which C-terminal is not protected, an N-terminal amino group is protected by a protecting group, and a side chain functional group is optionally further protected by a protecting group (N-protected peptide);
a condensing agent; and
a soluble organic solvent
into a flow reactor, performing a condensation reaction in the flow reactor in a continuous flow, and elongating the N-terminal to obtain an N-protected C-protected peptide in which an N-terminal amino group and C-terminal are protected by protecting groups, a side chain functional group is optionally further protected by a protecting group, and at least one of the C-terminal or the side chain functional group is protected by a pseudo-solid-phase protecting group (N-protected C-protected peptide), (A)
a step of washing a reaction mixture comprising an N-protected C-protected peptide in a flow reactor with water and/or a hydrophilic organic solvent in a continuous flow, and then purifying the N-protected C-protected peptide by partitioning in a continuous flow by an oil-water separation means and separating an organic layer containing the N-protected C-protected peptide, (2)
a step of introducing an organic layer comprising an N-protected C-protected peptide into a flow reactor in a continuous flow, and removing a protecting group of an N-terminal amino group in a flow reactor in a continuous flow to obtain a C-protected peptide in which an N-terminal amino group is not protected, C-terminal is protected by a protecting group, a side chain functional group is optionally further protected by a protecting group, and at least one of the C-terminal or the side chain functional group is protected by a pseudo-solid-phase protecting group (N-unprotected C-protected peptide), (B)
a step of washing a reaction mixture comprising an N-unprotected C-protected peptide in a flow reactor with water and/or a hydrophilic organic solvent in a continuous flow, and then purifying the N-unprotected C-protected peptide by partitioning in a continuous flow by an oil-water separation means and separating an organic layer comprising the N-unprotected C-protected peptide.

(3) The production method of the above-mentioned (2), wherein the steps (1), (A), (2), and (B) are performed in this order.

(4) The production method of the above-mentioned (2), wherein the steps (2), (B), (1), and (A) are performed in this order.

(5) The production method of any of the above-mentioned (1) to (4), wherein the reaction mixture forms a slug flow during washing with water and/or a hydrophilic organic solvent in the flow reactor.
(6) The production method of any of the above-mentioned (1) to (5), wherein the oil-water separation means is either a continuous layer separation means with a constitution including a filter, or a Gravity type continuous layer separation means.
(7) The production method of any of the above-mentioned (1) to (6), wherein the protecting group of the amino group is a 9-fluorenylmethyloxycarbonyl group, a tert-butoxycarbonyl group, or a benzyloxycarbonyl group.
(8) The production method of the above-mentioned (7), wherein the protecting group of the amino group is a 9-fluorenylmethyloxycarbonyl group.
(9) The production method of any of the above-mentioned (1) to (8), further comprising a step of obtaining an organic layer containing the N-protected C-protected peptide obtained in the step (A), or the N-unprotected C-protected peptide obtained in the step (B), and then removing all protecting groups.
(10) The production method of any of the above-mentioned (1) to (9), wherein a peptide having an amino acid residue number of not less than 5 and not more than 100 (more preferably, not less than 5 and not more than 50) is produced.
(11) The production method of any of the above-mentioned (1) to (10), wherein the pseudo-solid-phase protecting group is selected from (4',4'-bis(2,3-dihydrophytyloxy) phenyl)methylamine);
3,4,5-tri(2',3'-dihydrophytyloxy)benzyl alcohol;
2-[3,4,5-tri(2',3'-dihydrophytyloxy)benzyloxy]-4-methoxy-benzyl alcohol;
3,4,5-tri(octadecyloxy)cyclohexanemethanol;
[bis-(4-docosoxy-phenyl)-methyl]-amine;
3,4,5-tri(octadecyloxy)benzyl alcohol;
4-methoxy-2-[3',4',5'-tris(octadecyloxy)benzyloxy)benzyl alcohol;
4-methoxy-2-[3',4',5'-tris(octadecyloxy)cyclohexylmethyl-oxy]benzyl alcohol;
2-docosyloxy-9-(4-chlorophenyl)-9-fluorenol;
2-docosyloxy-9-(4-chlorophenyl)-9-bromofluorene;
2,7-didocosyloxy-9-(4-chlorophenyl)-9-bromofluorene;
2-(12-docosyloxy-dodecanoxy)-9-(3-fluorophenyl)-9-bromofluorene;
1,12-bis-[12-(2'-O-9-(4-chlorophenyl)-9-fluorenol)-dodecy-loxy]-dodecane;
1,12-bis-[12-(2'-O-9-(4-chlorophenyl)-9-bromofluorene)-dodecyloxy]-dodecane;
2-(3-octadecyloxy-2,2-bis-octadecyloxymethyl-propoxy)-9-(4-chlorophenyl)-9-fluorenol;
2-(3-octadecyloxy-2,2-bis-octadecyloxymethyl-propoxy)-9-(4-chlorophenyl)-9-bromofluorene;
9-(4-chlorophenyl)-2-(3,4,5-tris(octadecyloxy)-cyclohexyl-methoxy)-9-fluorenol;
9-(4-chlorophenyl)-2-(3,4,5-tris(octadecyloxy)-cyclohexyl-methoxy)-9-bromofluorene;
3,5-didocosyloxybenzyl alcohol;
2,4-didocosyloxybenzyl alcohol;
2,4-bis octadecyloxybenzyl alcohol;
3-didocosylaminobenzyl alcohol;
3-diphytylaminobenzyl alcohol;
N-(2',3'-dihydrophytyl)-N-(3-hydroxymethylphenyl)acet-amide;
N-triacontyl-N-(3-hydroxymethylphenyl)acetamide;
3-(aminomethyl)-N,N-didocosylaniline;

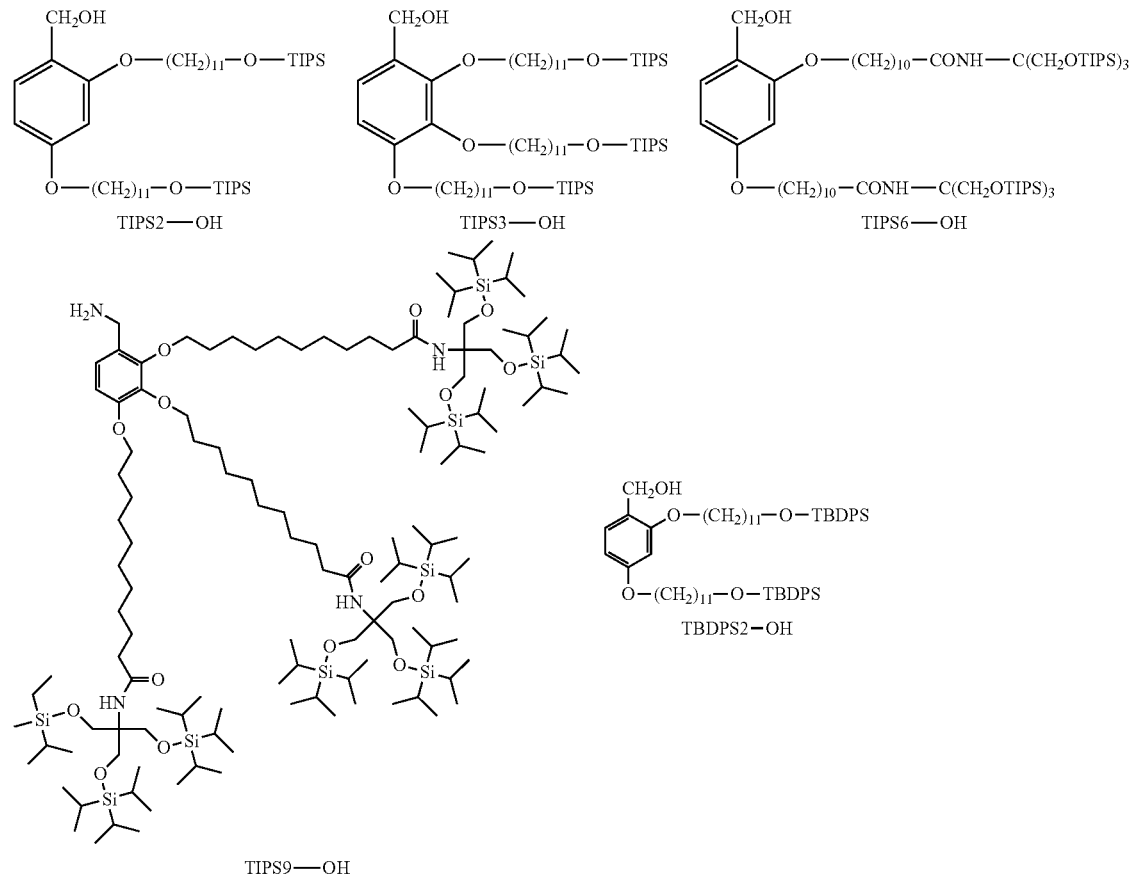

-continued
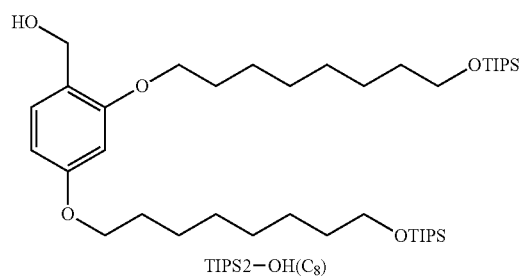
TIPS2—OH(C_8)
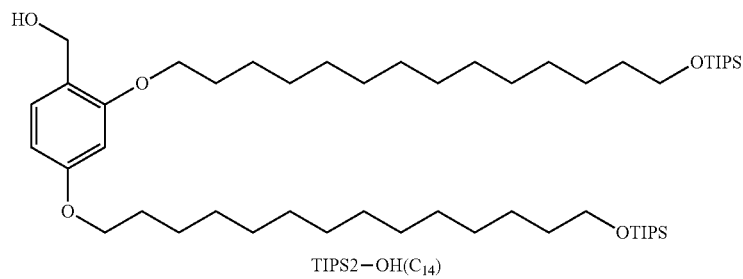
TIPS2—OH(C_14)
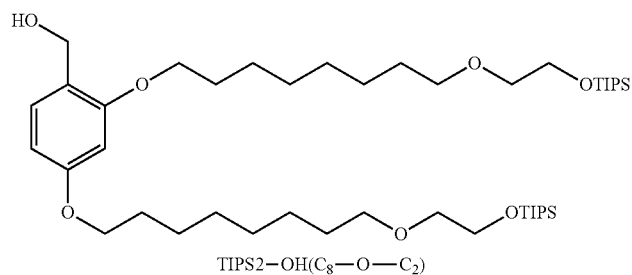
TIPS2—OH(C_8—O—C_2)
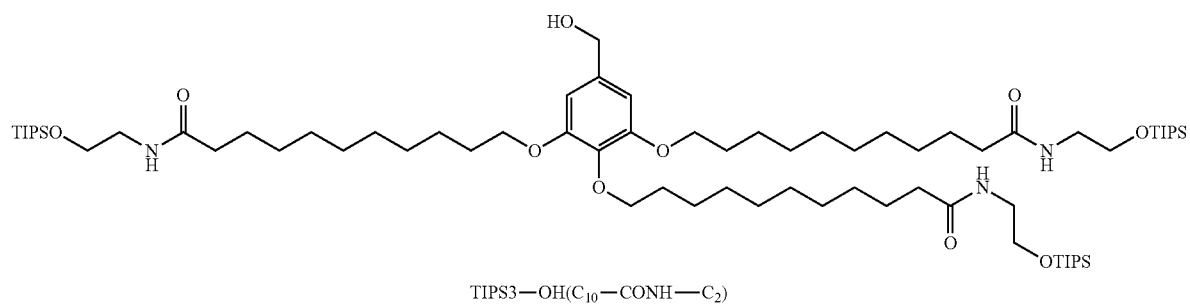
TIPS3—OH(C_10—CONH—C_2)
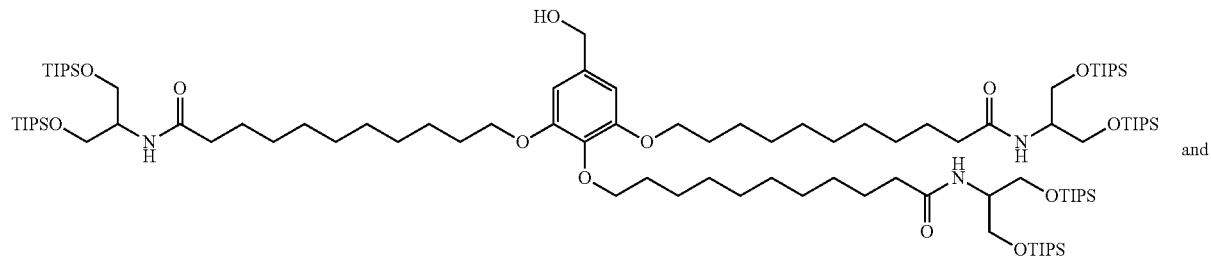
TIPS6—OH(C_10—CONH—CH(CH_2)_2) and
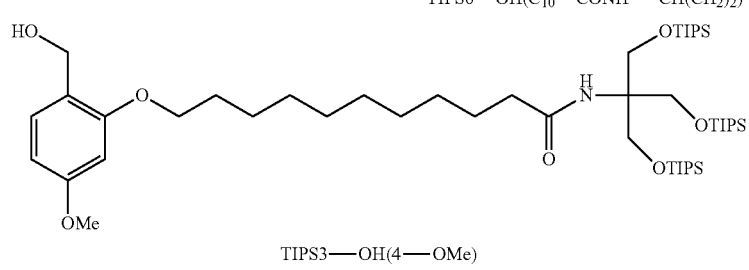
TIPS3—OH(4—OMe)

(in the above-mentioned formulas, TIPS is a triisopropylsilyl group, and TBDPS is a tert-butyldiphenylsilyl group).

(12) The production method of any of the above-mentioned (1) to (10), wherein the pseudo-solid-phase protecting group is selected from
(4',4'-bis(2,3-dihydrophytyloxy)phenyl)methylamine);
3,4,5-tri(2',3'-dihydrophytyloxy)benzyl alcohol;
2-[3,4,5-tri(2',3'-dihydrophytyloxy)benzyloxy]-4-methoxybenzylalcohol; and
3,4,5-tri(octadecyloxy)cyclohexanemethanol.

ADVANTAGEOUS EFFECTS OF INVENTION

According to the present invention, by using a peptide chain protected with a pseudo-solid-phase protecting group, solubility in a solvent can be maintained even when the peptide becomes a long chain, and reaction contaminants and the like can be removed easily. In addition, by utilization of elongation of peptide chain in a flow reactor, washing to remove unreacted products and by-products from the resultant product in a flow reactor in each step, and partitioning by an oil-water separation means in combination in a continuous flow, the purification/isolation process, which has been a problem of the peptide synthesis method in the liquid phase method, can be drastically simplified, and the synthesis and purification can be continuously performed in the entire flow of peptide production. According to the present invention, moreover, it is possible to shorten the post-treatment operation time in the peptide elongation stage (that is, condensation step and/or deprotection step) while taking advantage of peptide synthesis by the pseudo-solid-phase method that the resultant product can be easily purified and isolated by oil-water separation. As described above, the present invention provides a new method for producing a peptide, which improves the drawbacks of the conventional methods.

DETAILED DESCRIPTION OF THE PREFERRED EMBODIMENTS

An amino acid which is a constitutional unit of a peptide produced by the present invention is a compound having an amino group and a carboxy group in the same molecule, and may be a natural amino acid or non-natural amino acid, and an L form, a D form or a racemate. The constitutional unit is not limited to amino acids, and may be other compounds applicable to peptide synthesis (hereinafter referred to as amino acid analogs). Those of ordinary skill in the art can appropriately select such amino acid analogs and produce them according to a method known per se or a method similar thereto, or purchase them.

The steps (1), (A), (2), and (B) in the above-mentioned (1) and (2) in the present invention are described in detail in the following.

Flow Reactor

The flow reactor used in the steps (1), (A), (2), and (B) in the present invention is not particularly limited, and can be appropriately selected according to the desired reaction (function). In addition, one or more flow reactors may be connected to perform the reaction as appropriate.

Also, as the flow reactor, a flow microreactor that requires a micro effect is preferred, but a flow reactor that does not require a micro effect is also included.

Examples of the material of the flow reactor used in the reaction include metal, Teflon, glass, and silicon. From the aspects of compatibility with reagents, thermal conductivity, price, and the like, metal and Teflon are preferred.

According to the reaction, appropriate conditions can be selected for the amount of reagent, reaction temperature, and residence time during the reaction.

The pump and mixer to be used in the flow reactor are not limited and can be used as long as they are known in the art.

Step (1)

This step can be performed by introducing 1) a solution containing a soluble organic solvent, and a C-protected amino acid in which C-terminal is protected by a protecting group, a side chain functional group is optionally further protected by a protecting group, and at least one of the C-terminal or the side chain functional group is protected by a pseudo-solid-phase protecting group (C-protected amino acid), or a C-protected peptide in which C-terminal is protected by a protecting group, a side chain functional group is optionally further protected by a protecting group, and at least one of the C-terminal or the side chain functional group is protected by a pseudo-solid-phase protecting group (C-protected peptide), 2) a solution containing a soluble organic solvent, and an N-protected amino acid in which C-terminal is not protected, an N-terminal amino group is protected by a protecting group, and a side chain functional group is optionally further protected by a protecting group (N-protected amino acid), or an N-protected peptide in which C-terminal is not protected, an N-terminal amino group is protected by a protecting group, and a side chain functional group is optionally further protected by a protecting group (N-protected peptide), and 3) a solution containing a soluble organic solvent, and a condensing agent into a flow reactor each individually, simultaneously, or after appropriately mixing any two or more solutions, and mixing them in the flow reactor in a continuous flow, thus allowing a condensation reaction to proceed. Furthermore, a solution of a condensation promoter in a soluble organic solvent may be mixed as appropriate.

Here, the C-protected amino acid may be obtained by non-continuous batch synthesis, or may be separately purchased or obtained by other method.

In addition, the C-protected peptide may be obtained by performing the step (B) of the present invention, may be obtained by non-continuous batch synthesis, or may be separately purchased or obtained by other method. Among others, it is preferably obtained by performing the step (B) of the present invention.

Here, the N-terminal amino group of the C-protected amino acid or C-protected peptide need only be able to react with the N-protected amino acid or N-protected peptide. In addition to the case where the N-terminal amino group is unprotected, the N-terminal amino group may be substituted by one or more substituents. Examples of the substituent in that case include substituents generally used in an amino group (alkyl group having 1-6 carbon atoms, etc.), substituents that activate a reaction with N-protected amino acid or N-protected peptide, and the like. It is preferred that the N-terminal amino group of the C-protected amino acid or C-protected peptide is not protected.

Reaction Conditions of Step (1)

As described above, this step (1) can be performed by introducing 1) a solution containing C-protected amino acid or C-protected peptide, 2) a solution containing N-protected amino acid or N-protected peptide, and 3) a solution containing a condensing agent into a flow reactor each individually, simultaneously, or after appropriately mixing any two or more solutions, and mixing them in the flow reactor in a continuous flow, thus allowing a condensation reaction to proceed.

C-Protected Amino Acid/C-Protected Peptide
Pseudo-Solid-Phase Protecting Group

A pseudo-solid-phase protecting group used for protecting the C-terminal of C-protected amino acid or C-protected peptide (C-protected), or protecting a side chain functional group where necessary is a "protecting group using which it is possible to perform a reaction in a homogeneous liquid phase, and, after changing the solvent composition after the reaction, perform isolation and purification of the resultant product merely by oil-water separation". The pseudo-solid-phase protecting group is not particularly limited, including those known to those skilled in the art, and can be appropriately selected therefrom.

Among these, preferred pseudo-solid-phase protecting groups include the branched chain-containing aromatic compound described in WO 2012/029794, which is incorporated herein by reference in its entirety, and further, saturated carbocyclic compounds containing the branched chain. Specifically, they are shown by the following formula (I), and includes a specific benzyl compound (in the formula (I), X and Z are hydrogen atoms, and $R_1$ is a hydrogen atom); a specific diphenylmethane compound (in the formula (I), X is a hydrogen atom, $R_1$ is a hydrogen atom, k is 1, and Z is a group represented by the formula (a) wherein $R_2$ is a hydrogen atom, and m is 0)); and a specific fluorene compound (in the formula (I), X is a phenyl group, k is 1, Z is a group represented by the formula (a) wherein m is 0), and $R_2$ is joined with $R_1$ to form a single bond which forms a fluorene ring together with ring A).

A branched chain-containing compound represented by the formula (I):

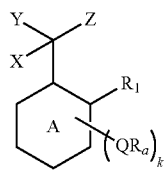

(I)

wherein
ring A is a benzene ring or a cyclohexane ring,
Q in the number of k are each independently a single bond, or —O—, —S—, —C(=O)O—, —C(=O)NH—, —NH— or —$NR_a$—;
$R_a$ in the $R_a$ in the number of k and —$NR_a$— are each independently an organic group having at least one aliphatic hydrocarbon group having one or more branched chains, having a total number of branched chains of not less than 3, and having a total carbon number of not less than 14 and not more than 300, —C(O)$R_{aa}$ or —S(O)$_2R_{aa}$ wherein $R_{aa}$ is a hydrogen atom, an aliphatic hydrocarbon group optionally having substituent(s), an aromatic hydrocarbon group optionally having substituent(s), or an aromatic heterocyclic group optionally having substituent(s);
k is an integer of 1 to 4;
$R_1$ is a hydrogen atom or, when Z is a group represented by the following formula (a), optionally shows a single bond together with $R_2$ to form a fluorene ring together with ring B;
ring A optionally further has, in addition to $R_1$, $QR_a$ in the number of k, and C(X)(Y)Z, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms;
X is a hydrogen atom or a phenyl group;
Y is a hydroxyl group or an —NHR group (R is a hydrogen atom, an alkyl group or an aralkyl group); and
Z is a hydrogen atom or a group represented by the formula (a):

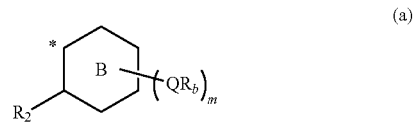

(a)

wherein * shows a binding site;
ring B is a benzene ring or a cyclohexane ring,
m is an integer of 0 to 4;
Q in the number of m are each independently a single bond, or —O—, —S—, —C(=O)O—, —C(=O)NH—, —NH— or —$NR_b$—;
$R_b$ in the $R_b$ in the number of m and —$NR_b$— are each independently an organic group having at least one aliphatic hydrocarbon group having one or more branched chains, having a total number of branched chains of not less than 3, and having a total carbon number of not less than 14 and not more than 300;
$R_2$ is a hydrogen atom, or optionally shows a single bond together with $R^1$ to form a fluorene ring together with ring A; and
ring B optionally further has, in addition to $QR_b$ in the number of m, and $R_2$, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms;
an organic group having at least one aliphatic hydrocarbon group having one or more branched chains, having a total number of branched chains of not less than 3, and having a total carbon number of not less than 14 and not more than 300 for the aforementioned $R_a$ and $R_b$ is a group having three or more, the same or different divalent groups represented by the formula (b):

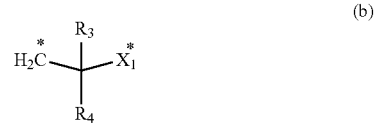

(b)

wherein * is a binding site with the adjacent atom;
$R_3$ and $R_4$ are each independently a hydrogen atom or a $C_{1-4}$ alkyl group; and
$X_1$ is a single bond, a $C_{1-4}$ alkylene group or an oxygen atom, provided that $R_3$ and $R_4$ are not hydrogen atoms at the same time, can be mentioned.

A compound represented by the formula (I) of the present invention and a compound intended to be protected are bound by a condensation reaction of a hydroxyl group or NHR group as a Y group and a carboxyl group at the C-terminal, etc of the compound intended to be protected.

In the present specification, as the "alkyl group" for R in the above-mentioned formula (I), a $C_{1-30}$ alkyl group can be mentioned. It is preferably a $C_{1-10}$ alkyl group, more preferably a $C_{1-6}$ alkyl group. Specific preferred examples include methyl, ethyl, propyl, isopropyl, butyl, isobutyl, sec-butyl, tert-butyl and the like, and methyl and ethyl are particularly preferred.

In the present specification, as the "aralkyl group" for R in the above-mentioned formula (I), a $C_{7-30}$ aralkyl group can be mentioned. It is preferably a $C_{7-20}$ aralkyl group, more preferably a $C_{7-16}$ aralkyl group ($C_{6-10}$ aryl-$C_{1-6}$ alkyl group). Specific preferred examples include benzyl, 1-phenylethyl, 2-phenylethyl, 1-phenylpropyl, α-naphthylmethyl, 1-(α-naphthyl)ethyl, 2-(α-naphthyl)ethyl, 1-(α-naphthyl)propyl, β-naphthylmethyl, 1-(β-naphthyl) ethyl, 2-(β-naphthyl)ethyl, 1-(β-naphthyl)propyl and the like, and benzyl is particularly preferred.

As R, a hydrogen atom, a $C_{1-6}$ alkyl group or a $C_{7-16}$ aralkyl group is preferred, a hydrogen atom, methyl, ethyl or benzyl is preferred, and a hydrogen atom is particularly preferred.

In the present specification, the "halogen atom" in the above-mentioned formula (I) is a fluorine atom, a chlorine atom, a bromine atom or an iodine atom.

In the present specification, the "ring A" in the above-mentioned formula (I) is a benzene ring or a cyclohexane ring, and both are preferred.

In the present specification, the "ring B" in the above-mentioned formula (I) is a benzene ring or a cyclohexane ring, and both are preferred.

In the present specification, the "organic group having at least one aliphatic hydrocarbon group having one or more branched chains, having a total number of branched chains of not less than 3, and having a total carbon number of not less than 14 and not more than 300" for $R_a$ or $R_b$ in the above-mentioned formula (I) is an organic group having at least one aliphatic hydrocarbon group having one or more branched chains in the molecule structure thereof, having a total number of branched chains of not less than 3, and having a total carbon number of not less than 14 and not more than 300.

The "branched chain" in the "aliphatic hydrocarbon group having one or more branched chains" is a straight chain or branched saturated aliphatic hydrocarbon group, preferably a $C_{1-6}$ alkyl group, more preferably a $C_{1-4}$ alkyl group, and further more preferably a methyl group or an ethyl group. The "branched chain" is optionally substituted by one or more halogen atoms.

The "aliphatic hydrocarbon group" in the "aliphatic hydrocarbon group having one or more branched chains" is a straight or branched saturated or unsaturated aliphatic hydrocarbon group, and is a $C_2$-$C_{300}$ alkyl group (preferably, $C_3$-$C_{100}$ alkyl group, more preferably, $C_3$-$C_{60}$ alkyl group), a $C_2$-$C_{300}$ alkenyl group (preferably, $C_3$-$C_{100}$ alkenyl group, more preferably, $C_3$-$C_{60}$ alkenyl group) or a $C_2$-$C_{300}$ alkynyl group (preferably, $C_3$-$C_{100}$ alkynyl group, more preferably, $C_3$-$C_{60}$ alkynyl group).

The moiety of the "aliphatic hydrocarbon group having one or more branched chains" in the "organic group having at least one aliphatic hydrocarbon group having one or more branched chains, having a total number of branched chains of not less than 3, and having a total carbon number of not less than 14 and not more than 300" is not particularly limited, and may be present at the terminal (monovalent group), or other site (e.g., divalent group).

Specific examples of the "aliphatic hydrocarbon group having one or more branched chains" include branched isomers such as a propyl group, a butyl group, a pentyl group, a hexyl group, a heptyl group, an octyl group, a nonyl group, a decyl group, an undecyl group, a dodecyl group (lauryl group), a tridecyl group, a myristyl group, a cetyl group, a stearyl group, an arachyl group, a behenyl group, an oleyl group, a linoryl group, a lignoceryl group and the like which are monovalent groups having one or more branched chains and divalent groups derived from them. Preferred are a 3,7,11-trimethyldodecyl group, a 3,7,11,15-tetramethylhexadecyl group (hereinafter sometimes to be referred to as 2,3-dihydrophytyl group.), a 2,2,4,8,10,10-hexamethylundecan-5-yl group, a group represented by the formula:

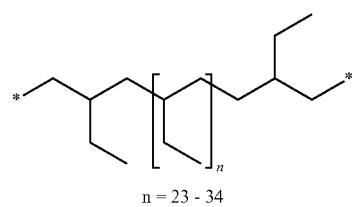

n = 23 - 34 wherein * is a binding site with Q, and the like.

When plural "aliphatic hydrocarbon groups having one or more branched chains" are present in the "organic group having at least one aliphatic hydrocarbon group having one or more branched chains, having a total number of branched chains of not less than 3, and having a total carbon number of not less than 14 and not more than 300", they may be the same or different.

The moiety other than the "aliphatic hydrocarbon group having one or more branched chains" of the "an organic group having at least one aliphatic hydrocarbon group having one or more branched chains, having a total number of branched chains of not less than 3, and having a total carbon number of not less than 14 and not more than 300" can be determined freely. For example, it may have a moiety such as —O—, —S—, —CO—, —NH—, —COO—, —OCONH—, —CONH—, —NHCO—, a hydrocarbon group (monovalent group or divalent group) and the like. Examples of the "hydrocarbon group" include an aliphatic hydrocarbon group, an aromatic-aliphatic hydrocarbon group, a monocyclic saturated hydrocarbon group, an aromatic hydrocarbon group and the like. Specifically, for example, monovalent groups such as an alkyl group, an alkenyl group, an alkynyl group, a cycloalkyl group, an aryl group, an aralkyl group and the like, and divalent groups derived therefrom are used. As the "alkyl group", a $C_{1-6}$ alkyl group and the like are preferred and for example, methyl, ethyl, propyl, isopropyl, butyl, isobutyl, sec-butyl, tert-butyl, pentyl, hexyl and the like can be mentioned. As the "alkenyl group", a $C_{2-6}$ alkenyl group and the like are preferred and for example, vinyl, 1-propenyl, allyl, isopropenyl, butenyl, isobutenyl and the like can be mentioned. As the "alkynyl group", a $C_{2-6}$ alkynyl group and the like are preferred and for example, ethynyl, propargyl, 1-propynyl and the like can be mentioned. As the "cycloalkyl group", a $C_{3-6}$ cycloalkyl group and the like are preferred and for example, cyclopropyl, cyclobutyl, cyclopentyl, cyclohexyl and the like can be mentioned. For example, the "aryl group" is preferably a $C_{6-14}$ aryl group and the like and for example, phenyl, 1-naphthyl, 2-naphthyl, biphenylyl, 2-anthryl and the like can be mentioned. Of these, a $C_{6-10}$ aryl group is preferred, and phenyl is particularly preferred. As the "aralkyl group", a $C_{7-20}$ aralkyl group is preferred and for example, benzyl, 1-phenylethyl, 2-phenylethyl, 1-phenylpropyl, naphthylmethyl, 1-naphthylethyl, 1-naphthylpropyl and the like can be mentioned. Of these, a $C_{7-16}$ aralkyl group ($C_{6-10}$ aryl-$C_{1-6}$ alkyl group) is preferred, and benzyl is particularly preferred. The "hydrocarbon group" may be substituted by a substituent selected from a halogen atom (a chlorine atom, a bromine atom, a fluorine atom, an iodine atom), an oxo group and the like.

The compound represented by the formula (I) has $QR_a$ group in the number of k. Here, Q is a single bond, or —O—, —S—, —C(=O)O—, —C(=O)NH— or —NH—, preferably —O—. The $QR_a$ group in the number of k may be each the same or different.

In a compound represented by the formula (I), the total carbon number of the "organic group having at least one aliphatic hydrocarbon group having one or more branched chains, having a total number of branched chains of not less than 3, and having a total carbon number of not less than 14 and not more than 300" for $R_a$ or $R_b$ is not less than 14, preferably not less than 16, more preferably not less than 18. On the other hand, the total carbon number of the "organic group having at least one aliphatic hydrocarbon group having one or more branched chains, and having an aliphatic hydrocarbon group with total number of branched chains of not less than 3" for $R_a$ or $R_b$ is not more than 300, preferably not more than 200, more preferably not more than 160. In addition, the total number of branched chains of the "organic group having at least one aliphatic hydrocarbon group having one or more branched chains, and having an aliphatic hydrocarbon group with total number of branched chains of not less than 3" for $R_a$ or $R_b$ is not less than 3, preferably not less than 4, more preferably not less than 8, further preferably not less than 10. As the total number of branched chains increases, the compound protected by the compound of the present invention becomes an oil having good solubility in various organic solvents even when the peptide chain becomes a long chain.

The "organic group having at least one aliphatic hydrocarbon group having one or more branched chains, having a total number of branched chains of not less than 3, and having a total carbon number of not less than 14 and not more than 300" for $R_a$ or $R_b$ is preferably a group having three or more, the same or different divalent groups represented by the formula (b):

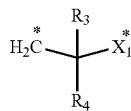

wherein * is a binding site with the adjacent atom;
$R_3$ and $R_4$ are each independently a hydrogen atom or a $C_{1-4}$ alkyl group; and
$X_1$ is a single bond, a $C_{1-4}$ alkylene group or an oxygen atom, provided that $R_3$ and $R_4$ are not hydrogen atoms at the same time) and, for example, a group represented by any of the following formulas (c) to (e) can be mentioned.

The number of carbon atoms, the number of repeat units ($m_1$, $n_0$-$n_9$) and the like in the definition of each symbol in the formulas (c)-(e) are shown for convenience, and can be changed as appropriate within the range of the above-mentioned definitions to fall under the total carbon number of not less than 14 (preferably not less than 16, more preferably not less than 18), and not more than 300 (preferably not more than 200, more preferably not more than 160). In the following, the formulas (c) to (e) are described in order.

The formula (c) is as follows.

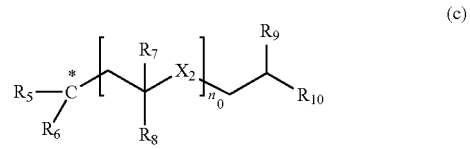

wherein * is a binding site with Q;
$R_5$ and $R_6$ are each a hydrogen atoms, or joined to show =O;
$n_0$ is an integer of 2 to 40;
$R_7$ and $R_9$ in the number of $n_0$ are each independently a hydrogen atom or a $C_{1-4}$ alkyl group;
$X_2$ in the number of $n_0$ are each independently a single bond or a $C_{1-4}$ alkylene group;
$R_9$ is a hydrogen atom or a $C_{1-4}$ alkyl group;
$R_{10}$ is a $C_{1-4}$ alkyl group or the formula (I'):

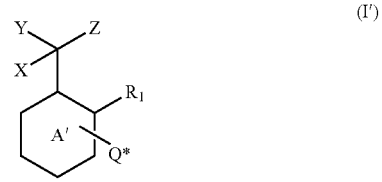

wherein * shows a binding site;
ring A' is a benzene ring or a cyclohexane ring;
other symbols are as defined above. Here, ring A' optionally further has, in addition to $R_1$, Q, and C(X)(Y)Z, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms.

However, $R_7$ and $R_8$ are not hydrogen atoms at the same time, and when $n_0$ is 2, $R_9$ is a $C_{1-4}$ alkyl group.

In the group of the formula (c), a group wherein
$R_5$ and $R_6$ are each a hydrogen atom;
$n_0$ is an integer of 2 to 40;
$R_7$ and $R_8$ in the number of $n_0$ are each independently a hydrogen atom, a methyl group or an ethyl group;
$X_2$ in the number of $n_0$ are each independently a single bond, a methylene group or an ethylene group; and $R_9$ is a hydrogen atom, a methyl group or an ethyl group is preferable (provided that
$R_7$ and $R_8$ are not hydrogen atoms at the same time, and when $n_0$ is 2, $R_9$ is methyl or an ethyl group).

A more preferable group of the formula (c) is a branched isomer having 14 to 160 carbon atoms and having a total number of branched chains of not less than 3, such as a myristyl group, a cetyl group, a stearyl group, an arachyl group, a behenyl group and the like. Of these, a 2,3-dihydrophytyl group, a 3,7,11-trimethyldodecyl group, and a 2,2,4,8,10,10-hexamethyl-5-dodecanoyl group are particularly preferred.

The formula (d) is as follows.

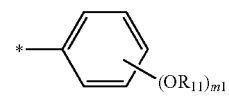

wherein * is a binding site with Q;
$OR_{11}$ in the number of $m_1$ is a hydroxyl group substituted by a group represented by the formula (c'), or a hydroxyl group substituted by a group having a polyalkylene glycol group having a total branched chain number of not less than 3 (e.g., polypropylene glycol group, polyneopentylglycol group); and $m_1$ is an integer of 1 to 3.

The description of the group represented by the above-mentioned formula (c') is the same as that of the group represented by the above-mentioned formula (c), except that indicates the binding site with 0, not with Q.

In the group of the formula (d), $R_{11}$ is more preferably a branched isomer having 14 to 30 carbon atoms and having a total number of branched chains of not less than 3, such as a myristyl group, a cetyl group, a stearyl group, an arachyl group, a behenyl group and the like. Of these, a 2,3-dihydrophytyl group and a 3,7,11-trimethyldodecyl group are particularly preferred.

The formula (e) is as follows.

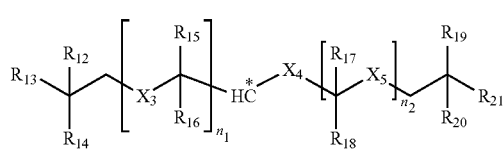

wherein * is a binding site with Q;
$n_1$ is an integer of 1 to 10;
$n_2$ is an integer of 1 to 10;
$R_{15}$ and $R_{16}$ in the number of $n_1$ are each independently a hydrogen atom or a $C_{1-4}$ alkyl group;
$X_3$ in the number of $n_1$ are each a single bond or a $C_{1-4}$ alkylene group;
$R_{17}$ and $R_{18}$ in the number of $n_2$ are each independently a hydrogen atom or a $C_{1-4}$ alkyl group;
$X_5$ in the number of $n_2$ are each a single bond or a $C_{1-4}$ alkylene group;
$X_4$ is a single bond or a $C_{1-4}$ alkylene group;
$R_{12}$, $R_{13}$, $R_{14}$, $R_{19}$, $R_{20}$ and $R_{21}$ are each independently a hydrogen atom or a $C_{1-4}$ alkyl group.

However, $R_{15}$ and $R_{16}$, and/or $R_{17}$ and $R_{18}$ are not hydrogen atoms at the same time, and when $n_1+n_2$ is 2, two or more of $R_{12}$, $R_{13}$ and $R_{14}$ are each independently a $C_{1-4}$ alkyl group, or two or m more of $R_{19}$, $R_{20}$ and $R_{21}$ are each independently a $C_{1-4}$ alkyl group.

In the group of the formula (e), a group wherein
$n_1$ is an integer of 1 to 5;
$n_2$ is an integer of 1 to 5;
$R_{15}$ and $R_{16}$ in the number of $n_1$ are each independently a hydrogen atom, a methyl group or an ethyl group;
$X_3$ in the number of $n_1$ are each independently a single bond, a methylene group or an ethylene group;
$R_{17}$ and $R_{18}$ in the number of $n_2$ are each independently a hydrogen atom, a methyl group or an ethyl group;
$X_5$ in the number of $n_2$ are each independently a single bond, a methylene group or an ethylene group;
$X_4$ is a single bond, a methylene group or an ethylene group; and
$R_{12}$, $R_{13}$, $R_{14}$, $R_{19}$, $R_{20}$ and $R_{21}$ are each independently a hydrogen atom or a $C_{1-4}$ alkyl group is more preferred (provided that $R_{13}$ and $R_{16}$, and/or $R_{17}$ and $R_{18}$ are not hydrogen atoms at the same time, and when $n_1+n_2$ is 2, two or more of $R_{12}$, $R_{13}$ and $R_{14}$ are each independently a $C_{1-4}$ alkyl group, or two or more of $R_{19}$, $R_{20}$ and $R_{21}$ are each independently a $C_{1-4}$ alkyl group).

As a particularly preferred group of the formula (e), a group wherein
$n_1$ is an integer of 1 to 5;
$n_2$ is an integer of 1 to 5;
$R_{15}$ and $R_{16}$ in the number of $n_1$ are each independently a hydrogen atom or a methyl group;
$X_3$ in the number of $n_1$ are each independently a single bond or a methylene group;
$R_{17}$ and $R_{18}$ in the number of $n_2$ are each independently a hydrogen atom or a methyl group;
$X_5$ in the number of $n_2$ are each independently a single bond or a methylene group;
$X_4$ is a single bond or a methylene group; and
$R_{12}$, $R_{13}$, $R_{14}$, $R_{19}$, $R_{20}$ and $R_{21}$ are each a methyl group can be mentioned (provided that $R_{15}$ and $R_{16}$, and/or $R_{17}$ and $R_{18}$ are not hydrogen atoms at the same time).

The "organic group having at least one aliphatic hydrocarbon group having one or more branched chains, having a total number of branched chains of not less than 3, and having a total carbon number of not less than 14 and not more than 300" for $R_a$ or $R_b$ may be, in addition to a group represented by any of the above-mentioned formulas (c) to (e), a group having not less than three groups in which $X_1$ in the above-mentioned formula (b) is an oxygen atom, that is, a group containing a polyalkylene glycol group with a total branched chain number of not less than 3 such as a polypropylene glycol group, a polyneopentylglycol group, and the like.

Specific examples of the "organic group having at least one aliphatic hydrocarbon group having one or more branched chains, having a total number of branched chains of not less than 3, and having a total carbon number of not less than 14 and not more than 300" for $R_a$ or $R_b$ include the following groups. In each group, * shows a binding site, $n_3$ in the formula is an integer of not less than 3, and $n_4$ can be appropriately determined to make the total carbon number of the group not less than 14 and not more than 300.

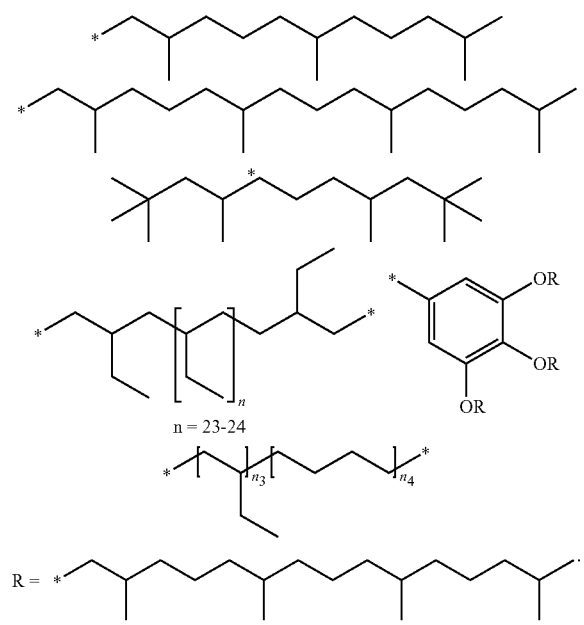

Another embodiment of the "organic group having at least one aliphatic hydrocarbon group having one or more branched chains, having a total number of branched chains of not less than 3, and having a total carbon number of not less than 14 and not more than 300" for $R_a$ or $R_b$ is the following group. In each group, * shows a binding site.

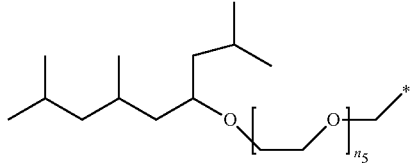

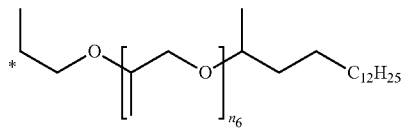

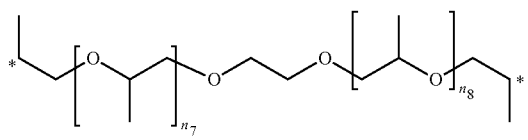

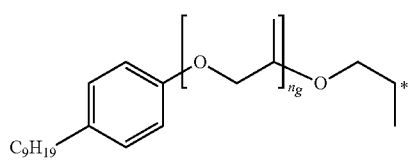

In the formula, $n_5$ to $n_9$ can be appropriately determined to make the total carbon number of each group not less than 14 and not more than 300.

Specific preferable examples of the "organic group having at least one aliphatic hydrocarbon group having one or more branched chains, having a total number of branched chains of not less than 3, and having a total carbon number of not less than 14 and not more than 300" for $R_a$ or $R_b$ include the m following groups:

3,7,11,15-tetramethylhexadecyl group;

3,7,11-trimethyldodecyl group;

2,2,4,8,10,10-hexamethyl-5-dodecanoyl group;

3,4,5-tri(3',7',11',15'-tetramethylhexadecyloxy)benzyl group;

3,5-di(3',7',11',15'-tetramethylhexadecyloxy)benzyl group;

a group represented by the formula (f):

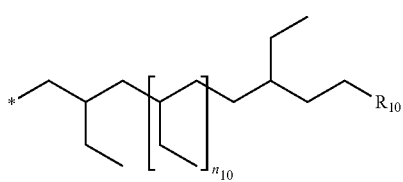

wherein * is a binding site with Q, $n_{10}$ is 23-34, and $R_{10}$ is a group represented by the formula (I');

a group represented by the formula (g):

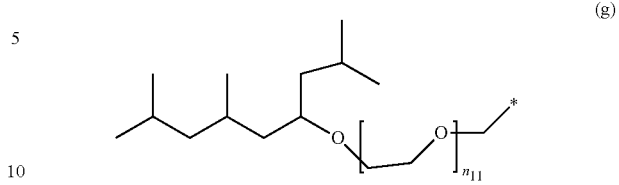

wherein * is a binding site with Q, and $n_{11}$ is 1-10;
a group represented by the formula (h):

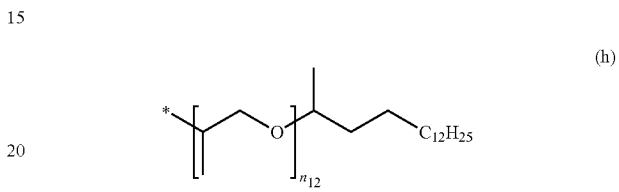

wherein * is a binding site with Q, and $n_{12}$ is 2-10;
a group represented by the formula (i):

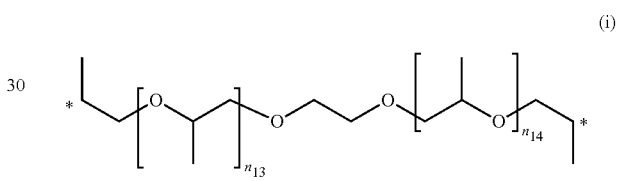

wherein * is a binding site with Q, and $n_{13}$ and $n_{14}$ are each independently 1 to 10; and
a group represented by the formula (j):

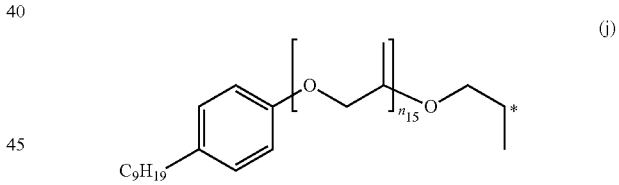

wherein * is a binding site with Q, and $n_{15}$ is 2 to 20.
More preferably, the following compounds can be recited:
2,4-di(2',3'-dihydrophytyloxy)benzyl alcohol;
3,5-di(2',3'-dihydrophytyloxy)benzyl alcohol;
4-(2',3'-dihydrophytyloxy)benzyl alcohol;
1-[(2-chloro-5-(2',3'-dihydrophytyloxy)phenyl)]-1-phenylmethaneamine;
3,4,5-tri(2',3'-dihydrophytyloxy)benzyl alcohol;
3,4,5-tri(2',3'-dihydrophytyloxy)benzylamine;
4-(2',3'-dihydrophytyloxy)benzylamine;
2-[3,4,5-tri(2',3'-dihydrophytyloxy)benzyloxy]-4-methoxybenzyl alcohol (MTBPhy-OH);
4-(2',3'-dihydrophytyloxy)-2-methoxybenzyl alcohol;
4-(2',3'-dihydrophytyloxy)-2-methoxybenzylamine;
4-(2',3'-dihydrophytyloxy)-2-methylbenzyl alcohol;
4-(2',3'-dihydrophytyloxy)-2-methylbenzylamine;
2,2,4,8,10,10-hexamethyl-5-dodecanoic acid (4-hydroxymethyl)phenylamide;
4-(3,7,11-trimethyldodecyloxy)benzyl alcohol;
2-(3,7,11-trimethyldodecyloxy)-9-phenylfluoren-9-ol;

a compound represented by the formula:

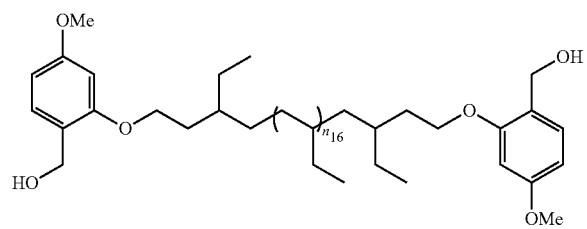

wherein $n_{16}$ is 23 or 34;

a compound represented by the formula:

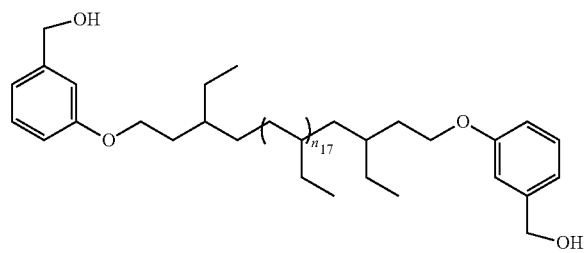

wherein $n_{17}$ is 23 or 34;

a compound represented by the formula:

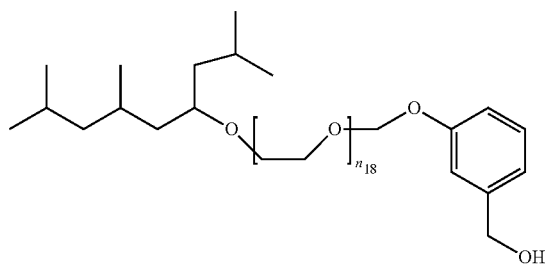

wherein $n_{18}$ is 5 to 7; and a compound represented by the formula:

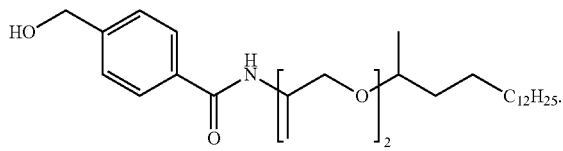

While the production method of the aforementioned pseudo-solid-phase protecting group is not particularly limited, it can be produced from a starting material compound according to a method known per se (see [0128]-[0154] of WO 2012/029794, which is incorporated herein by reference in its entirety) or a method analogous thereto. A compound used as a starting material compound, for example, halide corresponding to the group $R^2$ or $R^4$ in the formula (I) and the like can be obtained as a commercially available product or can be produced by a method known per se or a method analogous thereto.

As other preferable pseudo-solid-phase protecting groups in the present invention, the pseudo-solid-phase protecting groups described in any of WO 2016/140232, WO 2003/018188, WO 2017/038650, and WO 2019/009317, all of which are incorporated herein by reference in their entireties, can be mentioned. Of these, WO 2017/038650 describes a benzyl compound with a terminal modified with a silyl-based protecting group as a pseudo-solid-phase protecting group, and these pseudo-solid-phase protecting groups are also included in the present invention.

As a pseudo-solid-phase protecting group that can be used in the present invention, the pseudo-solid-phase protecting groups described in JP-A-2000-44493, WO 2006/104166, WO 2007/034812, WO 2007/122847, WO 2010/113939, WO 2010/104169, WO 2011/078295, all of which are incorporated herein by reference in their entireties, and the like can also be mentioned in addition to those mentioned above.

More specifically, as one embodiment of the pseudo-solid-phase protecting group described above, a group containing a pseudo-solid-phase protecting group soluble in halogenated solvents or ether solvents, insoluble in polar solvents and having a molecular weight of not less than 300 (e.g., benzyl compound, diphenylmethane compound, or fluorene compound, and saturated carbocyclic compounds thereof), and capable of condensing with a carboxy group at the C-terminal can be mentioned.

One embodiment of the above-mentioned pseudo-solid-phase protecting group soluble in halogenated solvents or ether solvents, insoluble in polar solvents and having a molecular weight of not less than 300 is a compound represented by the following formula (II). Among such compounds, one having a molecular weight of not less than 400 is preferable. The formula (II):

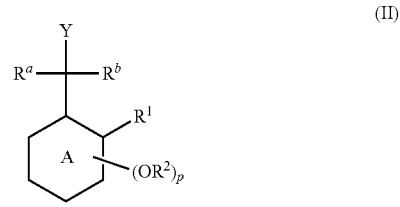

wherein ring A is a benzene ring or a cyclohexane ring, $R^1$ is a hydrogen atom or, when $R^b$ is a group represented by the following formula (a'), optionally shows a single bond together with $R^3$ to form a fluorene ring together with ring A and ring B;

$R^2$ in the number of p are each independently an organic group having an aliphatic hydrocarbon group;

p is an integer of 1 to 4;

ring A optionally further has, in addition to $OR^2$ in the number of p, a substituent selected from the group consisting of a halogen atom, a $C_{1-6}$ alkyl group optionally substituted by a halogen atom, and a $C_{1-6}$ alkoxy group optionally substituted by a halogen atom;

$R^a$ is a hydrogen atom, or a phenyl group optionally substituted by a halogen atom; and $R^b$ is a hydrogen atom, or a group represented by the formula (a'):

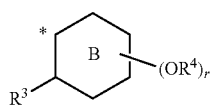

wherein * is a binding site;
ring B is a benzene ring or a cyclohexane ring,
r is an integer of 0 to 4;
$R^4$ in the number of r are each independently an organic group having an aliphatic hydrocarbon group;
$R^3$ is a hydrogen atom, or optionally shows a single bond together with $R^1$ to form a fluorene ring together with ring A and ring B; and
ring B optionally further has, in addition to $OR^4$ in the number of r, a substituent selected from the group consisting of a halogen atom, a $C_{1-6}$ alkyl group optionally substituted by a halogen atom, and a $C_{1-6}$ alkoxy group optionally substituted by a halogen atom; and
Y is a hydroxy group, NHR (R is a hydrogen atom, an alkyl group or an aralkyl group) or a halogen atom.

The pseudo-solid-phase protecting group represented by the above-mentioned formula (II) is bound to a compound intended to be protected. That is, a pseudo-solid-phase protecting group wherein Y is a hydroxy group, an —NHR group or a halogen atom protects a compound by condensing with the C-terminal of amino acid or peptide and the like.

In the present specification, as the "alkyl group" for R in the above-mentioned formula (II), a straight or branched $C_{1-30}$ alkyl group can be mentioned. It is preferably a $C_{1-10}$ alkyl group, more preferably a $C_{1-6}$ alkyl group. Specific preferable examples include methyl, ethyl, propyl, isopropyl, butyl, isobutyl, sec-butyl, tert-butyl and the like, and methyl and ethyl are particularly preferable.

In the present specification, as the "aralkyl group" for R in the above-mentioned formula (II), a $C_{7-30}$ aralkyl group can be mentioned. It is preferably a $C_{7-20}$ aralkyl group, more preferably a $C_{7-16}$ aralkyl group ($C_{6-10}$ aryl-$C_{1-6}$ alkyl group). Specific preferable examples include benzyl, 1-phenylethyl, 2-phenylethyl, 1-phenylpropyl, naphthylmethyl, 1-naphthylethyl, 1-naphthylpropyl and the like, and benzyl is particularly preferable.

As R, a hydrogen atom, a $C_{1-6}$ alkyl group or a $C_{7-16}$ aralkyl group is preferable, a hydrogen atom, methyl, ethyl or benzyl is more preferable, and a hydrogen atom is particularly preferable.

In the present specification, the "halogen atom" in the above-mentioned formula (II) is a fluorine atom, a chlorine atom, a bromine atom or an iodine atom. In the present specification, as the "halogen atom" for Y, a chlorine atom, a bromine atom or an iodine atom is preferable, and a bromine atom is more preferable.

In the present specification, the "ring A" in the above-mentioned formula (II) is a benzene ring or a cyclohexane ring, and both are preferred.

In the present specification, the "ring B" in the above-mentioned formula (II) is a benzene ring or a cyclohexane ring, and both are preferred.

In the present specification, the "organic group having an aliphatic hydrocarbon group" for $R^2$ or $R^4$ in the above-mentioned formula (II) is a monovalent organic group having an aliphatic hydrocarbon group in a molecule structure thereof.

The "aliphatic hydrocarbon group" in the "organic group having an aliphatic hydrocarbon group" is a straight or branched saturated or unsaturated aliphatic hydrocarbon group, preferably an aliphatic hydrocarbon group having 5 or more carbon atoms, more preferably an aliphatic hydrocarbon group having 5 to 60 carbon atoms, further preferably an aliphatic hydrocarbon group having 5 to 30 carbon atoms, particularly preferably an aliphatic hydrocarbon group 10 to 30 carbon atoms. The moiety of the "aliphatic hydrocarbon group" in the "organic group having an aliphatic hydrocarbon group" is not particularly limited, and may be present at the terminal (monovalent group), or other site (for example, divalent group).

Examples of the "aliphatic hydrocarbon group" include monovalent groups such as an alkyl group, a cycloalkyl group, an alkenyl group, a cycloalkenyl group, an alkynyl group and the like, and divalent groups derived therefrom, preferably monovalent groups such as a methyl group, an ethyl group, a propyl group, an isopropyl group, a butyl group, an isobutyl group, a sec-butyl group, a tert-butyl group, a pentyl group, a hexyl group, an octyl group, a decyl group, a dodecyl group, a lauryl group, a tridecyl group, a myristyl group, a cetyl group, a stearyl group, an arachyl group, a behenyl group, an oleyl group, an isostearyl group and the like, and divalent groups derived therefrom.

The moiety other than the "aliphatic hydrocarbon group" of the "organic group having an aliphatic hydrocarbon group" can be set freely. For example, it may have a moiety such as —O—, —S—, —COO—, —OCONH—, —CONH—, a hydrocarbon group (monovalent group or divalent group) and the like as a linker. Examples of the "hydrocarbon group" include an aliphatic hydrocarbon group, an aromatic-aliphatic hydrocarbon group, a monocyclic saturated hydrocarbon group, an aromatic hydrocarbon group and the like. Specifically, for example, monovalent groups such as an alkyl group, an alkenyl group, an alkynyl group, a cycloalkyl group, an aryl group, an aralkyl group and the like, and divalent groups derived therefrom are used. As the "alkyl group", a $C_{1-6}$ alkyl group and the like are preferable and, for example, methyl, ethyl, propyl, isopropyl, butyl, isobutyl, sec-butyl, tert-butyl, pentyl, hexyl and the like can be mentioned. As the "alkenyl group", a $C_{2-6}$ alkenyl group and the like are preferable and, for example, vinyl, 1-propenyl, allyl, isopropenyl, butenyl, isobutenyl and the like can be mentioned. As the "alkynyl group", a $C_{2-6}$ alkynyl group and the like are preferable and, for example, ethynyl, propargyl, 1-propynyl and the like can be mentioned. As the "cycloalkyl group", a $C_{3-6}$ cycloalkyl group and the like are preferable and, for example, cyclopropyl, cyclobutyl, cyclopentyl, cyclohexyl and the like can be mentioned. For example, the "aryl group" is preferably a $C_{6-14}$ aryl group and the like and, for example, phenyl, 1-naphthyl, 2-naphthyl, biphenylyl, 2-anthryl and the like can be mentioned. Of these, a $C_{6-10}$ aryl group is more preferable, and phenyl is particularly preferable. As the "aralkyl group", a $C_{7-20}$ aralkyl group is preferable and, for example, benzyl, 1-phenylethyl, 2-phenylethyl, 1-phenylpropyl, naphthylmethyl, 1-naphthylethyl, 1-naphthylpropyl and the like can be mentioned. Of these, a $C_{7-16}$ aralkyl group ($C_{6-10}$ aryl-$C_{1-6}$ alkyl group) is more preferable, and benzyl is particularly preferable. The "hydrocarbon group" may be substituted by a substituent selected from a halogen atom (a chlorine atom, a bromine atom, a fluorine atom, an iodine atom), an alkyl group having 1 to 6 carbon atoms and optionally substituted by one or more halogen atoms, an oxo group and the like.

In the "organic group having an aliphatic hydrocarbon group" constituting the $OR^2$ group or $OR^4$ group in the above-mentioned formula (II), plural "aliphatic hydrocarbon groups" may be present by branching and the like. When plural "aliphatic hydrocarbon groups" are present in the "organic is group having an aliphatic hydrocarbon group", they may be the same or different.

In the "organic group having an aliphatic hydrocarbon group" for $R^2$ or $R^4$ in the above-mentioned formula (II), the lower limit of the total carbon number is preferably 5, more preferably 10, further preferably 12, still more preferably 14, especially preferably 16, and particularly preferably 20. On the other hand, in the "organic group having an aliphatic hydrocarbon group" for $R^2$ or $R^4$, the upper limit of the total carbon number is preferably 200, more preferably 150, further preferably 120, still more preferably 100, especially preferably 80, particularly preferably 60, particularly further preferably 40, and most preferably 30. The compound protected by the compound of the present invention becomes an oil having good solubility in various organic solvents even when the peptide chain becomes a long chain.

Specific preferable examples of the "$OR^2$" group or "$OR^4$" group include dodecyloxy, cetyloxy, octadecyloxy, docosyloxy, docosyloxy-dodecyloxy, triacontyloxy and the like. The "$OR^2$" group or "$OR^4$" group is present in a total number of p or r (p is an integer of 1 to 4 and r is an integer of 0 to 4), p is preferably 2 or 3, and r is preferably an integer of 0 to 2.

Specific preferable examples of the substituent optionally present in ring A or ring B in the above-mentioned formula (II) include a $C_{1-6}$ alkoxy group (e.g., a $C_{1-4}$ alkoxy group such as methoxy, ethoxy, propoxy, isopropoxy, butoxy, isobutoxy, sec-butoxy, tert-butoxy and the like), a $C_{1-6}$ alkyl group optionally substituted by one or more halogens (e.g., a $C_{1-6}$ alkyl group such as methyl, ethyl, propyl, isopropyl, butyl, isobutyl, sec-butyl, tert-butyl, pentyl, hexyl and the like, a halogen-substituted $C_{1-6}$ alkyl group such as trifluoromethyl, trichloromethyl and the like), and a halogen atom. Of these, a $C_{1-6}$ alkoxy group is preferable.

A preferable embodiment of the pseudo-solid-phase protecting group represented by the above-mentioned formula (II) is a compound of the formula (II), wherein
Y is a hydroxy group;
$R^1$ is a hydrogen atom;
$R^2$ and/or $R^4$ are/is an aliphatic hydrocarbon group having 5 to 60 carbon atoms;
p is an integer of 1 to 3; and
r is an integer of 0 to 2.

Another preferable embodiment of the pseudo-solid-phase protecting group represented by the above-mentioned formula (II) is a compound of the formula (II), wherein
Y is a hydroxy group;
$R^a$, $R^b$, and $R^1$ are each a hydrogen atom;
$R^2$ is an aliphatic hydrocarbon group having 5 to 60 carbon atoms; and
p is an integer of 1 to 3.

Another preferable embodiment of the pseudo-solid-phase protecting group represented by the above-mentioned formula (II) is a compound of the formula (II), wherein
Y is a hydroxy group;
$R^a$, $R^b$, and $R^1$ are each a hydrogen atom;
$R^2$ is an alkyl group having 10 to 40 carbon atoms; and
p is 2 or 3.

Another preferable embodiment of the pseudo-solid-phase protecting group represented by the above-mentioned formula (II) is a compound of the formula (II), wherein
Y is a hydroxy group;
$R^a$, $R^b$, and $R^1$ are each a hydrogen atom;
$R^2$ is an alkyl group having 12 to 30 carbon atoms; and
p is 2 or 3.

Another preferable embodiment of the pseudo-solid-phase protecting group represented by the above-mentioned formula (II) is a compound of the formula (II), wherein
Y is a hydroxy group;
$R^a$, $R^b$, and $R^1$ are each a hydrogen atom;
$R^2$ is a benzyl group having 1 to 3 alkoxy groups having 12 to 30 carbon atoms; and
p is an integer of 1 to 3.

Another preferable embodiment of the pseudo-solid-phase protecting group represented by the above-mentioned formula (II) is a compound of the formula (II), wherein
Y is a hydroxy group;
$R^a$, $R^b$, and $R^1$ are each a hydrogen atom;
$R^2$ is a cyclohexylmethyl group having 1 to 3 alkoxy groups having 12 to 30 carbon atoms; and
p is an integer of 1 to 3.

Preferable examples of the pseudo-solid-phase protecting group soluble in halogenated solvents or ether solvents, insoluble in polar solvents and having a molecular weight of not less than 300 in the present invention, which is described in detail above, include the following pseudo-solid-phase protecting groups.

2,3,4-trioctadecanoxybenzohydrol;
[phenyl(2,3,4-trioctadecanoxyphenyl)methyl]amine;
4,4'-didocosoxybenzohydrol;
di(4-docosoxyphenyl)methylamine;
4,4-di(12-docosoxydodecyloxy)benzohydrol;
amino-bis[4-(12-docosoxydodecyloxy)phenyl]methane;
N-benzyl-[bis(4-docosyloxyphenyl)]methylamine;
(4-methoxy-phenyl)-[4-(3,4,5-tris-octadecyloxy-cyclohexylmethoxy)-phenyl]-methanol;
{(4-methoxy-phenyl)-[4-(3,4,5-tris-octadecyloxy-cyclohexylmethoxy)-phenyl]-methyl}-amine;
[bis-(4-docosoxy-phenyl)-methyl]-amine, and
(4',4'-bis(2,3-dihydrophytyloxy)phenyl)methylamine) ($NH_2$-Dpm(OPhy));
4-(12'-docosyloxy-1'-dodecyloxy)benzyl alcohol;
4-(12'-docosyloxy-1'-dodecyloxy)-2-methoxybenzylalcohol;
4-(12'-docosyloxy-1'-dodecyloxy)-2-methoxybenzylamine;
2-(12'-docosyloxy-1'-dodecyloxy)-4-methoxybenzyl alcohol;
2-(12'-docosyloxy-1'-dodecyloxy)-4-methoxybenzylamine;
2-docosyloxy-4-methoxybenzyl alcohol;
4-methoxy-2-[3',4',5'-tris(octadecyloxy)benzyloxy)benzyl alcohol;
2-[3',5'-di(docosyloxy)benzyloxy]-4-methoxybenzyl alcohol;
2-methoxy-4-[2',2',2'-tris(octadecyloxymethyl)ethoxy)benzyl alcohol;
2-methoxy-4-[2',2',2'-tris(octadecyloxymethyl)ethoxy]benzylamine;
4-methoxy-2-[3',4',5'-tris(octadecyloxy)cyclohexylmethyloxy]benzyl alcohol;
2-methoxy-4-[3',4',5'-tris(octadecyloxy)cyclohexylmethyloxy]benzyl alcohol;
4-[3',4',5'-tris(octadecyloxy)cyclohexylmethyloxy]benzyl alcohol;
3,5-dimethoxy-4-[3',4',5'-tris(octadecyloxy)cyclohexylmethyloxy]benzyl alcohol;
N-(4-hydroxymethyl-3-methoxyphenyl)-3,4,5-tris(octadecyloxy)cyclohexylcarboxamide;
N-(5-hydroxymethyl-2-methoxyphenyl)-3,4,5-tris(octadecyloxy)cyclohexylcarboxamide;

N-(4-hydroxymethylphenyl)-3,4,5-tris(octadecyloxy)cyclohexylcarboxamide;
1,22-bis[12-(4-hydroxymethyl-3-methoxyphenoxy)dodecyloxy]docosane; or
1,22-bis[12-(2-hydroxymethyl-5-methoxyphenoxy)dodecyloxy]docosane;
2,4-di(2',3'-dihydrophytyloxy)benzyl alcohol;
3,5-di(2',3'-dihydrophytyloxy)benzyl alcohol;
4-(2',3'-dihydrophytyloxy)benzyl alcohol;
1-[(2-chloro-5-(2',3'-dihydrophytyloxy)phenyl)]-1-phenylmethaneamine;
3,4,5-tri(2',3'-dihydrophytyloxy)benzyl alcohol (TOBPhy-OH);
3,4,5-tri(2',3'-dihydrophytyloxy)benzylamine;
4-(2',3'-dihydrophytyloxy)benzylamine;
2-[3,4,5-tri(2',3'-dihydrophytyloxy)benzyloxy]-4-methoxybenzyl alcohol (MTBPhy-OH);
4-(2',3'-dihydrophytyloxy)-2-methoxybenzyl alcohol;
4-(2',3'-dihydrophytyloxy)-2-methoxybenzylamine;
4-(2',3'-dihydrophytyloxy)-2-methylbenzyl alcohol;
4-(2',3'-dihydrophytyloxy)-2-methylbenzylamine;
2,2,4,8,10,10-hexamethyl-5-dodecanoic acid (4-hydroxymethyl)phenylamide;
4-(3,7,11-trimethyldodecyloxy)benzyl alcohol;
2-(3,7,11-trimethyldodecyloxy)-9-phenylfluoren-9-ol;
3,4,5-tri(octadecyloxy)benzyl alcohol;
3,4,5-tri(octadecyloxy)cyclohexanemethanol (TOC-OH);
2,4-di(docosyloxy)benzyl alcohol;
4-methoxy-2-[3',4',5'-tri(octadecyloxy)benzyloxy]benzyl alcohol;
4-methoxy-2-[3',4',5'-tri(octadecyloxy)cyclohexylmethyloxy]benzyl alcohol;
2-methoxy-4-[3',4',5'-tri(octadecyloxy)cyclohexylmethyloxy]benzyl alcohol;
4-[3',4',5'-tri(octadecyloxy)cyclohexylmethyloxy]benzyl alcohol;
3,5-dimethoxy-4-[3',4',5'-tri(octadecyloxy)cyclohexylmethyloxy]benzyl alcohol;
2,4-di(dodecyloxy)benzyl alcohol;
3,4,5-tri(octadecyloxy)benzylamine;
bis(4-docosyloxyphenyl)methanol;
bis(4-docosyloxyphenyl)methylamine;
2-(12-docosyloxy-dodecyloxy)-9-(3-fluorophenyl)-9-bromofluorene.
[bis-(4-docosoxy-phenyl)-methyl]-amine;
3,4,5-tri(octadecyloxy)benzyl alcohol;
4-methoxy-2-[3',4',5'-tri(octadecyloxy)benzyloxy)benzyl alcohol; and
4-methoxy-2-[3',4',5'-tri(octadecyloxy)cyclohexylmethyloxy]benzyl alcohol.
Of the above, the following pseudo-solid-phase protecting groups are more preferred.
(4',4'-bis(2,3-dihydrophytyloxy)phenyl)methylamine) (NH$_2$-Dpm(OPhy));
3,4,5-tri(2',3'-dihydrophytyloxy)benzyl alcohol (TOBPhy-OH);
2-[3,4,5-tri(2',3'-dihydrophytyloxy)benzyloxy]-4-methoxybenzyl alcohol (MTBPhy-OH);
3,4,5-tri(octadecyloxy)cyclohexanemethanol (TOC-OH);
[bis-(4-docosoxy-phenyl)-methyl]-amine;
3,4,5-tri(octadecyloxy)benzyl alcohol;
4-methoxy-2-[3',4',5'-tris(octadecyloxy)benzyloxy)benzyl alcohol; and
4-methoxy-2-[3',4',5'-tris(octadecyloxy)cyclohexylmethyloxy]benzyl alcohol.
In addition to the above, the following pseudo-solid-phase protecting groups are also preferred as other groups.

(pseudo-solid-phase protecting groups described in WO 2010/104169, which is incorporated herein by reference in its entirety)
2-docosyloxy-9-(4-chlorophenyl)-9-fluorenol;
2-docosyloxy-9-(4-chlorophenyl)-9-bromofluorene;
2,7-didocosyloxy-9-(4-chlorophenyl)-9-bromofluorene;
2-(12-docosyloxy-dodecanoxy)-9-(3-fluorophenyl)-9-bromofluorene;
1,12-bis-[12-(2'-O-9-(4-chlorophenyl)-9-fluorenol)-dodecyloxy]-dodecane;
1,12-bis-[12-(2'-O-9-(4-chlorophenyl)-9-bromofluorene)-dodecyloxy]-dodecane;
2-(3-octadecyloxy-2,2-bis-octadecyloxymethyl-propoxy)-9-(4-chlorophenyl)-9-fluorenol;
2-(3-octadecyloxy-2,2-bis-octadecyloxymethyl-propoxy)-9-(4-chlorophenyl)-9-bromofluorene;
9-(4-chlorophenyl)-2-(3,4,5-tris(octadecyloxy)cyclohexylmethoxy)-9-fluorenol;
9-(4-chlorophenyl)-2-(3,4,5-tris(octadecyloxy)-cyclohexylmethoxy)-9-bromofluorene.
(the following pseudo-solid-phase protecting groups described in WO 2010/104169, which is incorporated herein by reference in its entirety)
2-docosyloxy-9-(4-chlorophenyl)-9-fluorenol;
2-docosyloxy-9-(4-chlorophenyl)-9-bromofluorene;
2,7-didocosyloxy-9-(4-chlorophenyl)-9-bromofluorene;
2-(12-docosyloxy-dodecanoxy)-9-(3-fluorophenyl)-9-bromofluorene;
1,12-bis-[12-(2'-O-9-(4-chlorophenyl)-9-fluorenol)-dodecyloxy]-dodecane;
1,12-bis-[12-(2'-O-9-(4-chlorophenyl)-9-bromofluorene)-dodecyloxy]-dodecane;
2-(3-octadecyloxy-2,2-bis-octadecyloxymethyl-propoxy)-9-(4-chlorophenyl)-9-fluorenol;
2-(3-octadecyloxy-2,2-bis-octadecyloxymethyl-propoxy)-9-(4-chlorophenyl)-9-bromofluorene;
9-(4-chlorophenyl)-2-(3,4,5-tris(octadecyloxy)-cyclohexylmethoxy)-9-fluorenol;
9-(4-chlorophenyl)-2-(3,4,5-tris(octadecyloxy)-cyclohexylmethoxy)-9-bromofluorene.
(pseudo-solid-phase protecting groups described in WO 2007/122847, which is incorporated herein by reference in its entirety)
3,5-didocosyloxybenzyl alcohol;
2,4-didocosyloxybenzyl alcohol.
(pseudo-solid-phase protecting group described in WO 2007/034812, which is incorporated herein by reference in its entirety)
2,4-bisoctadecyloxybenzyl alcohol.
(pseudo-solid-phase protecting groups described in WO 2016/140232, which is incorporated herein by reference in its entirety)
3-didocosylaminobenzyl alcohol;
3-diphytylaminobenzyl alcohol;
N-(2',3'-dihydrophytyl)-N-(3-hydroxymethylphenyl)acetamide;
N-triacontyl-N-(3-hydroxymethylphenyl)acetamide;
3-(aminomethyl)-N,N-didocosylaniline.
(pseudo-solid-phase protecting groups described in WO 2019/009317, which is incorporated herein by reference in its entirety)

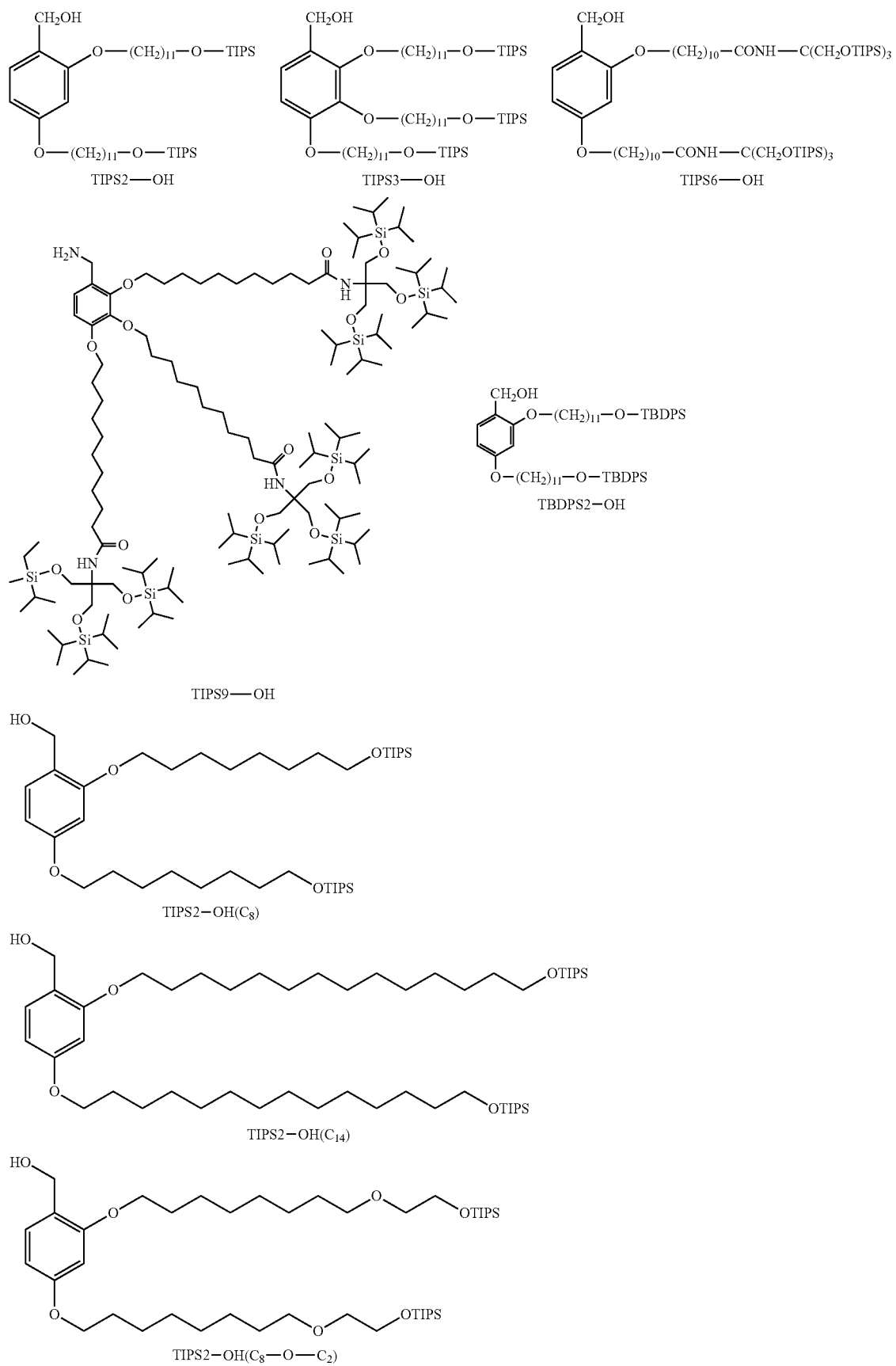

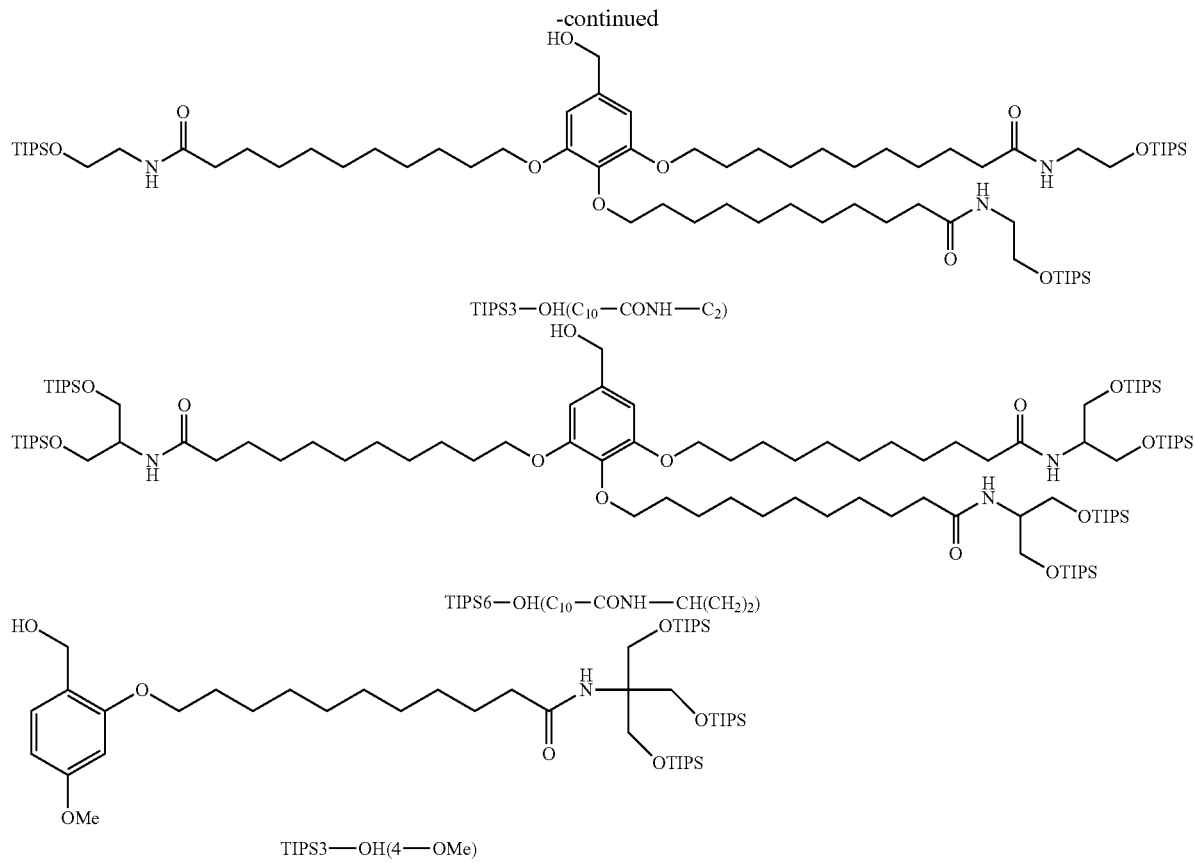

Among the pseudo-solid-phase protecting groups described above, the following are examples of particularly preferable pseudo-solid-phase protecting groups.

(4′,4′-bis(2,3-dihydrophytyloxy)phenyl)methylamine) (NH$_2$-Dpm(OPhy));

3,4,5-tri(2′,3′-dihydrophytyloxy)benzyl alcohol (TOBPhy-OH);

2-[3,4,5-tri(2′,3′-dihydrophytyloxy)benzyloxy]-4-methoxybenzyl alcohol (MTBPhy-OH); and 3,4,5-tri(octadecyloxy)cyclohexanemethanol (TOC-OH).

While the production method of the aforementioned pseudo-solid-phase protecting groups is not particularly limited, they can be produced from starting material compounds according to a method known per se (JP-A-2000-44493, WO 2006/104166, WO 2007/034812, WO 2007/122847, WO 2010/113939, WO 2010/104169, WO 2011/078295, all of which are incorporated herein by reference in their entireties and the like) or a method analogous thereto.

C-Terminal Protecting Group

As the C-terminal protecting group, an ester-type protecting group, an amide-type protecting group, a hydrazide-type protecting group and the like can be mentioned in addition to the aforementioned pseudo-solid-phase protecting group.

As the ester-type protecting group, substituted or unsubstituted alkyl ester, and substituted or unsubstituted aralkyl ester are preferably used. As the substituted or unsubstituted alkyl ester, methyl ester, ethyl ester, tert-butyl ester, cyclohexyl ester, trichloroethyl ester, phenacyl ester and the like are preferably used. As the substituted or unsubstituted aralkyl ester, benzyl ester, p-nitrobenzyl ester, p-methoxybenzyl ester, diphenylmethyl ester, 9-fluorenylmethyl (Fm) ester, 4-picolyl (Pic) ester and the like are preferably used.

As the amide-type protecting group, unsubstituted amide, primary amide such as N-methylamide, N-ethylamide, N-benzylamide and the like, secondary amide such as N,N-dimethylamide, pyrrolidinylamide, piperidinylamide and the like, and the like are preferably used.

As the hydrazide-type protecting group, unsubstituted hydrazide, N-phenylhydrazide, N,N′-diisopropylhydrazide and the like are preferably used.

Of these, t-butyl ester which is stable under the N-terminal amino group deprotection conditions, substituted or unsubstituted benzyl ester and the like are preferably used, and substituted or unsubstituted benzyl ester is particularly preferably used since synthesis thereof is comparatively easy.

Protecting Group of Side Chain Functional Group

An amino acid or peptide to be used in the present invention often has, in addition to an amino group or carboxy group involved in the formation of a peptide bond, a functional group subjected to a dehydration condensation reaction, such as an amino group, a carboxy group, a hydroxy group and the like. Such functional group is distinguished from an amino group and a carboxy group forming a peptide bond of the main chain, and referred to as a side chain functional group. While the side chain functional group does not need to be always protected as long as it does not impair the gist of the present invention, it is preferably protected by an appropriate protecting group to prevent an undesirable side reaction during peptide bond formation by a dehydration condensation reaction and deprotection of an N-terminal amino groups.

The protecting group of the side chain functional group is subject to a certain limitation on the combination with the N-terminal amino-protecting group, like the aforementioned C-terminal-protecting group. That is, the protecting group of the side chain functional group needs to be maintained until the completion of the desired amino acid sequence, without being removed even under the removing conditions of the protecting group (e.g., Fmoc group) of the N-terminal amino group. The protecting group is not particularly limited as long as the side chain functional group does not cause an undesirable side reaction during formation of the peptide bond by a dehydration condensation reaction and deprotection of the N-terminal amino group.

The protecting group of the side chain functional group is not particularly limited as long as it is stable under the deprotection conditions of the protecting group (temporary protecting group) of the N-terminal amino group. For example, the protecting groups described in PEPTIDE GOUSEI NO KISO TO JIKKENN (basis and experiment of peptide synthesis), published by Maruzen Co., Ltd. (1985), PROTECTIVE GROUPS IN ORGANIC SYNTHESIS, the third edition, published by JOHN WILLY&SONS (1999), which is incorporated herein by reference in its entirety, and the like can be mentioned.

When the side chain functional group is a carboxy group, the protecting groups same as those described above as the C-terminal protecting group can be mentioned.

When the side chain functional group is a carboxy group, it may be protected by the above-mentioned pseudo-solid-phase protecting group, and this embodiment is also encompassed in the scope of the present invention.

When the side chain functional group is an amino group, a urethane-type protecting group, an acyl-type protecting group, a sulfonyl-type protecting group and the like can be mentioned.

As the urethane-type protecting group, for example, a methoxycarbonyl group, an ethoxycarbonyl group, a tert-butoxycarbonyl (Boc) group, a benzyloxycarbonyl (Cbz) group and the like are used, and a methoxycarbonyl group, an ethoxycarbonyl group, a Boc group and the like are preferable. Of these, a Boc group is particularly preferably used since selective deprotection thereof is possible under mild acidic conditions.

As the acyl-type protecting group, for example, a formyl group, an acetyl group, a trifluoroacetyl group and the like are preferably used.

As the sulfonyl-type protecting group, for example, a p-toluenesulfonyl (Ts) group, a p-tolylmethanesulfonyl group, a 4-methoxy-2,3,6-trimethylbenzenesulfonyl group and the like are preferably used.

As for side chain functional groups other than those mentioned above, one stable under the deprotection conditions of the protecting group (temporary protecting group) (e.g., Fmoc group, and the like) of the N-terminal amino group can be selected and used.

For example, when the functional group on peptide is a hydroxy group (including phenolic hydroxy group), an alkyl-type protecting group, an alkoxyalkyl-type protecting group, an acyl-type protecting group, an alkylsilyl-type protecting group and the like can be mentioned.

Examples of the alkyl-type protecting group include a methyl group, an ethyl group, a tert-butyl group and the like.

Examples of the alkoxyalkyl-type protecting group include a methoxymethyl group (MOM group), a 2-tetrahydropyranyl group (THP group), an ethoxyethyl group (EE group), and the like.

Examples of the acyl-type protecting group include an acetyl group, a pivaloyl group, a benzoyl group, and the like.

Examples of the alkylsilyl-type protecting group include a trimethylsilyl group (TMS group), a triethylsilyl group (TES group), a tert-butyldimethylsilyl group (TBS group or TBDMS group), a triisopropyl silyl group (TIPS group), a tert-butyldiphenylsilyl group (TBDPS group), and the like.

Other functional groups can also be protected by protecting groups conventionally used in the pertinent technical field. For example, the guanidino group of arginine can be protected by a p-toluenesulfonyl group, 2,2,4,6,7-pentamethyldihydrobenzofuran-5-sulfonyl group (Pbf) group and the like. The amide group of asparagine and glutamine, and the imidazole group of histidine can be protected by a trityl group, a benzyloxymethyl group, and the like. The SH group of cysteine can be protected by a trityl. In addition, the indole group of tryptophan can be protected by a Boc group, a formyl group, or the like.

While the protecting group for the functional group on peptide is described above, those of ordinary skill in the art can perform this step by appropriately selecting the protecting group according to the protection scheme (e.g., Fmoc/tBu strategy, tBu/Bzl strategy, Bzl/tBu strategy, etc.) selected in the technical field according to the overall synthetic strategy for carrying out the present invention. Among these, the Fmoc/tBu strategy is preferred.

The side chain functional group can be deprotected as necessary after forming the object peptide bond.

N-Protected Amino Acid/N-Protected Peptide

Protecting group of N-terminal amino group

The protecting group (temporary protecting group) of the N-terminal amino group of an acid component to be used for the condensation step in the present invention is, for example, a 9-fluorenylmethyloxycarbonyl group (hereinafter to be also referred to as Fmoc group), a tert-butoxycarbonyl group (hereinafter to be also referred to as Boc group) or a benzyloxycarbonyl group (hereinafter to be also referred to as Cbz group (or Z group)), and it is preferably an Fmoc group or a Boc group. It is most preferably an Fmoc group.

The Cbz group may also be used in peptide synthesis. However, it takes time and effort to blow hydrogen gas into a flow reactor by using a metal powder in catalytic reduction at the time of deprotection. Considering synthesis of a longer chain peptide, an Fmoc group and a Boc group are more preferred. Of these, the Boc group is sometimes preferred in a sequence that does not contain Cys, Met, or the like. The Fmoc group is particularly preferred because it can be used for general purposes in peptide synthesis regardless of the sequence. In addition, it is essential to remove the reaction residue derived from the Fmoc group generated during deprotection. In the present invention, the Fmoc group is particularly preferred from the aspect that this residue can be easily removed by using the pseudo-solid-phase protecting group.

Preferred side chain functional groups are the same protecting groups as those described above for C-protected amino acid/C-protected peptide.

The C-protected amino acid, C-protected peptide, N-protected amino acid, N-protected peptide to be used in this step can be appropriately synthesized by those skilled in the art, starting from a known compound and according to a method known in the art or a method described in the present specification.

Condensing Agent and the Like

This step is performed under peptide synthesis conditions generally used in the field of peptide chemistry and using a condensing agent, a condensation promoter and the like.

As the condensing agent, dicyclohexylcarbodiimide (DCC), diisopropylcarbodiimide (DIC), N-ethyl-N'-3-dimethylaminopropylcarbodiimide and hydrochloride thereof (EDC HCl), (benzotriazol-1-yloxy)tripyrrolidinophosphonium hexafluorophosphate (PyBop), O-(benzotriazol-1-yl)-N,N,N',N'-tetramethyluronium tetrafluoroborate (TBTU), [O-(7-azo-benzotriazol-1-yl)-1,1,3,3-tetramethyluronium hexafluorophosphate](HATU), 1-[bis (dimethylamino)methylene]-5-chloro-1H-benzotriazolium 3-oxide hexafluorophosphate (HCTU), O-benzotriazole-N,N,N',N'-tetramethyluronium hexafluorophosphate (HBTU), 2-chloro-4,6-dimethoxy-1,3,5-triazine-N-methylmorpholine (DMT-MM), N'-cyclooctyl-N,N-dimethylurea (COMU) and the like can be mentioned. Of these, water-soluble condensing agents are preferred, and 2-chloro-4,6-dimethoxy-1,3,5-triazine-N-methylmorpholine (DMT-MM) or N-ethyl-N'-3-dimethylaminopropylcarbodiimide hydrochloride (EDC.HCl) is more preferred.

The amount of the condensing agent to be used is, for example, 1 to 10 mol, preferably 1 to 5 mol, per 1 mol of the C-protected amino acid or C-protected peptide.

As a condensation promoter, 1-hydroxybenzotriazole (HOBt), ethyl 1-hydroxy-1H-1,2,3-triazole-5-carboxylate (HOCt), 1-hydroxy-7-azabenzotriazole (HOAt), O-(benzotriazol-1-yl)-N,N,N',N'-tetramethyluronium hexafluorophosphate (HBTU), [O-(7-azobenzotriazol-1-yl)-1,1,3,3-tetramethyluronium hexafluorophosphate](HATU), O-(6-chlorobenzotriazol-1-yl)-N,N,N',N'-tetramethyluronium hexafluorophosphate (HCTU), ethyl 2-cyano-2-hydroxyiminoacetate (Oxyma), and the like can be mentioned, with preference given to HOBt and Oxyma.

The amount of the condensation promoter to be used is preferably not less than 0.05 mol, more preferably not less than 0.9 mol, preferably not more than 1.5 mol, more preferably not more than 1.1 mol, per 1 mol of the aforementioned C-protected amino acid or C-protected peptide.

A particularly preferable combination of a condensing agent and a condensation promoter in this step is that of N-ethyl-N'-3-dimethylaminopropylcarbodiimide hydrochloride (EDC HCl) and 1-hydroxybenzotriazole (HOBt) or ethyl 2-cyano-2-hydroxyiminoacetate (Oxyma).

The above-mentioned condensing agent and condensation promoter also include those for N-terminal activation in addition to those for C-terminal activation.

Solvent

The solvent to be used is a soluble organic solvent and is not particularly limited as long as it can dissolve each reaction component. A solvent that does not affect the reaction is preferable. The higher the solubility in the solvent, superior reactivity can be expected. Therefore, it is preferable to select a solvent having a high solubility of each reaction component. In view of partitioning by an oil-water separation means in a later step, a solvent immiscible with water is preferred. Specifically, ethers such as diethyl ether, tetrahydrofuran (THF), 1,4-dioxane, methyl-t-butylether, cyclopentylmethylether (CPME) and the like; acetic acid esters such as ethyl acetate, isopropyl acetate and the like; halogenated hydrocarbons such as chloroform, dichloromethane and the like; aromatic hydrocarbons such as toluene, xylene and the like; hydrocarbons such as hexane, heptane, cyclohexane and the like can be mentioned. Two or more kinds of these solvents may be used in a mixture in an appropriate ratio. Since good extraction operation is expected and industrial use is possible, tetrahydrofuran (THF), ethyl acetate, isopropyl acetate, chloroform, dichloromethane, cyclopentylmethylether (CPME), and toluene are preferred, tetrahydrofuran (THF), ethyl acetate, isopropyl acetate, cyclopentylmethylether (CPME), and toluene are more preferred, tetrahydrofuran (THF), ethyl acetate, isopropyl acetate, and cyclopentylmethylether (CPME) are further preferred, tetrahydrofuran (THF), chloroform, isopropyl acetate, cyclopentylmethylether (CPME) are still more preferred. Mixed solvents of these solvents and a polar organic solvent (dimethylformamide (DMF), etc.) are also acceptable.

A preferable concentration of a solution containing C-protected amino acid or C-protected peptide, or a solution containing N-protected amino acid or N-protected peptide, is, for example, an amount of a 3- to 1000-fold diluted solvent.

Reaction Conditions

When the flow reactor in step (1) is used, suitable conditions can be selected as appropriate for the mixing conditions, flow (flow rate), and temperature control conditions of each solution. As the mixing conditions of the solution, it is preferable to use a T-shaped mixer or a cross-shaped mixer.

The flow (flow rate) varies depending on the piping, and suitable conditions can be selected as appropriate.

As the temperature control condition, 5 to 50° C. is preferable.

Step (A)

This step is performed by introducing a reaction mixture containing N-protected C-protected peptide, water and/or a hydrophilic organic solvent into a flow reactor each individually, simultaneously, or after mixing, washing in a continuous flow, partitioning the "aqueous layer or hydrophilic organic solvent layer" and an organic layer by an oil-water separation means in a continuous flow, and separating the organic layer containing the N-protected C-protected peptide. In this way, the purification and isolation of the N-protected C-protected peptide can be performed efficiently for the subsequent step.

Here, the N-protected C-protected peptide may be obtained by performing the step (1) of the present invention, may be obtained by non-continuous batch synthesis, or may be separately purchased or obtained by other method. Among others, it is preferably obtained by performing the step (1) of the present invention.

Water and/or hydrophilic organic solvent can be used to remove and wash unreacted substances and by-products at the time of extraction. A hydrophilic organic solvent may be used instead of water.

Water also includes a mixed solution of water and sodium chloride. Neutral is preferred.

Specific examples of the hydrophilic organic solvent include nitriles such as acetonitrile, propionitrile and the like; ketones such as acetone, methyl ethyl ketone, 2-butanone and the like; amides such as N,N-dimethylformamide (DMF), N-methylpyrrolidone (NMP) and the like; and sulfoxides such as dimethyl sulfoxide (DMSO) and the like. Acetonitrile, N,N-dimethylformamide (DMF), and N-methylpyrrolidone (NMP) are preferred since they aid solubility and do not affect layer separation.

When only a hydrophilic organic solvent is used, for example, nitriles such as acetonitrile, propionitrile and the like, and amides such as N,N-dimethylformamide (DMF), N-methylpyrrolidone (NMP) and the like are preferred, and acetonitrile, N,N-dimethylformamide (DMF) or N-methylpyrrolidone (NMP) is particularly preferred. In this case, an organic solvent that is immiscible with a hydrophilic organic solvent (e.g., hydrocarbons such as hexane, heptane, cyclohexane and the like; aromatic hydrocarbons such as toluene, xylene and the like; halogenated hydrocarbons such as chloroform, dichloromethane and the like) is used as a reaction solvent to partition the hydrophilic organic solvent and the organic layer, and the organic layer can be separated.

As water and a hydrophilic organic solvent, a mixed solvent of water and a hydrophilic organic solvent (acetonitrile, N,N-dimethylformamide (DMF), or N-methylpyrrolidone (NMP)), and a mixed solvent of "a mixed solution of water and sodium chloride" and a hydrophilic organic solvent (acetonitrile, N,N-dimethylformamide (DMF), or N-methylpyrrolidone (NMP)) are preferred.

As the concentration condition, 5- to 100-fold dilution with respect to the substrate (N-protected C-protected peptide) is preferable.

Regarding washing, suitable conditions can be selected as appropriate with respect to the mixing method and washing time. Washing in neutral is preferable, and "a mixed solution of water and sodium chloride" is preferable.

Examples of the oil-water separation means include a continuous layer separation means having a structure including a filter and a Gravity type continuous layer separation means. Here, any filter can be selected as appropriate, and examples thereof include means having a constitution including a filter such as a membrane filter and the like. For example, a liquid-liquid separator system of Zaiput Flow Technologies can be used.

The Gravity type continuous layer separation means is a layer separation means using gravity, which is a continuous separatory funnel, and includes a means of gradually draining the liquid from the separated bottom layer and the top layer. Means including a Gravity Settler, means including an inclined plate, and the like can also be mentioned. For example, Lamella Gravity Settler of Parkson, and the like can be mentioned.

When the flow reactor in step (A) is used, suitable conditions can be selected as appropriate for the mixing conditions, flow (flow rate), and temperature control conditions of each solution. Unlimitatively, conditions under which a slug flow (flow in which organic layer and aqueous layer are alternately repeated) is formed after introduction of a reaction mixture containing N-protected C-protected peptide, and water and/or a hydrophilic organic solvent into a flow reactor are particularly preferred. The conditions can be appropriately determined by those of ordinary skill in the art.

Step (2)

This step is performed by introducing the organic layer comprising the N-protected C-protected peptide into a flow reactor in a continuous flow, and removing the protecting group of the N-terminal amino group in the flow reactor in a continuous flow to obtain a C-protected peptide in which an N-terminal amino group is not protected, C-terminal is protected by a protecting group, a side chain functional group is optionally further protected by a protecting group, and at least one of the C-terminal or the side chain functional group is protected by a pseudo-solid-phase protecting group (N-unprotected C-protected peptide).

The N-unprotected C-protected peptide may be obtained by performing the step (A) of the present invention, may be obtained by non-continuous batch synthesis, or may be separately purchased or obtained by other method. Among others, it is preferably obtained by performing the step (A) of the present invention.

The removal (deprotection) of the N-terminal protecting group of the N-protected C-protected peptide can be performed by a method known in the field of peptide synthesis. For example, when the protecting group is an Fmoc group, the deprotection is performed by treating with a base, when the protecting group is a Boc group, it is performed by treating with an acid, and when the protecting group is a Cbz group, it is performed by a catalytic reduction and the like.

The deprotection is performed by introducing a solution of N-protected C-protected peptide in a solvent that does not influence the reaction into a flow reactor as appropriate. According to the kind of the protecting group to be removed, a solution of a preferable reagent for deprotection (organic base, acid, catalyst for catalytic reduction, and the like) dissolved in a solvent that does not influence the reaction, or a suspension obtained by suspending in a solvent that does not influence the reaction is also introduced into the flow reactor. When catalytic reduction is performed, a hydrogen gas is further introduced into the flow reactor.

Introduction of each reaction component into a flow reactor can be performed by introducing each individually, simultaneously, or after appropriately mixing any two or more reaction components into a flow reactor, mixing in the flow reactor in a continuous flow, and allowing a deprotection reaction to proceed.

While the organic base usable for the removal of an Fmoc group is not particularly limited, secondary amines such as diethylamine, piperidine, morpholine and the like, tertiary amines such as diisopropylethylamine, dimethylaminopyridine, 1,8-diazabicyclo[5.4.0]-7-undecene (DBU), 1,4-diazabicyclo[2.2.2]octane (DABCO), 1,5-diazabicyclo[4.3.0]-5-nonene (DBN) and the like can be mentioned. The amount of the organic base to be used is, for example, 1-100 mol, preferably 1-10 mol, per 1 mol of the aforementioned N-protected C-protected peptide.

More preferably, the Fmoc group is removed by treating same with a non-nucleophilic organic base in a halogenated solvent or ether solvent. The deprotection is performed in a solvent that does not influence the reaction.

Examples of the non-nucleophilic base include 1,8-diazabicyclo[5.4.0]-7-undecene (DBU), 1,4-diazabicyclo[2.2.2]octane (DABCO), 1,5-diazabicyclo[4.3.0]-5-nonene (DBN) and the like. DBU and DBN are preferred, and DBU is more preferred. The amount of the non-nucleophilic base to be used is preferably not less than 0.8 equivalents, more preferably not less than 1 equivalent, preferably not more than 5 equivalents, more preferably not more than 3 equivalents, with respect to the reaction substrate (N-FmoC-protected C-protected amino acid or N-FmoC-protected C-protected peptide).

The halogen-based solvent or the ether-based solvent may be a mixed solvent of two or more kinds. The halogen-based solvent or the ether-based solvent is preferably chloroform, dichloromethane, tetrahydrofuran (THF) or cyclopentylmethylether (CPME). These can be used by mixing with N,N-dimethylformamide (DMF). In addition, propylene carbonate can be used as the solvent, and when propylene carbonate is used, a mixed solvent with N,N-dimethylformamide (DMF) or N-methylpyrrolidone (NMP) is preferred.

The above-mentioned Fmoc group removal reaction is more preferably performed in the coexistence of 3-mercaptopropionic acid, thiomalic acid, or cysteine. In particular, it is preferably performed in the coexistence of thiomalic acid.

When the temporary protecting group of the N-terminal is an Fmoc group, a neutralization step by the addition of an acid may be incorporated before the next step, since an excess amount of the organic base used for the deprotection may exhibit an adverse influence on the reaction product during working up such as solvent evaporation and the like.

While the acid usable for the removal of a Boc group is not particularly limited, mineral acids such as hydrogen chloride, sulfuric acid, nitric acid and the like, carboxylic acids such as formic acid, trifluoroacetic acid (TFA) and the like, sulfonic acids such as methanesulfonic acid, p-toluenesulfonic acid and the like, or a mixture thereof can be used. As the mixture, for example, hydrogen bromide/acetic acid, hydrogen chloride/dioxane, hydrogen chloride/acetic acid and the like can be mentioned. When an acid other than an aqueous solution is used, for example, when formic acid, methanesulfonic acid and the like are used in a non-aqueous system, for example, it is possible to selectively remove the Boc group while retaining a pseudo-solid-phase protecting group, which is a protecting group of carboxy group subject to hydrolysis under acidic conditions. Particularly, water-soluble sulfonic acids which are liquid at ambient temperature such as methanesulfonic acid and the like are preferable since, when they are used in a non-aqueous system, they can quickly progress the reaction at room temperature with a comparatively small amount of use. The amount of the acid to be used is, for example, 1 to 100 mol, preferably 1 to 10 mol, per 1 mol of the aforementioned N-protected C-protected amino acid or N-protected C-protected peptide.

While the catalyst usable for the removal of the Cbz group is not particularly limited, for example, palladium and the like can be mentioned. The amount of the catalyst to be used is, for example, not less than 1 part by weight, preferably not less than 5 parts by weight, for example, not more than 50 parts by weight, preferably 30 parts by weight, per 100 parts by weight of the aforementioned N-protected C-protected peptide.

Examples of the solvent that does not influence the reaction include halogenated solvents such as chloroform, dichloromethane, 1,2-dichloroethane and the like; aromatic hydrocarbons such as toluene, xylene and the like; ether solvents such as diethyl ether, cyclopentylmethylether (CPME), tetrahydrofuran (THF), 1,4-dioxane and the like; and the like, or a mixture thereof, preferably chloroform, dichloromethane and tetrahydrofuran (THF).

When the flow reactor in step (2) is used, suitable conditions can be selected as appropriate for the mixing conditions, flow (flow rate), and temperature control conditions of each solution. As the mixing conditions of the solution, it is preferable to use a T-shaped mixer or a cross-shaped mixer.

The flow (flow rate) varies depending on the piping, and suitable conditions can be selected as appropriate.

As the temperature control condition, 5-50° C. is preferable.

Step (B)

This step is performed by introducing a reaction mixture containing N-unprotected C-protected peptide, and water and/or a hydrophilic organic solvent into a flow reactor each individually, simultaneously, or after mixing, washing in a continuous flow, subjecting to an oil-water separation means in a continuous flow to partition the "aqueous layer or hydrophilic organic solvent layer" and an organic layer, and separating the organic layer containing the N-unprotected C-protected peptide. In this way, the purification and isolation of the N-unprotected C-protected peptide can be performed efficiently for the subsequent step.

Here, the N-unprotected C-protected peptide may be obtained by performing the step (2) of the present invention, may be obtained by non-continuous batch synthesis, or may be separately purchased or obtained by other method. Among others, it is preferably obtained by performing the step (2) of the present invention.

Water and/or hydrophilic organic solvent can be used to remove and wash unreacted substances and by-products at the time of extraction. Various hydrophilic organic solvents may be used instead of water.

Water also includes a mixed solution of water and sodium carbonate or potassium carbonate, and a mixed solution of water and sodium chloride.

Specific examples of the hydrophilic organic solvent include nitriles such as acetonitrile, propionitrile and the like; ketones such as acetone, methyl ethyl ketone, 2-butanone and the like; amides such as N,N-dimethylformamide (DMF), N-methylpyrrolidone (NMP) and the like; and sulfoxides such as dimethyl sulfoxide (DMSO) and the like. Acetonitrile, N,N-dimethylformamide (DMF), and N-methylpyrrolidone (NMP) are preferred since they aid solubility and do not affect layer separation.

When only a hydrophilic organic solvent is used, for example, nitriles such as acetonitrile, propionitrile and the like, and amides such as N,N-dimethylformamide (DMF), N-methylpyrrolidone (NMP) and the like are preferred, and acetonitrile, N,N-dimethylformamide (DMF), or N-methylpyrrolidone (NMP) is particularly preferred. In this case, an organic solvent that is immiscible with a hydrophilic organic solvent (e.g., hydrocarbons such as hexane, heptane, cyclohexane and the like; aromatic hydrocarbons such as toluene, xylene and the like; halogenated hydrocarbons such as chloroform, dichloromethane and the like) is used as a reaction solvent to partition the hydrophilic organic solvent and the organic layer, and the organic layer can be separated.

As water and a hydrophilic organic solvent, a mixed solvent of water and a hydrophilic organic solvent (acetonitrile, N,N-dimethylformamide (DMF), or N-methylpyrrolidone (NMP)), and a mixed solvent of any of a "mixed solution of water and sodium carbonate", a "mixed solution of water and potassium carbonate" and a "mixed solution of water and sodium chloride", and a hydrophilic organic solvent (acetonitrile, N,N-dimethylformamide (DMF), or N-methylpyrrolidone (NMP)) are preferred.

As the concentration condition, 2- to 100-fold dilution with respect to the substrate (N-unprotected C-protected peptide) is preferable.

Regarding washing, suitable conditions can be selected as appropriate with respect to the mixing method and washing time. Washing in basic is preferable.

In this step, in order to enhance the washing effect, washing can be performed plural times (e.g., twice). For example, as the first washing, the washing can be performed with a basic solvent such as an aqueous sodium carbonate solution, and then as the second washing, the washing can be performed with a neutral solvent such as brine. Those of ordinary skill in the art can appropriately select the washing conditions such as the number of washings, washing solvent, and the like according to the kind of the peptide produced, the kind of the reagent used, and the like.

It is preferable to perform a base treatment after the removal of the Fmoc group, the removal of the Boc group or the removal of the Cbz group because the condensation reaction in the next step proceeds easily. The base treatment only needs to liberate the N-terminal amino group of the peptide, and specific examples thereof include washing with an aqueous sodium carbonate solution or an organic base.

Examples of the oil-water separation means include a continuous layer separation means having a structure including a filter and a Gravity type continuous layer separation means. Here, any filter can be selected as appropriate, and examples thereof include means having a constitution including a filter such as a membrane filter and the like. For example, a liquid-liquid separator system of Zaiput Flow Technologies can be used. The Gravity type continuous layer separation means is a layer separation means using gravity, which is a continuous separatory funnel, and includes a means of gradually draining the liquid from the separated bottom layer and the top layer. Means including a Gravity Settler, means including an inclined plate, and the like can also be mentioned. For example, Lamella Gravity Settler of Parkson, and the like can be mentioned.

When the flow reactor in step (B) is used, suitable conditions can be selected as appropriate for the mixing conditions, flow (flow rate), and temperature control conditions of each solution. Unlimitatively, conditions under which a slug flow (flow in which organic layer and aqueous layer are alternately repeated) is formed after introduction of a reaction mixture containing N-unprotected C-protected peptide, and water and/or a hydrophilic organic solvent into a flow reactor are particularly preferred. The conditions can be appropriately determined by those of ordinary skill in the art.

Using the N-unprotected C-protected peptide obtained in step (B) as the "C-protected peptide in which the C-terminal is protected by a protecting group, a side chain functional group is optionally further protected by a protecting group, and at least one of the protecting groups is a pseudo-solid-phase protecting group (C-protected peptide)" in step (1), the cycle of steps (1), (A), (2) and (B) in the present invention is performed repeatedly as appropriate, whereby the peptide chain thereof can be elongated. When the N-unprotected C-protected peptide obtained in step (B) has a desired peptide sequence, a peptide as the final product can be obtained by further removing the C-protecting group and the protecting group of the side chain functional group. Both of these embodiments are encompassed in the scope of the present invention. This deprotection step can be appropriately performed by referring to a method known per se or a method for removing protecting groups described in the present specification.

When the present invention is applied, there is no particular upper limit to the desired peptide chain length (number of amino acid residues). Such number of amino acid residues is preferably not more than 100, more preferably not more than 50, further preferably not more than 30, particularly preferably not more than 20. While there is no particular lower limit, such number of amino acid residues is preferably not less than 5, more preferably not less than 6.

In the above, each embodiment of the steps (1), (A), (2), and (B) of the present invention has been described in detail. Steps (1), (A), (2), and (B) can be performed continuously (in a continuous flow) using a flow reactor. Such embodiment is one of the preferred embodiments. It is not always necessary to perform step (1)→step (A)→step (2)→step (B) in this order, and it is also possible to start from an intermediate step (e.g., step (2)) as appropriate depending on the starting material compound to be used. In this case, the starting material compound may be obtained, for example, by batch synthesis, and may not necessarily be obtained by performing the steps of the present invention. Such other embodiment is also encompassed in the scope of the present invention.

Removal of Pseudo-Solid-Phase Protecting Group

Removal of the pseudo-solid-phase protecting group is performed after the above-mentioned step (A) or the above-mentioned step (B). As a result, the final object product peptide wherein the C-terminal of the peptide is —COOH (e.g., the aforementioned formula (I) or the formula (II) wherein Y is a hydroxy group or a halogen atom), or —CONHR (e.g., the aforementioned formula (I) or the formula (II) wherein Y is an NHR group) can be obtained.

Among the pseudo-solid-phase protecting groups described in JP-A-2000-44493, WO 2006/104166, WO 2007/034812, WO 2007/122847, WO 2010/113939, WO 2010/104169, WO 2011/078295, WO 2012/029794, WO 2016/140232, WO 2003/018188, WO 2017/038650, WO 2019/009317, all of which are incorporated herein by reference in their entireties, and the like, a 2,4-O-alkyl type or 2,4,6-O-alkyl type pseudo-solid-phase protecting group permits selective removal of the pseudo-solid-phase protecting group alone.

As the reagent to be used for the selective deprotection of the pseudo-solid-phase protecting group, acid (e.g., trifluoroacetic acid (hereinafter to be referred to as TFA), hydrochloric acid, sulfuric acid, methanesulfonic acid, p-toluenesulfonic acid), fluorine-substituted alcohol (e.g., trifluoroethanol (hereinafter to be referred to as TFE), hexafluoroisopropanol (hereinafter to be referred to as HFIP), and the like can be mentioned. Of these, TFA, TFE, or HFIP is preferred. As a solvent to be used for the deprotection, for example, chloroform, dichloromethane, 1,2-dichloroethane or a mixed solvent thereof and the like can be mentioned. The concentration of the acid to be used for the deprotection of the pseudo-solid-phase protecting group is, for example, 0.1w/v % to 5w/v %, which is a weak acid treatment, and the concentration of the fluorine-substituted alcohol to be used for the deprotection of the pseudo-solid-phase protecting group is, for example, 10w/v % to 100w/v %.

On the other hand, it is also possible to remove a pseudo-solid-phase protecting group derived from an aromatic compound of the aforementioned formula (I) or the aforementioned formula (II), wherein Y is a hydroxy group, an —NHR group, or a halogen atom (compound having a pseudo-solid-phase protecting group) simultaneously with the protecting group of other side chain in a peptide. In this case, a conventional method used in the field, particularly peptide synthesis, is used, and a method including adding an acid and the like is preferably used. As the acid, TFA, hydrochloric acid, sulfuric acid, methanesulfonic acid, p-toluenesulfonic acid, and the like are used. Of these, TFA is particularly preferable. The amount of the acid to be used is appropriately set according to the kind of the acid to be used, and an amount suitable for removing the pseudo-solid-phase protecting group is used. The amount of the acid to be used is preferably not less than 3 mol, more preferably not less than 5 mol, preferably not more than 100 mol, more preferably not more than 50 mol, per 1 mol of the N-protected C-protected peptide or N-unprotected C-protected peptide. Along with such use, trifluoromethanesulfonic acid, trimethylsilyl trifluoromethanesulfonate, BF$_3$.etherate and the like can also be added as a further source of strong acid.

The protecting groups of the side chain functional group can be appropriately removed according to the kind thereof by a method generally performed in the pertinent technical field, or according to the deprotection method of the protecting groups described in the present specification.

While the reaction temperature is not particularly limited as long as the reaction proceeds, it is preferably 0° C. to 50° C., more preferably 0° C. to 30° C. The reaction time is, for example, 0.5 to 24 hr.

Independent Utilization of Step (A)/Step (B)

The present invention provides a method for producing a peptide, including performing steps (1), (A), (2), and (B) described in detail in the above. Where necessary, a condensation step corresponding to step (1) and a deprotection step corresponding to step (2) are performed under conventional conditions for a batch method, and then the reaction mixture containing the obtained resultant product is subjected to a purification/partitioning step according to the methods of step (A) and step (B) of the present invention, whereby the N-protected C-protected peptide or N-unprotected C-protected peptide can be efficiently purified and isolated and can be efficiently applied to other reaction steps. Such production method of peptide including independently utilizing the step (A) and/or step (B) of the present invention is also encompassed in the scope of the present invention.

Other features of the invention will become apparent in the course of the following descriptions of exemplary embodiments which are given for illustration of the invention and are not intended to be limiting thereof.

EXAMPLES

The reagents, apparatuses and materials used in the present invention are commercially available unless otherwise specified. In the present specification, when amino acid and the like are indicated by abbreviations, each indication is based on the abbreviation of the IUPAC-IUB Commission on Biochemical Nomenclature or conventional abbreviations in the art.

Production Example 1: Reaction with Pseudo-Solid-Phase Protecting Group

Using Fmoc-Leu-OH as a starting material, and 4',4'-bis (2,3-dihydrophytyloxy)phenyl)methylamine (hereinafter denoted as $NH_2$-Dpm(OPhy)) as a pseudo-solid-phase protecting group, and according to a conventional method (WO 2010/113939, WO 2012/029794, which are incorporated herein by reference in their entireties), Fmoc-Leu-NH-Dpm (OPhy) was synthesized, and further, a removal reaction of Fmoc was performed using a base to give H-Leu-NH-Dpm (OPhy).

Example 1

Synthesis of 2-residue peptide (H-Tyr(tBu)-Leu-NH-Dpm(OPhy))

apparatus used (flow reactor, mixer, pump, oil-water separation means)

flow reactor: PFA/PTFE tube (inner diameter 1.0 mm or 1.6 mm) [Swagelok Company]

mixer: T-shaped mixer Union Tee SS-100-3 (outer diameter 1/16 inch) or SS-200-3 (outer diameter 1/8 inch) [Swagelok Company]

pump: plunger pump YMCU-22 [YMC CO., LTD.], syringe pump YSP-301 [YMC CO., LTD.], or Diaphragm pump Q-10-6T-P-M49 [TACMINA CORPORATION]

oil-water separation membrane apparatus: SEP-10 [Zaiput Flow Technologies]

oil-water separation membrane: OB-2000-S-10 (hydrophobic membrane with pore size 1.0 μm) [Zaiput Flow Technologies]

Step (1): Condensation Reaction

A chloroform solution (solution-1) containing 0.10 mmol/ml of H-Leu-NH-Dpm(OPhy) obtained in Production Example 1, and a dimethylformamide (DMF) solution (solution-2) containing 0.11 mmol/ml of Fmoc-Tyr(tBu)-OH and 0.04 mmol/ml of 1-hydroxybenzotriazole (HOBt) anhydride were fed using a pump (plunger pump YMCU-22 (may be syringe pump YSP-301 or Diaphragm pump Q-10-6T-P-M49)) each at a flow rate of 0.20 ml/min, and mixed using a T-shaped mixer (Union Tee SS-100-3; outer diameter 1/16 inch). A chloroform solution (solution-3) containing 0.05 mmol/ml of N-ethyl-N'-3-dimethylaminopropylcarbodiimide hydrochloride (EDC.HCl) was fed at a flow rate of 0.40 ml/min, mixed with the mixed solution of solutions-1, 2 by a T-shaped mixer (Union Tee SS-100-3; outer diameter 1/16 inch) and reacted in a PFA tube (inner diameter 1.0 mm, length 10 m) for 10 min to give an Fmoc-Tyr(tBu)-Leu-NH-Dpm(OPhy) solution.

Step (A): Extraction After Condensation Reaction

The Fmoc-Tyr(tBu)-Leu-NH-Dpm(OPhy) solution obtained in the above-mentioned step (1) was fed at a flow rate of 0.25 ml/min, and 20 wt % NaCl aqueous solution was fed at a flow rate of 0.17 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm, length 2 m) for 10 min. The EDC.HCl remaining in the condensation reaction was deactivated and removed into the aqueous layer, and then separated using an oil-water separation membrane (OB-2000-S-10; hydrophobic membrane with pore size 1.0 μm), and the permeated organic layer was recovered.

Step (2): Removal Reaction of Fmoc

An organic layer (solution-1) containing 0.10 mmol/ml of Fmoc-Tyr(tBu)-Leu-NH-Dpm(OPhy) obtained in the above-mentioned step (A) was fed at a flow rate of 0.56 ml/min, and a DMF solution (solution-2) containing 1.10 mmol/ml of thiomalic acid and 3.30 mmol/ml of 1,8-diazabicyclo [5.4.0]-7-undecene (DBU) was fed at a flow rate 0.20 ml/min each using a pump, and mixed using a T-shaped mixer (Union Tee SS-100-3; outer diameter 1/16 inch). The solution after mixing was reacted in a PFA tube (inner diameter 1.0 mm, length 10 m) for 10 min to give an H-Tyr(tBu)-Leu-NH-Dpm(OPhy) solution. Dibenzofulvene (DBF) generated during the reaction was reacted with thiomalic acid to convert same into a fulvene adduct.

Step (B)-1: Washing with Aqueous Sodium Carbonate Solution After Removal Reaction of Fmoc A chloroform solution (solution-1) containing 0.10 mmol/ml of H-Tyr(tBu)-Leu-NH-Dpm(OPhy) obtained in the above-mentioned step (2) was fed at a flow rate of 0.34 ml/min, and a 5.0 wt % $Na_2CO_3$ aqueous solution (solution-2) containing 0.33 mmol/ml of acetic acid was fed at a flow rate of 0.37 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm, length 2 m) for 6 min. The fulvene adduct produced during the removal reaction of Fmoc was removed into the aqueous layer, and then separated using an oil-water separation membrane (OB-2000-S-10; hydrophobic membrane with pore size 1.0 μm), and the permeated organic layer was recovered.

Step (B)-2: Washing with Aqueous Sodium Chloride Solution After Washing with Aqueous Sodium Carbonate Solution The H-Tyr(tBu)-Leu-NH-Dpm(OPhy) solution (solution-1) obtained in the above-mentioned step (B)-1 was fed at a flow rate of 0.40 ml/min, and 20 wt % NaCl aqueous solution (solution-2) was fed at a flow rate of 0.27 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm, length 2 m) for 6 min. The fulvene adduct that could not be completely removed in the above-mentioned step (B)-1 was removed into the aqueous layer, and then separated using an oil-water separation membrane (OB-2000-S-10; hydrophobic membrane with pore size 1.0 μm), and the permeated organic layer was recovered.

Example 2

Synthesis of 6-residue peptide (H-Ile-Pro-Glu(OtBu)-Glu(OtBu)-Tyr(tBu)-Leu-NH-Dpm(OPhy))

apparatus used (flow microreactor, coil tube reactor, tube, mixer, oil-water separation means)

flow microreactor: R2 Plus [Vapourtec Ltd.]

coil tube reactor: coil tube reactor (PFA material, outer diameter ⅛ inch, inner diameter 1/16 inch, volume 5 ml or 10 ml) [Vapourtec Ltd.] or coil tube reactor (PFA material, outer diameter ⅛ inch, inner diameter 1/16 inch, volume 5 ml or 10 ml) [Idex]

tube: tube (PFA material, outer diameter ⅛ inch, inner diameter 0.020 inch) [Idex] or tube (PFA material, outer diameter ⅛ inch, inner diameter 1/16 inch) [Idex]

mixer: T-shaped mixer (ETFE (copolymer of ethylene and tetrafluoroethylene) material, inner diameter 0.020 inch) [Idex], cross-shaped mixer (ETFE material, inner diameter 0.020 inch) [Idex], or T-shaped mixer (stainless material, outer diameter ⅛ inch) [Swagelok Company]

oil-water separation membrane apparatus: SEP-10 [Zaiput Flow Technologies]

oil-water separation membrane: hydrophobic membrane with pore size 1.0 μm or 0.5 μm [Zaiput Flow Technologies]

Step (2): Removal Reaction of Fmoc

Fmoc-Leu-NH-Dpm(OPhy) (2.2 g) obtained in Production Example 1 was dissolved in chloroform (37 ml) and the solution was introduced at a flow rate of 0.83 ml/min from one inlet of a T-shaped mixer (manufactured by Idex, ETFE material, inner diameter 0.020 inch). Simultaneously therewith, a solution obtained by dissolving DBU and thiomalic acid in DMF (2.4 mol/l, 0.79 mol/l, respectively) was introduced at a flow rate of 0.28 ml/min from the other inlet of the T-shaped mixer, and the two solutions were mixed at room temperature. The mixture was passed through a coil tube reactor (manufactured by Vaportec, PFA material, volume 10 ml) at room temperature from the outlet of the T-shaped mixer to perform a removal reaction of Fmoc. The reaction mixture was introduced from the outlet of the coil tube reactor into one inlet of the next T-shaped mixer (manufactured by Idex, ETFE material, inner diameter 0.020 inch). Simultaneously therewith, a solution of acetic acid in chloroform (2.1 mol/l) was introduced at a flow rate of 0.093 ml/min from the other inlet, and the two solutions were mixed at room temperature. The mixture was passed through a coil tube reactor (manufactured by Vaportec, PFA material, volume 5 ml) at room temperature from the outlet of the T-shaped mixer to quench the removal reaction of Fmoc.

Step (B)-1: Washing with Aqueous Sodium Carbonate Solution After Removal Reaction of Fmoc The quenched mixture obtained in the above-mentioned step (2) was introduced from the outlet of the coil tube reactor into one inlet of a T-shaped mixer (manufactured by Swagelok, stainless material, outer diameter ⅛ inch). Simultaneously therewith, a 7.5 w/w % Na₂CO₃ solution was introduced at a flow rate of 0.80 ml/min from the other inlet, and the two solutions were mixed at room temperature. The mixture was passed through a coil tube reactor (manufactured by Idex, PFA material, outer diameter 1/16 inch, inner diameter 0.020 inch, volume 10 ml) at room temperature from the outlet of the T-shaped mixer to perform a washing operation. A partitioning apparatus in which a hydrophobic membrane (pore size 1.0 μm) manufactured by Zaiput was provided in SEP-10 manufactured by Zaiput was set at the outlet of the coil tube reactor, and the washed mixture was passed therethrough. The solution discharged from the partitioning apparatus was separated into an organic layer and an aqueous layer, and the aqueous layer was collected in a measuring cylinder (54 ml).

Step (B)-2: Washing with Aqueous Sodium Chloride Solution After Washing with Aqueous Sodium Carbonate Solution The organic layer obtained in the above-mentioned step (B)-1 was introduced into one inlet of a T-shaped mixer (manufactured by Swagelok, stainless material, outer diameter ⅛ inch). A solution of 20 w/w % NaCl aqueous solution in DMF at a mixing ratio of 6:4 was introduced at a flow rate of 0.88 ml/min from the other inlet of the T-shaped mixer, and the two solutions were mixed at room temperature. The mixture was passed through a coil tube reactor (manufactured by Idex, PFA material, outer diameter 1/16 inch, inner diameter 0.020 inch, volume 5 ml) at room temperature from the outlet of the T-shaped mixer to perform a washing operation. A partitioning apparatus in which a hydrophobic membrane (pore size 0.5 μm) manufactured by Zaiput was provided in SEP-10 manufactured by Zaiput was set at the outlet of the coil tube reactor, and the washed mixture was passed therethrough. The solution discharged from the partitioning apparatus was separated into an organic layer and an aqueous layer. Each layer was collected in a measuring cylinder, and 68 ml of the organic layer containing H-Leu-NH-Dpm(OPhy) and 46 ml of the aqueous layer were obtained.

Step (1): Condensation Reaction

The H-Leu-NH-Dpm(OPhy) organic layer (25 ml) obtained in the above-mentioned step (B)-2 was introduced at a flow rate of 0.68 ml/min into one inlet of a cross-shaped mixer (manufactured by Idex, ETFE material, inner diameter 0.020 inch). Simultaneously therewith, a solution obtained by dissolving Fmoc-Tyr(tBu)-OH and HOBt in DMF (0.50 mol/l, 0.10 mol/l, respectively) was introduced at a flow rate of 0.65 ml/min from the other inlet, a solution of EDC.HCl in chloroform (0.033 mol/l) was introduced at a flow rate of 0.042 ml/min from the remaining other inlet, and the three solutions were mixed at room temperature. The mixture was passed through a coil tube reactor (manufactured by Vaportec, PFA material, volume 10 ml) heated to 40° C. from the outlet of the cross-shaped mixer to perform a condensation reaction.

Step (A): Extraction After Condensation Reaction

The reaction mixture obtained in the above-mentioned step (1) was introduced from the outlet of the coil tube reactor into one inlet of the next T-shaped mixer (manufactured by Idex, ETFE material, inner diameter 0.020 inch). Simultaneously therewith, a 20 w/w % NaCl aqueous solution was introduced at a flow rate of 0.12 ml/min from the other inlet, and the two solutions were mixed at room temperature. The mixture was passed through a coil tube reactor (manufactured by Vaportec, PFA material, volume 5 ml) at room temperature from the outlet of the T-shaped mixer to perform a washing operation. A partitioning apparatus in which a hydrophobic membrane (pore size 1.0 μm) manufactured by Zaiput was provided in SEP-10 manufactured by Zaiput was set at the outlet of the coil tube reactor, and the washed mixture was passed therethrough. The solution discharged from the partitioning apparatus was separated into an organic layer and an aqueous layer. Each layer was collected in a measuring cylinder, and 44 ml of the organic layer containing Fmoc-Tyr(tBu)-Leu-NH-Dpm(OPhy) and 45 ml of the aqueous layer were obtained.

Fmoc-Tyr(tBu)-Leu-NH-Dpm(OPhy) obtained above was further subjected to step (2) of the removal reaction of Fmoc and step (B)-1, step (B)-2 to obtain H-Tyr(tBu)-Leu-NH-Dpm(OPhy). The above-mentioned steps (1), (A), (2), (B)-1 and (B)-2 were repeated, during which Fmoc-Glu(OtBu)-OH, Fmoc-Glu(OtBu)-OH, Fmoc-Pro-OH, and Fmoc-Ile-OH were sequentially used as N-protected amino acid to give a protected peptide, H-Ile-Pro-Glu(OtBu)-Glu(OtBu)-Tyr(tBu)-Leu-NH-Dpm(OPhy).

LC/MS M$^+$ m/z 1688.3

Example 3

Synthesis of 5-residue peptide (H-Glu(OtBu)-Ala-Glu(OtBu)-Lys(Boc)-Leu-NH-Dpm(OPhy))

apparatus used (flow reactor, mixer, pump, oil-water separation means)

The same apparatus as in Example 1 was used.

Step (1): Condensation Reaction (2-Residue Peptide)

A chloroform solution (solution-1) containing 0.10 mmol/ml of H-Leu-NH-Dpm(OPhy) obtained in Production Example 1, and a dimethylformamide (DMF) solution (solution-2) containing 0.35 mmol/ml of Fmoc-Lys(Boc)-OH and 0.09 mmol/ml of 1-hydroxybenzotriazole (HOBt)anhydride were fed using a pump (plunger pump YMCU-22 (may be syringe pump YSP-301 or Diaphragm pump Q-10-6T-P-M49)) at flow rates of 0.50 ml/min and 0.21 ml/min, respectively, and mixed using a T-shaped mixer (Union Tee SS-100-3; outer diameter 1/16 inch). A chloroform solution (solution-3) containing 0.54 mmol/ml of N-ethyl-N'-3-dimethylaminopropylcarbodiimide hydrochloride (EDC.HCl) was fed at a flow rate of 0.13 ml/min, mixed with the mixed solution of solutions-1, 2 by a T-shaped mixer (Union Tee SS-100-3; outer diameter 1/16 inch) and reacted in a PFA tube (inner diameter 1.0 mm) to give an Fmoc-Lys(Boc)-Leu-NH-Dpm(OPhy) solution.

Step (A): Extraction After Condensation Reaction (2-Residue Peptide)

The Fmoc-Lys(Boc)-Leu-NH-Dpm(OPhy) solution obtained in the above-mentioned step (1) was fed at a flow rate of 0.84 ml/min, and 20 wt % NaCl aqueous solution was fed at a flow rate of 0.56 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm). The N-ethyl-N'-3-dimethylaminopropylcarbodiimide hydrochloride (EDC.HCl) remaining in the condensation reaction was deactivated and removed into the aqueous layer, and then separated using an oil-water separation membrane (OB-2000-S-10; hydrophobic membrane with pore size 1.0 μm), and the permeated organic layer was recovered.

Step (2): Removal Reaction of Fmoc (2-Residue Peptide)

An organic layer (solution-1) containing 0.06 mmol/ml of Fmoc-Lys(Boc)-Leu-NH-Dpm(OPhy) obtained in the above-mentioned step (A) was fed at a flow rate of 0.73 ml/min, and a DMF solution (solution-2) containing 0.67 mmol/ml of thiomalic acid and 2.02 mmol/ml of 1,8-diazabicyclo[5.4.0]-7-undecene (DBU) was fed at a flow rate 0.35 ml/min each using a pump, and mixed using a T-shaped mixer (Union Tee SS-100-3; outer diameter 1/16 inch). The solution after mixing was reacted in a PFA tube (inner diameter 1.0 mm) to give an H-Lys(Boc)-Leu-NH-Dpm(OPhy) solution.

Step (B)-1: Washing with Aqueous Sodium Carbonate Solution After Removal Reaction of Fmoc (2-Residue Peptide)

A chloroform solution (solution-1) containing H-Lys(Boc)-Leu-NH-Dpm(OPhy) obtained in the above-mentioned step (2) was fed at a flow rate of 1.08 ml/min, and a 5.0 wt % Na$_2$CO$_3$ aqueous solution (solution-2) containing 0.26 mmol/ml of acetic acid was fed at a flow rate of 0.80 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm). The fulvene adduct produced during the removal reaction of Fmoc was removed into the aqueous layer, and then separated using an oil-water separation membrane (OB-2000-S-10; hydrophobic membrane with pore size 1.0 μm), and the permeated organic layer was recovered.

Step (B)-2: Washing with Aqueous Sodium Chloride Solution After Washing with Aqueous Sodium Carbonate Solution (2-Residue Peptide)

The H-Lys(Boc)-Leu-NH-Dpm(OPhy) solution obtained in the above-mentioned step (B)-1 was fed at a flow rate of 1.08 ml/min, and 20 wt % NaCl aqueous solution (solution-2) was fed at a flow rate of 0.88 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm). The fulvene adduct that could not be completely removed in the above-mentioned step (B)-1 was removed into the aqueous layer, and then separated using an oil-water separation membrane (OB-2000-S-10; hydrophobic membrane with pore size 1.0 μm), and the permeated organic layer was recovered.

Step (1): Condensation Reaction (3-Residue Peptide)

A chloroform solution (solution-1) containing 0.05 mmol/ml of H-Lys(Boc)-Leu-NH-Dpm(OPhy) obtained in the above-mentioned step (B)-2, and a dimethylformamide (DMF) solution (solution-2) containing 0.18 mmol/ml of Fmoc-Glu(OtBu)-OH and 0.05 mmol/ml of 1-hydroxybenzotriazole (HOBt)anhydride were fed using a pump (plunger pump YMCU-22 (may be syringe pump YSP-301 or Diaphragm pump Q-10-6T-P-M49)) at a flow rate of 0.50 ml/min, 0.21 ml/min, respectively, and mixed using a T-shaped mixer (Union Tee SS-100-3; outer diameter 1/16 inch). A chloroform solution (solution-3) containing 0.27 mmol/ml of N-ethyl-N'-3-dimethylaminopropylcarbodiimide hydrochloride (EDC.HCl) was fed at a flow rate of 0.13 ml/min, mixed with the mixed solution of solutions-1, 2 by a T-shaped mixer (Union Tee SS-100-3; outer diameter 1/16 inch) and reacted in a PFA tube (inner diameter 1.0 mm) to give an Fmoc-Glu(OtBu)-Lys(Boc)-Leu-NH-Dpm(OPhy) solution.

Step (A): Extraction After Condensation Reaction (3-Residue Peptide)

The Fmoc-Glu(OtBu)-Lys(Boc)-Leu-NH-Dpm(OPhy) solution obtained in the above-mentioned step (1) was fed at a flow rate of 0.84 ml/min, and 20 wt % NaCl aqueous solution was fed at a flow rate of 0.56 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm). The EDC.HCl remaining in the condensation reaction was deactivated and removed into the aqueous layer, and then separated using an oil-water separation membrane (OB-2000-S-10; hydrophobic membrane with pore size 1.0 μm), and the permeated organic layer was recovered.

Step (2): Removal Reaction of Fmoc (3-Residue Peptide)

An organic layer (solution-1) containing 0.03 mmol/ml of Fmoc-Glu(OtBu)-Lys(Boc)-Leu-NH-Dpm(OPhy) obtained in the above-mentioned step (A) was fed at a flow rate of 0.73 ml/min, and a DMF solution (solution-2) containing 0.26 mmol/ml of thiomalic acid and 0.79 mmol/ml of 1,8-diazabicyclo[5.4.0]-7-undecene (DBU) was fed at a flow rate 0.35 ml/min each using a pump, and mixed using a T-shaped mixer (Union Tee SS-100-3; outer diameter 1/16 inch). The solution after mixing was reacted in a PFA tube (inner diameter 1.0 mm) to give an H-Glu(OtBu)-Lys(Boc)-Leu-NH-Dpm(OPhy) solution.

Step (B)-1: Washing with Aqueous Sodium Carbonate Solution After Removal Reaction of Fmoc (3-Residue Peptide)

A chloroform solution (solution-1) containing H-Glu(OtBu)-Lys(Boc)-Leu-NH-Dpm(OPhy) obtained in the above-mentioned step (2) was fed at a flow rate of 1.08 ml/min, and a 5.0 wt % $Na_2CO_3$ aqueous solution (solution-2) containing 0.10 mmol/ml of acetic acid was fed at a flow rate of 0.80 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm). The fulvene adduct produced during the removal reaction of Fmoc was removed into the aqueous layer, and then separated using an oil-water separation membrane (OB-2000-S-10; hydrophobic membrane with pore size 1.0 μm), and the permeated organic layer was recovered.

Step (B)-2: Washing with Aqueous Sodium Chloride Solution After Washing with Aqueous Sodium Carbonate Solution (3-Residue Peptide)

The H-Glu(OtBu)-Lys(Boc)-Leu-NH-Dpm(OPhy) solution (solution-1) obtained in the above-mentioned step (B)-1 was fed at a flow rate of 1.08 ml/min, and 20 wt % NaCl aqueous solution (solution-2) was fed at a flow rate of 0.88 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm). The fulvene adduct that could not be completely removed in the above-mentioned step (B)-1 was removed into the aqueous layer, and then separated using an oil-water separation membrane (OB-2000-S-10; hydrophobic membrane with pore size 1.0 μm), and the permeated organic layer was recovered to obtain the following. H-Glu(OtBu)-Lys(Boc)-Leu-NH-Dpm(OPhy)

LC-MS M$^+$ m/z 1303.3

Step (1): Condensation Reaction (4-Residue Peptide)

A chloroform solution (solution-1) containing 0.04 mmol/ml of H-Glu(OtBu)-Lys(Boc)-Leu-NH-Dpm(OPhy) obtained in the above-mentioned step (B)-2, and a dimethylformamide (DMF) solution (solution-2) containing 0.15 mmol/ml of Fmoc-Ala-OH.H$_2$O and 0.04 mmol/ml of 1-hydroxybenzotriazole (HOBt)anhydride were fed using a pump (plunger pump YMCU-22 (may be syringe pump YSP-301 or Diaphragm pump Q-10-6T-P-M49)) at a flow rate of 0.50 ml/min,0.21 ml/min, respectively, and mixed using a T-shaped mixer (Union Tee SS-100-3; outer diameter 1/16 inch). A chloroform solution (solution-3) containing 0.23 mmol/ml of N-ethyl-N'-3-dimethylaminopropylcarbodiimide hydrochloride (EDC.HCl) was fed at a flow rate of 0.13 ml/min, mixed with the mixed solution of solutions-1, 2 by a T-shaped mixer (Union Tee SS-100-3; outer diameter 1/16 inch) and reacted in a PFA tube (inner diameter 1.0 mm) to give an Fmoc-Ala-Glu(OtBu)-Lys(Boc)-Leu-NH-Dpm(OPhy) solution.

Step (A): Extraction After Condensation Reaction (4-Residue Peptide)

The Fmoc-Ala-Glu(OtBu)-Lys(Boc)-Leu-NH-Dpm(OPhy) solution obtained in the above-mentioned step (1) was fed at a flow rate of 0.84 ml/min, and 20 wt % NaCl aqueous solution was fed at a flow rate of 0.56 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm). The EDC.HCl remaining in the condensation reaction was deactivated and removed into the aqueous layer, and then separated using an oil-water separation membrane (OB-2000-S-10; hydrophobic membrane with pore size 1.0 μm), and the permeated organic layer was recovered.

Step (2): Removal Reaction of Fmoc (4-Residue Peptide)

An organic layer (solution-1) containing 0.03 mmol/ml of Fmoc-Ala-Glu(OtBu)-Lys(Boc)-Leu-NH-Dpm(OPhy) obtained in the above-mentioned step (A) was fed at a flow rate of 0.73 ml/min, and a DMF solution (solution-2) containing 0.27 mmol/ml of thiomalic acid and 0.82 mmol/ml of 1,8-diazabicyclo[5.4.0]-7-undecene (DBU) was fed at a flow rate 0.35 ml/min each using a pump, and mixed using a T-shaped mixer (Union Tee SS-100-3; outer diameter 1/16 inch). The solution after mixing was reacted in a PFA tube (inner diameter 1.0 mm) to give an H-Ala-Glu(OtBu)-Lys(Boc)-Leu-NH-Dpm(OPhy) solution.

Step (B)-1: Washing with Aqueous Sodium Carbonate Solution After Removal Reaction of Fmoc (4-Residue Peptide)

A chloroform solution (solution-1) containing H-Ala-Glu(OtBu)-Lys(Boc)-Leu-NH-Dpm(OPhy) obtained in the above-mentioned step (2) was fed at a flow rate of 1.08 ml/min, and a 5.0 wt % $Na_2CO_3$ aqueous solution (solution-2) containing 0.11 mmol/ml of acetic acid was fed at a flow rate of 0.80 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm). The fulvene adduct produced during the removal reaction of Fmoc was removed into the aqueous layer, and then separated using an oil-water separation membrane (OB-2000-S-10; hydrophobic membrane with pore size 1.0 μm), and the permeated organic layer was recovered.

Step (B)-2: Washing with Aqueous Sodium Chloride Solution After Washing with Aqueous Sodium Carbonate Solution (4-Residue Peptide)

The H-Ala-Glu(OtBu)-Lys(Boc)-Leu-NH-Dpm(OPhy) solution (solution-1) obtained in the above-mentioned step (B)-1 was fed at a flow rate of 1.08 ml/min, and 20 wt % NaCl aqueous solution (solution-2) was fed at a flow rate of 0.88 ml/min each using a pump, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm). The fulvene adduct that could not be completely removed in the above-mentioned step (B)-1 was removed into the aqueous layer, and then separated using an oil-water separation membrane (OB-2000-S-10; hydrophobic membrane with pore size 1.0 μm), and the permeated organic layer was recovered to obtain the following. H-Ala-Glu(OtBu)-Lys(Boc)-Leu-NH-Dpm(OPhy)

LC-MS M$^+$ m/z 1374.4

Step (1): Condensation Reaction (5-Residue Peptide)

A chloroform solution (solution-1) containing 0.02 mmol/ml of H-Ala-Glu(OtBu)-Lys(Boc)-Leu-NH-Dpm(OPhy) obtained in the above-mentioned step (B)-2, and a dimethylformamide (DMF) solution (solution-2) containing 0.06 mmol/ml of Fmoc-Glu(OtBu)-OH and 0.02 mmol/ml of 1-hydroxybenzotriazole (HOBt)anhydride were fed using a pump (plunger pump YMCU-22 (may be syringe pump YSP-301 or Diaphragm pump Q-10-6T-P-M49)) at a flow rate of 0.50 ml/min,0.21 ml/min, respectively, and mixed using a T-shaped mixer (Union Tee SS-100-3; outer diameter ¹⁄₁₆ inch). A chloroform solution (solution-3) containing 0.10 mmol/ml of N-ethyl-N'-3-dimethylaminopropylcarbodiimide hydrochloride (EDC.HCl) was fed at a flow rate of 0.13 ml/min, mixed with the mixed solution of solutions-1, 2 by a T-shaped mixer (Union Tee SS-100-3; outer diameter ¹⁄₁₆ inch) and reacted in a PFA tube (inner diameter 1.0 mm) to give an Fmoc-Glu(OtBu)-Ala-Glu(OtBu)-Lys(Boc)-Leu-NH-Dpm(OPhy) solution.

Step (A): Extraction After Condensation Reaction (5-Residue Peptide)

The Fmoc-Glu(OtBu)-Ala-Glu(OtBu)-Lys(Boc)-Leu-NH-Dpm(OPhy) solution obtained in the above-mentioned step (1) was fed at a flow rate of 0.84 ml/min, and 20 wt % NaCl aqueous solution was fed at a flow rate of 0.56 ml/min each using a pump, and merged using a T-shaped mixer (Union Tee SS-200-3; outer diameter ⅛ inch). After merging, the solution that became a slug flow (flow in which the organic layer and the aqueous layer are alternately repeated) was passed through a PFA tube (inner diameter 1.6 mm). The EDC.HCl remaining in the condensation reaction was deactivated and removed into the aqueous layer, and then separated using an oil-water separation membrane (OB-2000-S-10; hydrophobic membrane with pore size 1.0 μm), and the permeated organic layer was recovered.

Step (2): Removal Reaction of Fmoc (5-Residue Peptide)

An organic layer (solution-1) containing 0.10 mmol/ml of Fmoc-Glu(OtBu)-Ala-Glu(OtBu)-Lys(Boc)-Leu-NH-Dpm (OPhy) obtained in the above-mentioned step (A) was fed at a flow rate of 0.73 ml/min, and a DMF solution (solution-2) containing 0.08 mmol/ml of thiomalic acid and 0.25 mmol/ml of 1,8-diazabicyclo[5.4.0]-7-undecene (DBU) was fed at a flow rate 0.35 ml/min each using a pump, and mixed using a T-shaped mixer (Union Tee SS-100-3; outer diameter ¹⁄₁₆ inch). The solution after mixing was reacted in a PFA tube (inner diameter 1.0 mm) to give an H-Glu(OtBu)-Ala-Glu (OtBu)-Lys(Boc)-Leu-NH-Dpm(OPhy) solution.

Step (B)-1: Washing with Aqueous Sodium Carbonate Solution After Removal Reaction of Fmoc (5-Residue Peptide)

A chloroform solution (solution-1) containing H-Glu (OtBu)-Ala-Glu(OtBu)-Lys(Boc)-Leu-NH-Dpm(OPhy) obtained in the above-mentioned step (2) was fed at a flow rate of 1.08 ml/min, and a 5.0 wt % Na$_2$CO$_3$ aqueous solution (solution-2) containing 0.03 mmol/ml of acetic acid was fed at a flow rate of 0.80 ml/min each using a pump, and merged using a T-shaped mixer (Union Tee SS-200-3; outer diameter ⅛ inch). After merging, the solution that became a slug flow (flow in which the organic layer and the aqueous layer are alternately repeated) was passed through a PFA tube (inner diameter 1.6 mm). The fulvene adduct produced during the removal reaction of Fmoc was removed into the aqueous layer, and then separated using an oil-water separation membrane (OB-2000-S-10; hydrophobic membrane with pore size 1.0 μm), and the permeated organic layer was recovered.

Step (B)-2: Washing with Aqueous Sodium Chloride Solution After Washing with Aqueous Sodium Carbonate Solution (5-Residue Peptide)

The H-Glu (OtBu)-Ala-Glu (OtBu)-Lys (Boc)-Leu-NH-Dpm (OPhy) solution (solution-1) obtained in the above-mentioned step (B)-1 was fed at a flow rate of 1.08 ml/min, and 20 wt % NaCl aqueous solution (solution-2) was fed at a flow rate of 0.88 ml/min each using a pump, and merged using a T-shaped mixer (Union Tee SS-200-3; outer diameter ⅛ inch). After merging, the solution that became a slug flow (flow in which the organic layer and the aqueous layer are alternately repeated) was passed through a PFA tube (inner diameter 1.6 mm). The fulvene adduct that could not be completely removed in the above-mentioned step (B)-1 was removed into the aqueous layer, and then separated using an oil-water separation membrane (OB-2000-S-10; hydrophobic membrane with pore size 1.0 μm), and the permeated organic layer was recovered.

LC/MS M$^+$ m/z 1559.2

The apparatuses used in the following Examples 4 to 11 were as follows.

apparatus used (flow reactor, mixer, pump, oil-water separation means)

pump: plunger pump YMCU-22 [YMC CO., LTD.], syringe pump YSP-301 [YMC CO., LTD.], Diaphragm pump Q-10-6T-P-M49 [TACMINA CORPORATION]

flow reactor: PFA/PTFE tube (inner diameter 1.0 mm or 1.6 mm) [can be purchased from Swagelok Company, YMC CO., LTD., etc.); SUS piping (inner diameter 1.0 mm) [GL Sciences Inc.]

mixer: T-shaped mixer: Union Tee SS-100-3 (outer diameter ¹⁄₁₆ inch) or SS-200-3 (outer diameter ⅛ inch) [Swagelok Company], T-shaped micromixer (inner diameter 1.0 mm) [Sankoh Seiki Kogyo]

oil-water separation membrane apparatus: SEP-10 [Zaiput Flow Technologies]

oil-water separation membrane: OB-2000-S-10 (hydrophobic membrane with pore size 1.0 μm), OB-900-S-10 (hydrophobic membrane with pore size 0.5 μm) [Zaiput Flow Technologies]

Example 4

Synthesis of 15-Residue Peptide (Including D-Amino Acid) (H-Glu(OtBu)-Ala-(D)Pro-Pro-Gln (Trt)-Ala-Ala-(D)Pro-Pro-Ile-Pro-Gln(Trt)-Ala-Ala-Leu-OTOBPhy)

Step (B)-1: Washing with Aqueous Sodium Carbonate Solution After Removal Reaction of Fmoc/Step (B)-2: Washing with Aqueous Sodium Chloride Solution After Washing with Aqueous Sodium Carbonate Solution A chloroform solution containing 0.08 mmol/ml of H-(D) Pro-Pro-Gln(Trt)-Ala-Ala-(D)Pro-Pro-Ile-Pro-Gln(Trt)-Ala-Ala-Leu-OTOBPhy prepared by a batch method (solution-1) was merged with a solution obtained by mixing 5.0 wt % Na$_2$CO$_3$ aqueous solution and dimethyl formamide (DMF) at a volume ratio of 8:2 (solution-2), with a Diaphragm pump at a flow rate of 0.80 ml/min by using a T-shaped mixer (Union Tee SS-100-3; outer diameter ¹⁄₁₆ inch). After merging, the solution that became a slug flow (flow in which the organic layer and the aqueous layer are alternately repeated) was passed through a PFA tube (inner diameter 1.6 mm, length 10.0 m) for 11 min. The fulvene adduct produced during the removal reaction of Fmoc was removed into the aqueous layer, and separated using an oil-water separation membrane (OB-2000-S-10; hydrophobic membrane with pore size 1.0 µm). The resulting organic layer was further merged with a solution obtained by mixing 20.0 wt % NaCl aqueous solution and dimethylformamide (DMF) at a volume ratio of 6:4 (solution-3) by using a Diaphragm pump at a flow rate of 0.88 ml/min and a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 5.0 m) for 5 min. The fulvene adduct that could not be completely removed in step (B)-1 was removed into the aqueous layer, and then separated using an oil-water separation membrane (OB-900-S-10; hydrophobic membrane with pore size 0.5 µm), and an organic layer containing H-(D)Pro-Pro-Gln(Trt)-Ala-Ala-(D)Pro-Pro-Ile-Pro-Gln(Trt)-Ala-Ala-Leu-OTOBPhy was recovered.

LC/MS M+ m/z 2734.1

*) TOBPhy shows a 3,4,5-tri(2',3'-dihydrophytyloxy)benzyl group.

Step (1): Condensation Reaction/Step (A): Extraction After Condensation Reaction A chloroform solution containing 0.04 mmol/ml of H-(D)Pro-Pro-Gln(Trt)-Ala-Ala-(D)Pro-Pro-Ile-Pro-Gln(Trt)-Ala-Ala-Leu-OTOBPhy obtained by continuously performing the above-mentioned steps (B)-1, step (B)-2 (solution-1), and a dimethylformamide (DMF) solution containing 0.14 mmol/ml of Fmoc-Ala-OH and 0.04 mmol/ml of 1-hydroxybenzotriazole (HOBt) anhydride (solution-2) were fed using a plunger pump (may be a syringe pump or Diaphragm pump) at flow rates of 0.500, 0.208 ml/min, respectively, and mixed using a T-shaped mixer (Union Tee SS-100-3; outer diameter 1/16 inch). A chloroform solution containing 0.23 mmol/ml of N-ethyl-N'-3-dimethylaminopropylcarbodiimide hydrochloride (EDC.HCl) (solution-3) was fed at a flow rate of 0.133 ml/min, mixed with a mixed solution of solution-1, 2 by using a T-shaped mixer (Union Tee SS-100-3; outer diameter 1/16 inch), and reacted for 18 min in a PFA tube (inner diameter 1.6 mm, length 7.5 m). Furthermore, 20 wt % NaCl aqueous solution (solution-4) was fed at 0.56 ml/min using a Diaphragm pump, and merged with a mixture of the solutions-1, 2, and 3 using a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 5.0 m) for 7 min. The EDC.HCl remaining in the condensation reaction was deactivated and removed into the aqueous layer, and then separated using an oil-water separation membrane (OB-2000-S-10; hydrophobic membrane with pore size 1.0 µm), and an organic layer containing Fmoc-Ala-(D)Pro-Pro-Gln(Trt)-Ala-Ala-(D)Pro-Pro-Ile-Pro-Gln(Trt)-Ala-Ala-Leu-OTOBPhy was recovered.

Step (2): Removal Reaction of Fmoc/Step (B)-1: Washing with Aqueous Sodium Carbonate Solution After Removal Reaction of Fmoc/Step (B)-2: Washing with Aqueous Sodium Chloride Solution After Washing with Aqueous Sodium Carbonate Solution An organic layer containing 0.03 mmol/ml of Fmoc-Ala-(D)Pro-Pro-Gln(Trt)-Ala-Ala-(D)Pro-Pro-Ile-Pro-Gln(Trt)-Ala-Ala-Leu-OTOBPhy obtained by continuously performing the above-mentioned steps (1) and (A) (solution-1), and a dimethylformamide (DMF) solution containing 0.33 mmol/ml of thiomalic acid and 0.98 mmol/ml of 1,8-diazabicyclo[5.4.0]-7-undecene (DBU) (solution-2) were fed at a flow rate of 0.732, 0.346 ml/min, respectively, using a plunger pump (may be a syringe pump or Diaphragm pump), mixed in a T-shaped mixer (Union Tee SS-100-3; outer diameter 1/16 inch) and reacted for 7 min in a PFA tube (inner diameter 1.0 mm, length 10.0 m). Dibenzofulvene (DBF) generated during the reaction was reacted with thiomalic acid to convert same into a fulvene adduct. This reaction mixture after removal of Fmoc was mixed with 5.0 wt % Na₂CO₃ aqueous solution and dimethylformamide (DMF) at a volume ratio of 8:2 (solution-3), and merged using a Diaphragm pump at a flow rate of 0.80 ml/min in a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 10.0 m) for 11 min. The fulvene adduct produced during the removal reaction of Fmoc was removed into the aqueous layer, and then separated using an oil-water separation membrane (OB-2000-S-10; hydrophobic membrane with pore size 1.0 µm). The resulting organic layer was further merged with a solution obtained by mixing 20.0 wt % NaCl aqueous solution and dimethylformamide (DMF) at a volume ratio of 6:4 (solution-4) by using a Diaphragm pump at a flow rate of 0.88 ml/min and a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 5.0 m) for 5 min. The fulvene adduct that could not be completely removed in step (B)-1 was removed into the aqueous layer, and then separated using an oil-water separation membrane (OB-900-S-10; hydrophobic membrane with pore size 0.5 um), and an organic layer containing H-Ala-(D)Pro-Pro-Gln(Trt)-Ala-Ala-(D)Pro-Pro-Ile-Pro-Gln(Trt)-Ala-Ala-Leu-OTOBPhy was recovered.

LC/MS M+ m/z 2804.9

Step (1): Condensation Reaction/Step (A): Extraction After Condensation Reaction A chloroform solution (solution-1) containing 0.03 mmol/ml of H-Ala-(D)Pro-Pro-Gln(Trt)-Ala-Ala-(D)Pro-Pro-Ile-Pro-Gln(Trt)-Ala-Ala-Leu-OTOBPhy obtained by continuously performing the above-mentioned step (2), step (B)-1, and step (B)-2, and a dimethylformamide (DMF) solution (solution-2) containing 0.11 mmol/ml of Fmoc-Glu(OtBu)-OH and 0.03 mmol/ml of 1-hydroxybenzotriazole (HOBt) anhydride were fed using a plunger pump YMCU-22 (may be syringe pump or Diaphragm pump)) at flow rates of 0.500, 0.208 ml/min, respectively, and mixed using a T-shaped mixer (Union Tee SS-100-3; outer diameter 1/16 inch). A chloroform solution (solution-3) containing 0.23 mmol/ml of N-ethyl-N'-3-dimethylaminopropylcarbodiimide hydrochloride (EDC.HCl) was fed at a flow rate of 0.133 ml/min, mixed with the mixed solution of solutions-1, 2 by a T-shaped mixer (Union Tee SS-100-3; outer diameter 1/16 inch) and reacted in a PFA tube (inner diameter 1.6 mm, length 7.5 m) for 18 min. Furthermore, 20 wt % NaCl aqueous solution (solution-4) was fed at 0.56 ml/min using a Diaphragm pump and merged with a mixture of solutions-1, 2 and 3 in a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 5.0 m) for 7 min. The EDC.HCl remaining in the condensation reaction was deactivated and removed into the aqueous layer, and then separated using an oil-water separation membrane (OB-2000-S-10; hydrophobic membrane with pore size 1.0 μm), and an organic layer containing Fmoc-Glu(OtBu)-Ala-(D)Pro-Pro-Gln(Trt)-Ala-Ala-(D)Pro-Pro-Ile-Pro-Gln(Trt)-Ala-Ala-Leu-OTOBPhy was recovered.

Step (2): Removal Reaction of Fmoc/Step (B)-1: Washing with Aqueous Sodium Carbonate Solution After Removal Reaction of Fmoc/Step (B)-2: Washing with Aqueous Sodium Chloride Solution After Washing with Aqueous Sodium Carbonate Solution An organic layer (solution-1) containing 0.02 mmol/ml of Fmoc-Glu(OtBu)-Ala-(D)Pro-Pro-Gln(Trt)-Ala-Ala-(D)Pro-Pro-Ile-Pro-Gln(Trt)-Ala-Ala-Leu-OTOBPhy obtained by continuously performing the above-mentioned step (1) and step (A), and a dimethylformamide (DMF) solution (solution-2) containing 0.26 mmol/ml of thiomalic acid and 0.78 mmol/ml of 1,8-diazabicyclo[5.4.0]-7-undecene (DBU) were fed using a plunger pump (may be syringe pump or Diaphragm pump) at a flow rate of 0.732, 0.346 ml/min, respectively, mixed in a T-shaped mixer (Union Tee SS-100-3; outer diameter 1/16 inch), and reacted in a PFA tube (inner diameter 1.0 mm, length 10.0 m) for 7 min. Dibenzofulvene (DBF) generated during the reaction was reacted with thiomalic acid to convert same into a fulvene adduct. This reaction mixture after removal of Fmoc was mixed with 5.0 wt % $Na_2CO_3$ aqueous solution and dimethylformamide (DMF) at a volume ratio of 8:2 (solution-3), and merged using a Diaphragm pump at a flow rate of 0.80 ml/min in a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 10.0 m) for 11 min. The fulvene adduct produced during the removal reaction of Fmoc was removed into the aqueous layer, and then separated using an oil-water separation membrane (OB-2000-S-10; hydrophobic membrane with pore size 1.0 μm). The resulting organic layer was further merged with a solution obtained by mixing 20.0 wt % NaCl aqueous solution and dimethylformamide (DMF) at a volume ratio of 6:4 (solution-4) by using a Diaphragm pump at a flow rate of 0.88 ml/min and a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 5.0 m) for 5 min. The fulvene adduct that could not be completely removed in step (B)-1 was removed into the aqueous layer, and then separated using an oil-water separation membrane (OB-900-S-10; hydrophobic membrane with pore size 0.5 μm), and an organic layer containing H-Glu(OtBu)-Ala-(D)Pro-Pro-Gln(Trt)-Ala-Ala-(D)Pro-Pro-Ile-Pro-Gln(Trt)-Ala-Ala-Leu-OTOBPhy was recovered.

LC/MS $M^+$ m/z 2991.18

Example 5

Synthesis of 2-residue peptide (H-Asn(Trt)-Leu-NH-Dpm(OPhy))

Step (1): Condensation Reaction

To a chloroform solution (solution-1) containing 0.03 mmol/ml of H-Leu-NH-Dpm(OPhy) obtained in Production Example 1 was added each of 1.50 eq. of 1-hydroxybenzotriazole (HOBt) anhydride, Fmoc-Asn(Trt)-OH, and N-ethyl-N'-3-dimethylaminopropylcarbodiimide hydrochloride (EDC.HCl) to give Fmoc-Asn(Trt)-Leu-NH-Dpm (OPhy). Thereafter, 1.50 eq. each of N-ethyl-N'-3-dimethylaminopropylcarbodiimide hydrochloride (EDC.HCl) and thiomalic acid was added to deactivate excess active ester.

Step (A): Extraction After Condensation Reaction

A solution (solution-1) containing 0.03 mmol/ml of Fmoc-Asn(Trt)-Leu-NH-Dpm(OPhy) obtained in the above-mentioned step (1) and 20 wt % NaCl aqueous solution (solution-2) were each fed using a plunger pump and a Diaphragm pump at 1.500, 1.50 ml/min, and merged using a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 7.5 m) for 5 min. The EDC.HCl remaining in the condensation reaction was deactivated and removed into the aqueous layer, and then separated using a separating funnel, and the organic layer was recovered.

Step (2): Removal Reaction of Fmoc/Step (B)-3: Washing with Aqueous Sodium Chloride Solution After Removal Reaction of Fmoc An organic layer (solution-1) containing 0.04 mmol/ml of Fmoc-Asn(Trt)-Leu-NH-Dpm(OPhy) obtained in the above-mentioned step (A) and a dimethylformamide (DMF) solution (solution-2) containing 0.44 mmol/ml of thiomalic acid and 1.60 mmol/ml of 1,8-diazabicyclo[5.4.0]-7-undecene (DBU) were fed at a flow rate of 0.700, 0.300 ml/min, respectively, using a plunger pump (may be a syringe pump or a Diaphragm pump), mixed in a T-shaped mixer (Union Tee SS-100-3; outer diameter 1/16 inch), and reacted for 7 min in a PFA tube (inner diameter 1.0 mm, length 10.0 m). Dibenzofulvene (DBF) generated during the reaction was reacted with thiomalic acid to convert same into a fulvene adduct. The mixture after removal reaction of Fmoc was merged with 20.0 wt % NaCl aqueous solution by using a Diaphragm pump at a flow rate of 0.50 ml/min in a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 2.0 m) for 3 min. The fulvene adduct produced during the removal reaction of Fmoc was removed into the aqueous layer, and then separated using a separating funnel, and an organic layer containing H-Asn(Trt)-Leu-NH-Dpm (OPhy) was recovered.

Step (2): Removal Reaction of Fmoc/Step (B)-1: Washing with Aqueous Sodium Carbonate Solution After Removal Reaction of Fmoc An organic layer (solution-1) containing 0.04 mmol/ml of Fmoc-Asn(Trt)-Leu-NH-Dpm(OPhy) obtained in the above-mentioned step (A), and a dimethylformamide (DMF) solution containing 0.44 mmol/ml of thiomalic acid and 1.60 mmol/ml of 1,8-diazabicyclo[5.4.0]-7-undecene (DBU) (solution-2) were fed at a flow rate of 0.700, 0.300 ml/min, respectively, using a plunger pump (may be a syringe pump or Diaphragm pump), mixed in a T-shaped mixer (Union Tee SS-100-3; outer diameter 1/16 inch) and reacted for 7 min in a PFA tube (inner diameter 1.0 mm, length 10.0 m). Dibenzofulvene (DBF) generated during the reaction was reacted with thiomalic acid to convert same into a fulvene adduct. This reaction mixture after removal of Fmoc was merged with 5.0 wt % $Na_2CO_3$ aqueous solution using a Diaphragm pump at a flow rate of 0.50 ml/min in a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 2.0 m) for 3 min. The fulvene adduct produced during the removal reaction of Fmoc was removed into the aqueous layer, and then separated using a separating funnel, and the organic layer was recovered.

Step (B)-2: Washing with Aqueous Sodium Chloride Solution After Washing with Aqueous Sodium Carbonate Solution The organic layer (solution-1) obtained in step (B)-1, and a solution (solution-2) obtained by mixing 20.0 wt % NaCl aqueous solution and dimethylformamide (DMF) at a volume ratio of 6:4 were merged at a flow rate of 1.500, 1.50 ml/min using a plunger pump or a Diaphragm pump and using a T-shaped mixer (Union Tee SS-200-3; outer diameter ⅛ inch). After merging, the solution that became a slug flow (flow in which the organic layer and the aqueous layer are alternately repeated) was passed through a PFA tube (inner diameter 1.6 mm, length 7.5 m) for 5 min, the fulvene adduct that could not be completely removed in step (B)-1 was removed into the aqueous layer, and then separated using a separating funnel, and an organic layer containing H-Asn(Trt)-Leu-NH-Dpm(OPhy) was recovered.

LC/MS M+ m/z 1245.9

Example 6

Synthesis of 2-residue peptide (H-Asp(OtBu)-Leu-NH-Dpm(OPhy))

Step (1): Condensation Reaction/Step (A): Extraction After Condensation Reaction A chloroform solution (solution-1) containing 0.10 mmol/ml of H-Leu-NH-Dpm(OPhy) obtained in Production Example 1, and a dimethylformamide (DMF) solution (solution-2) containing 0.35 mmol/ml of Fmoc-Asp(OtBu)-OH and 0.09 mmol/ml of ethyl2-cyano-2-hydroxyiminoacetate (Oxyma) were fed using a plunger pump (may be a syringe pump or a Diaphragm pump) at a flow rate of 0.500, 0.208 ml/min, respectively, and mixed using a T-shaped mixer (Union Tee SS-100-3; outer diameter 1/16 inch). A chloroform solution (solution-3) containing 0.55 mmol/ml of N-ethyl-N'-3-dimethylaminopropylcarbodiimide hydrochloride (EDC.HCl) was fed at a flow rate of 0.133 ml/min, mixed with the mixed solution of solutions-1, 2 by a T-shaped mixer (Union Tee SS-100-3; outer diameter 1/16 inch) and reacted in a PFA tube (inner diameter 1.0 mm, length 10.0 m) for 9 min. Furthermore, 20 wt % NaCl aqueous solution (solution-4) was fed at 0.56 ml/min using a Diaphragm pump and merged with a mixture of solutions-1, 2, 3 using a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 5.0 m) for 7 min. The EDC.HCl remaining in the condensation reaction was deactivated and removed into the aqueous layer, and then separated using a separating funnel, and an organic layer containing Fmoc-Asp(OtBu)-Leu-NH-Dpm(OPhy) was recovered.

Step (2): Removal Reaction of Fmoc/Step (B)-1: Washing with Aqueous Sodium Carbonate Solution After Removal Reaction of Fmoc An organic layer (solution-1) containing 0.09 mmol/ml of Fmoc-Asp(OtBu)-Leu-NH-Dpm(OPhy) obtained by continuously performing the above-mentioned steps (1) and (A), and a dimethylformamide (DMF) solution (solution-2) containing 0.91 mmol/ml of thiomalic acid and 2.74 mmol/ml of 1,8-diazabicyclo[5.4.0]-7-undecene (DBU) were fed using a plunger pump (may be a syringe pump or a Diaphragm pump) at a flow rate of 0.732, 0.346 ml/min, respectively, mixed using a T-shaped mixer (Union Tee SS-100-3; outer diameter 1/16 inch), reacted in a PFA tube (inner diameter 1.0 mm, length 10.0 m) for 7 min. Dibenzofulvene (DBF) generated during the reaction was reacted with thiomalic acid to convert same into a fulvene adduct. This reaction mixture after removal of Fmoc was merged with 5.0 wt % Na$_2$CO$_3$ aqueous solution using a Diaphragm pump at a flow rate of 0.80 ml/min in a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 5.0 m) for 5 min. The fulvene adduct produced during the removal reaction of Fmoc was removed into the aqueous layer, and then separated using a separating funnel, and the organic layer was recovered.

Step (B)-2: Washing with Aqueous Sodium Chloride Solution After Washing with Aqueous Sodium Carbonate Solution The organic layer (solution-1) obtained in step (B)-1, and a solution (solution-2) obtained by mixing 20.0 wt % NaCl aqueous solution and dimethylformamide (DMF) at a volume ratio of 6:4 were merged using a plunger pump or a Diaphragm pump at a flow rate of 1.500, 1.50 ml/min, respectively, using a T-shaped mixer (Union Tee SS-200-3; outer diameter ⅛ inch). After merging, the solution that became a slug flow (flow in which the organic layer and the aqueous layer are alternately repeated) was passed through a PFA tube (inner diameter 1.6 mm, length 5.0 m) for 3 min, the fulvene adduct that could not be completely removed in step (B)-1 was removed into the aqueous layer, and then separated using a separating funnel, and an organic layer containing H-Asp(OtBu)-Leu-NH-Dpm(OPhy) was recovered.

LC/MS 2M+ m/z 2120.7

Example 7

Synthesis of 2-residue peptide (H-Ala-Leu-NH-Dpm(OPhy))

Step (1): Condensation Reaction/Step (A): Extraction After Condensation Reaction A chloroform solution (solution-1) containing 0.10 mmol/ml of H-Leu-NH-Dpm(OPhy) obtained in Production Example 1, and a dimethylformamide (DMF) solution (solution-2) containing 0.35 mmol/ml of Fmoc-Ala-OH and 0.09 mmol/ml of 1-hydroxybenzotriazole (HOBt) anhydride were fed using a plunger pump (may be a syringe pump or Diaphragm pump) at flow rates of 0.500, 0.208 ml/min, respectively, and mixed using a T-shaped mixer (Union Tee SS-100-3; outer diameter 1/16 inch). A chloroform solution (solution-3) containing 0.55 mmol/ml of N-ethyl-N'-3-dimethylaminopropylcarbodiimide hydrochloride (EDC.HCl) was fed at a flow rate of 0.133 ml/min and mixed with a mixed solution of solutions-1, 2 by using a T-shaped mixer (Union Tee SS-100-3; outer diameter 1/16 inch), incubated in a water bath at 43° C. and reacted in a SUS piping (inner diameter 1.0 mm, length 10.0 m) for 9 min. Furthermore, a 20 wt % NaCl aqueous solution (solution-4) was fed at 0.56 ml/min using a Diaphragm pump and merged with a mixture of solutions-1, 2, 3 by using a T-shaped mixer (micro mixer manufactured by Sankoh Seiki Kogyo; inner diameter 1.0 mm). After merging, the solution that became a slug flow (flow in which the organic layer and the aqueous layer are alternately repeated) was passed through a SUS piping (inner diameter 1.0 mm, length 7.0 m) for 4 min. The EDC.HCl remaining in the condensation reaction was deactivated and removed into the aqueous layer, and then separated using a separating funnel, and an organic layer containing Fmoc-Ala-Leu-NH-Dpm(OPhy) was recovered.

Step (2): Removal reaction of Fmoc/Step (B)-1: Washing with Aqueous Sodium Carbonate Solution After Removal Reaction of Fmoc An organic layer (solution-1) containing 0.09 mmol/ml of Fmoc-Ala-Leu-NH-Dpm(OPhy) obtained by continuously performing the above-mentioned steps (1) and (A) and a dimethylformamide (DMF) solution (solution-2) containing 0.92 mmol/ml of thiomalic acid and 2.75 mmol/ml of 1,8-diazabicyclo[5.4.0]-7-undecene (DBU) were fed using a plunger pump (may be a syringe pump or Diaphragm pump) at flow rates of 0.732, 0.346 ml/min, respectively, and mixed using a T-shaped mixer (Union Tee SS-100-3; outer diameter 1/16 inch), incubated in a water bath at 43° C. and reacted in a SUS piping (inner diameter 1.0 mm, length 10.0 m) for 7 min. Dibenzofulvene (DBF) generated during the reaction was reacted with thiomalic acid to convert same into a fulvene adduct. This reaction mixture after removal of Fmoc was merged with 5.0 wt % $K_2CO_3$ aqueous solution (solution-3) using a Diaphragm pump at a flow rate of 0.80 ml/min in a T-shaped mixer (micro mixer manufactured by Sankoh Seiki Kogyo; inner diameter 1.0 mm). After merging, the solution that became a slug flow (flow in which the organic layer and the aqueous layer are alternately repeated) was passed through a SUS piping (inner diameter 1.0 mm, length 7.0 m) for 3 min. The fulvene adduct produced during the removal reaction of Fmoc was removed into the aqueous layer, and then separated using a separating funnel, and the organic layer was recovered.

Step (B)-2: Washing with Aqueous Sodium Chloride Solution After Washing with Aqueous Sodium Carbonate Solution The organic layer (solution-1) obtained in step (B)-1, and a solution (solution-2) obtained by mixing 20.0 wt % NaCl aqueous solution and dimethylformamide (DMF) at a volume ratio of 6:4 were merged at a flow rate of 1.000, 1.00 ml/min using a plunger pump or a Diaphragm pump and using a T-shaped mixer (micro mixer manufactured by Sankoh Seiki Kogyo; inner diameter 1.0 mm). After merging, the solution that became a slug flow (flow in which the organic layer and the aqueous layer are alternately repeated) was passed through a SUS piping (inner diameter 1.0 mm, length 7.0 m) for 3 min, the fulvene adduct that could not be completely removed in step (B)-1 was removed into the aqueous layer, and then separated using a separating funnel, and an organic layer containing H-Ala-Leu-NH-Dpm (OPhy) was recovered.

LC/MS $2M^+$ m/z 1920.6

Example 8

Synthesis of 2-Residue Peptide (H-Cys(Trt)Lys(Boc)-NH-Dpm(OPhy))

Step (1): Condensation Reaction (Preparation by Batch Method)

To a cyclopentylmethylether (CPME) solution (solution-1) containing 0.06 mmol/ml of H-Lys(Boc)-NH-Dpm (OPhy) obtained by a method similar to that in Production Example 1 was added each of 1.50 eq. of 1-hydroxybenzotriazole (HOBt) anhydride, Fmoc-Cys(Trt)-OH, and N-ethyl-N'-3-dimethylaminopropylcarbodiimide hydrochloride (EDC.HCl) to give Fmoc-Cys(Trt)-Leu-NH-Dpm (OPhy). Thereafter, 1.50 eq. each of N-ethyl-N'-3-dimethylaminopropylcarbodiimide hydrochloride (EDC.HCl) and mercaptopropionic acid was added to deactivate excess active ester.

Step (A): Extraction After Condensation Reaction

A solution (solution-1) containing 0.06 mmol/ml of Fmoc-Cys(Trt)-Lys(Boc)-NH-Dpm(OPhy) obtained in the above-mentioned step (1) and 20 wt % NaCl aqueous solution (solution-2) were each fed using a plunger pump and a Diaphragm pump at 1.500, 1.50 ml/min, and merged using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm, length 7.5 m) for 5 min. The EDC.HCl remaining in the condensation reaction was deactivated and removed into the aqueous layer, and then separated using a separating funnel, and the organic layer was recovered.

Step (2): Removal Reaction of Fmoc/Step (B)-3: Washing with Aqueous Sodium Chloride Solution After Removal Reaction of Fmoc An organic layer (solution-1) containing 0.06 mmol/ml of Fmoc-Cys(Trt)-Lys(Boc)-NH-Dpm(OPhy) obtained in the above-mentioned step (A) and a dimethylformamide (DMF) solution (solution-2) containing 0.72 mmol/ml of mercaptopropionic acid and 1.44 mmol/ml of 1,8-diazabicyclo [5.4.0]-7-undecene (DBU) were fed at a flow rate of 0.700, 0.300 ml/min, respectively, using a plunger pump (may be a syringe pump or a Diaphragm pump), mixed in a T-shaped mixer (Union Tee SS-100-3; outer diameter 1/16 inch), and reacted for 8 min in a PFA tube (inner diameter 1.0 mm, length 10.0 m). Dibenzofulvene (DBF) generated during the reaction was reacted with mercaptopropionic acid to convert same into a fulvene adduct. The mixture after removal reaction of Fmoc was merged with 20.0 wt % NaCl aqueous solution by using a Diaphragm pump at a flow rate of 0.50 ml/min in a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 5.0 m) for 7 min. The fulvene adduct produced during the removal reaction of Fmoc was removed into the aqueous layer, and then separated using a separating funnel, and an organic layer containing H-Cys(Trt)-Lys(Boc)-NH-Dpm(OPhy) was recovered.

LC/MS $M^+$ m/z 1350.0

Example 9

2-residue peptide (H-Gly-Glu(OtBu)-OMTBPhy)synthesis

Step (1): Condensation Reaction/Step (A): Extraction After Condensation Reaction A chloroform solution (solution-1) containing 0.06 mmol/ml H-Glu(OtBu)-OMTBPhy obtained by a method similar to that in Production Example 1, and a dimethylformamide (DMF) solution (solution-2) containing 0.21 mmol/ml of Fmoc-Gly-OH and 0.05 mmol/ml of 1-hydroxybenzotriazole (HOBt) anhydride were fed using a plunger pump (may be a syringe pump or a Diaphragm pump) at flow rates of 0.500, 0.208 ml/min, respectively, and mixed using a T-shaped mixer (Union Tee SS-100-3; outer diameter 1/16 inch). A chloroform solution (solution-3) containing 0.32 mmol/ml of N-ethyl-N'-3-dimethylaminopropylcarbodiimide hydrochloride (EDC.HCl) was fed at a flow rate of 0.133 ml/min, mixed with the mixed solution of solutions-1, 2 by a T-shaped mixer (Union Tee SS-100-3; outer diameter 1/16 inch) and reacted in a PFA tube (inner diameter 1.0 mm, length 10.0 m) for 9 min. Furthermore, a 20 wt % NaCl aqueous solution (solution-4) was fed at 0.56 ml/min using a Diaphragm pump and merged with a mixture of solutions-1, 2, 3 by using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm, length 5.0 m) for 7 min. The EDC.HCl remaining in the condensation reaction was deactivated, removed into the aqueous layer, separated using a separating funnel and an organic layer containing Fmoc-Gly-Glu(OtBu)-OMTBPhy was recovered.

*) MTBPhy shows a 2-(3,4,5-tri(2',3'-dihydrophytyloxy) benzyloxy)-4-methoxybenzyl group.

Step (2): Removal Reaction of Fmoc/Step (B)-1: Washing with Aqueous Sodium Carbonate Solution After Removal Reaction of Fmoc An organic layer (solution-1) containing 0.05 mmol/ml of Fmoc-Gly-Glu(OtBu)-OMTBPhy obtained by continuously performing the above-mentioned steps (1) and (A), and a dimethylformamide (DMF) solution (solution-2) containing 0.52 mmol/ml of thiomalic acid and 1.57 mmol/ml of 1,8-diazabicyclo[5.4.0]-7-undecene (DBU) were fed using a plunger pump (may be a syringe pump or a Diaphragm pump) at flow rates of 0.732, 0.346 ml/min, respectively, and mixed using a T-shaped mixer (Union Tee SS-100-3; outer diameter 1/16 inch), and reacted in a PFA tube (inner diameter 1.0 mm, length 10.0 m) for 7 min. Dibenzofulvene (DBF) generated during the reaction was reacted with thiomalic acid to convert same into a fulvene adduct. This reaction mixture after removal of Fmoc was merged with 5.0 wt % $Na_2CO_3$ aqueous solution using a Diaphragm pump at a flow rate of 0.50 ml/min in a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 5.0 m) for 5 min. The fulvene adduct produced during the removal reaction of Fmoc was removed into the aqueous layer, and then separated using a separating funnel, and the organic layer was recovered.

Step (B)-2: Washing with Aqueous Sodium Chloride Solution After Washing with Aqueous Sodium Carbonate Solution The organic layer (solution-1) obtained in step (B)-1, and a solution (solution-2) obtained by mixing 20.0 wt % NaCl aqueous solution and dimethylformamide (DMF) at a volume ratio of 6:4 were merged using a plunger pump or a Diaphragm pump at a flow rate of 1.500, 1.50 ml/min, respectively, using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm, length 5.0 m) for 3 min, the fulvene adduct that could not be completely removed in step (B)-1 was removed into the aqueous layer, and then separated using a separating funnel, and an organic layer containing H-Gly-Glu(OtBu)-OMTBPhy was recovered.

LC/MS $M^+$ m/z 1376.1

Example 10

Synthesis of 2-Residue Peptide (H-Tyr(tBu)-Phe-OTOC)

Step (1): Condensation Reaction/Step (A): Extraction After Condensation Reaction A chloroform solution (solution-1) containing 0.06 mmol/ml of H-Phe-OTOC obtained by a method similar to that in Production Example 1, and a dimethylformamide (DMF) solution (solution-2) containing 0.22 mmol/ml of Fmoc-Tyr (tBu)-OH and 0.06 mmol/ml of 1-hydroxybenzotriazole (HOBt) anhydride were fed using a plunger pump (may be a syringe pump or a Diaphragm pump) at flow rates of 0.500, 0.208 ml/min, respectively, and mixed using a T-shaped mixer (Union Tee SS-100-3; outer diameter 1/16 inch). A chloroform solution (solution-3) containing 0.34 mmol/ml of N-ethyl-N'-3-dimethylaminopropylcarbodiimide hydrochloride (EDC.HCl) was fed at a flow rate of 0.133 ml/min, mixed with the mixed solution of solutions-1, 2 by a T-shaped mixer (Union Tee SS-100-3; outer diameter 1/16 inch) and reacted in a PFA tube (inner diameter 1.0 mm, length 10.0 m) for 9 min. Furthermore, a 20 wt % NaCl aqueous solution (solution-4) was fed at 0.56 ml/min using a Diaphragm pump and merged with a mixture of solutions-1, 2, 3 by using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm, length 5.0 m) for 7 min. The EDC.HCl remaining in the condensation reaction was deactivated and removed into the aqueous layer, and then separated using a separating funnel, and an organic layer containing Fmoc-Tyr(tBu)-Phe-OTOC was recovered.

*) TOC shows a 3,4,5-tri(octadecyloxy)cyclohexylmethyl group.

Step (2): Removal Reaction of Fmoc/Step (B)-1: Washing with Potassium Carbonate Aqueous Solution After Removal Reaction of Fmoc An organic layer (solution-1) containing 0.05 mmol/ml of Fmoc-Tyr(tBu)-Phe-OTOC obtained by continuously performing the above-mentioned steps (1) and (A), and a dimethylformamide (DMF) solution (solution-2) containing 0.55 mmol/ml of thiomalic acid and 1.66 mmol/ml of 1,8-diazabicyclo[5.4.0]-7-undecene (DBU) were fed using a plunger pump (may be a syringe pump or a Diaphragm pump) at flow rates of 0.732, 0.346 ml/min, respectively, and mixed using a T-shaped mixer (Union Tee SS-100-3; outer diameter 1/16 inch), and reacted in a PFA tube (inner diameter 1.0 mm, length 10.0 m) for 7 min. Dibenzofulvene (DBF) generated during the reaction was reacted with thiomalic acid to convert same into a fulvene adduct. This reaction mixture after removal of Fmoc was merged with 5.0 wt % $K_2CO_3$ aqueous solution using a Diaphragm pump at a flow rate of 0.80 ml/min in a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 2.0 m) for 3 min. The fulvene adduct produced during the removal reaction of Fmoc was removed into the aqueous layer, and then separated using a separating funnel, and the organic layer was recovered.

Step (B)-2: Washing with Aqueous Sodium Chloride Solution After Washing with Aqueous Potassium Carbonate Solution The organic layer (solution-1) obtained in step (B)-1, and a solution (solution-2) obtained by mixing 20.0 wt % NaCl aqueous solution and dimethylformamide (DMF) at a volume ratio of 6:4 were merged using a plunger pump or a Diaphragm pump at a flow rate of 1.500, 1.50 ml/min, respectively, using a T-shaped mixer (Union Tee SS-200-3; outer diameter 1/8 inch). After merging, the solution that became a slug flow (flow in which the organic layer and the aqueous layer are alternately repeated) was passed through a PFA tube (inner diameter 1.6 mm, length 5.0 m) for 3 min, the fulvene adduct that could not be completely removed in step (B)-1 was removed into the aqueous layer, and then separated using a separating funnel, and an organic layer containing H-Tyr(tBu)-Phe-OTOC was recovered.

LC/MS M$^+$ m/z 1286.0

Example 11

Synthesis of 16-residue peptide (including D-amino acid) (H-Leu-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy)

Step (1): Condensation Reaction

To a chloroform solution (solution-1) containing 0.03 mmol/ml of H-(D)Pro-Pro-Gln(Trt)-Ala-Ala-(D)Pro-Pro-Ile-Pro-Gln(Trt)-Ala-Ala-Leu-OTOBPhy prepared by a batch method were added 1.50 eq. each of 1-hydroxybenzotriazole (HOBt) anhydride, Fmoc-Glu(OtBu)-OH, and N-ethyl-N'-3-dimethylaminopropylcarbodiimide hydrochloride (EDC.HCl) to obtain Fmoc-Glu(OtBu)-(D)Pro-Pro-Gln(Trt)-Ala-Ala-(D)Pro-Pro-Ile-Pro-Gln(Trt)-Ala-Ala-Leu-OTOBPhy. Thereafter, 1.50 eq. each of N-ethyl-N'-3-dimethylaminopropylcarbodiimide hydrochloride (EDC.HCl) and thiomalic acid was added to deactivate excess active ester.

Step (A): Extraction After Condensation Reaction

A solution (solution-1) containing 0.03 mmol/ml of Fmoc-Glu(OtBu)-(D)Pro-Pro-Gln(Trt)-Ala-Ala-(D)Pro-Pro-Ile-Pro-Gln(Trt)-Ala-Ala-Leu-OTOBPhy obtained in the above-mentioned step (1), and a 20 wt % NaCl aqueous solution (solution-2) were fed using a plunger pump and a Diaphragm pump at flow rates of 1.500, 1.50 ml/min, respectively, and merged using a T-shaped mixer (Union Tee SS-200-3; outer diameter ⅛ inch). After merging, the solution that became a slug flow (flow in which the organic layer and the aqueous layer are alternately repeated) was passed through a PFA tube (inner diameter 1.6 mm, length 7.5 m) for 5 min, the EDC.HCl remaining in the condensation reaction was deactivated, removed into the aqueous layer, and then separated using an oil-water separation membrane (OB-900-S-10; hydrophobic membrane with pore size 0.5 pm), and an organic layer containing Fmoc-Glu(OtBu)-(D)Pro-Pro-Gln(Trt)-Ala-Ala-(D)Pro-Pro-Ile-Pro-Gln(Trt)-Ala-Ala-Leu-OTOBPhy was recovered.

Step (2): Removal Reaction of Fmoc/Step (B)-3: Washing with Aqueous Sodium Chloride Solution After Removal Reaction of Fmoc An organic layer (solution-1) containing 0.03 mmol/ml of Fmoc-Glu(OtBu)-(D)Pro-Pro-Gln(Trt)-Ala-Ala-(D)Pro-Pro-Ile-Pro-Gln(Trt)-Ala-Ala-Leu-OTOBPhy obtained in the above-mentioned step (A), and a dimethylformamide (DMF) solution (solution-2) containing 0.40 mmol/ml of thiomalic acid and 1.45 mmol/ml of 1,8-diazabicyclo[5.4.0]-7-undecene (DBU) were fed using a plunger pump (may be a syringe pump or a Diaphragm pump) at flow rates of 0.700, 0.300 ml/min, respectively, and mixed using a T-shaped mixer (Union Tee SS-100-3; outer diameter 1/16 inch), and reacted in a PFA tube (inner diameter 1.0 mm, length 10.0 m) for 7 min. Dibenzofulvene (DBF) generated during the reaction was reacted with thiomalic acid to convert same into a fulvene adduct. The mixture after removal reaction of Fmoc was merged with a 20.0 wt % NaCl aqueous solution by using a Diaphragm pump at a flow rate of 0.50 ml/min and a T-shaped mixer (Union Tee SS-100-3; outer diameter 1/16 inch). After merging, the solution that became a slug flow (flow in which the organic layer and the aqueous layer are alternately repeated) was passed through a PFA tube (inner diameter 1.6 mm, length 5.0 m) for 7 min. The fulvene adduct produced during the removal reaction of Fmoc was removed into the aqueous layer, separated using a separating funnel, and an organic layer was recovered. Furthermore, the obtained organic layer was passed through an oil-water separation membrane (OB-2000-S-10; hydrophobic membrane with pore size 1.0 μm) to remove water slightly remaining in the organic layer, and an organic layer containing H-Glu(OtBu)-(D)Pro-Pro-Gln(Trt)-Ala-Ala-(D)Pro-Pro-Ile-Pro-Gln(Trt)-Ala-Ala-Leu-OTOBPhy was obtained.

LC/MS M$^{2+}$ m/z 1460.0

Step (1): Condensation Reaction

To a chloroform solution (solution-1) containing 0.03 mmol/ml of H-Glu(OtBu)-(D)Pro-Pro-Gln(Trt)-Ala-Ala-(D)Pro-Pro-Ile-Pro-Gln(Trt)-Ala-Ala-Leu-OTOBPhy obtained by continuously performing the above-mentioned step (2) and step (B)-3 was added 1.50 eq. each of 1-hydroxybenzotriazole (HOBt) anhydride, Fmoc-Lys(Boc)-OH, and N-ethyl-N'-3-dimethylaminopropylcarbodiimide hydrochloride (EDC.HCl) to obtain Fmoc-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy. Thereafter, 1.50 eq. of N-ethyl-N'-3-dimethylaminopropylcarbodiimide hydrochloride (EDC.HCl) and thiomalic acid were added to deactivate excess active ester.

Step (A): Extraction After Condensation Reaction

A solution (solution-1) containing 0.03 mmol/ml of Fmoc-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy obtained in the above-mentioned step (1), and a 20 wt % NaCl aqueous solution (solution-2) were respectively fed using a plunger pump and a Diaphragm pump at 1.500, 1.50 ml/min and merged using a T-shaped mixer (Union Tee SS-200-3; outer diameter ⅛ inch). After merging, the solution that became a slug flow (flow in which the organic layer and the aqueous layer are alternately repeated) was passed through a PFA tube (inner diameter 1.6 mm, length 7.5 m) for 5 min, EDC.HCl remaining in the condensation reaction was deactivated, removed into the aqueous layer, and separated using an oil-water separation membrane (OB-900-S-10; hydrophobic membrane with pore size 0.5 μm), and an organic layer containing Fmoc-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy was recovered.

Step (2): Removal Reaction of Fmoc/Step (B)-3: Washing with Aqueous Sodium Chloride Solution After Removal Reaction of Fmoc An organic layer (solution-1) containing 0.04 mmol/ml of Fmoc-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy obtained in the above-mentioned step (A), and a dimethylformamide (DMF) solution (solution-2) containing 0.50 mmol/ml of thiomalic acid and 1.80 mmol/ml of 1,8-diazabicyclo[5.4.0]-7-undecene (DBU) were respectively fed using a plunger pump (may be a syringe pump or a Diaphragm pump) at a flow rate of 0.700, 0.300 ml/min, mixed using a T-shaped mixer (Union Tee SS-100-3; outer diameter 1/16 inch), and reacted in a PFA tube (inner diameter 1.0 mm, length 10.0 m) for 8 min. Dibenzofulvene (DBF) generated during the reaction was reacted with thiomalic acid to convert same into a fulvene adduct. This reaction mixture after removal of Fmoc was merged with a 20.0 wt % NaCl aqueous solution by using a Diaphragm pump at a flow rate of 0.50 ml/min in a T-shaped mixer (Union Tee SS-100-3; outer diameter ¹⁄₁₆ inch). After merging, the solution that became a slug flow (flow in which the organic layer and the aqueous layer are alternately repeated) was passed through a PFA tube (inner diameter 1.6 mm, length 5.0 m) for 7 min. The fulvene adduct produced during the removal reaction of Fmoc was removed into the aqueous layer, separated using a separating funnel, and an organic layer was recovered. Furthermore, the obtained organic layer was passed through an oil-water separation membrane (OB-2000-S-10; hydrophobic membrane with pore size 1.0 μm) to remove water slightly remaining in the organic layer, and an organic layer containing H-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy was obtained.

LC/MS $M^{2+}$ m/z 1574.0

Step (1): Condensation Reaction

To a chloroform solution (solution-1) containing 0.04 mmol/ml of H-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy obtained by continuously performing the above-mentioned step (2) and step (B)-3 was added 1.50 eq. each of 1-hydroxybenzotriazole (HOBt) anhydride and Fmoc-Leu-OH, N-ethyl-N'-3-dimethylaminopropylcarbodiimide hydrochloride (EDC.HCl) to obtain Fmoc-Leu-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy. Thereafter, 1.50 eq. each of N-ethyl-N'-3-dimethylaminopropylcarbodiimide hydrochloride (EDC.HCl) and thiomalic acid was added to deactivate excess active ester.

Step (A): Extraction After Condensation Reaction

A solution (solution-1) containing 0.03 mmol/ml of Fmoc-Leu-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy obtained in the above-mentioned step (1) and a 20 wt % NaCl aqueous solution (solution-2) were each fed using a plunger pump and a Diaphragm pump at 1.500, 1.50 ml/min and merged using a T-shaped mixer (Union Tee SS-200-3; outer diameter ⅛ inch). After merging, the solution that became a slug flow (flow in which the organic layer and the aqueous layer are alternately repeated) was passed through a PFA tube (inner diameter 1.6 mm, length 7.5 m) for 5 min. The EDC.HCl remaining in the condensation reaction was deactivated and removed into the aqueous layer, and then separated using an oil-water separation membrane (OB-900-S-10; hydrophobic membrane with pore size 0.5 μm), and an organic layer containing Fmoc-Leu-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy was recovered.

Step (2): Removal Reaction of Fmoc/Step (B)-3: Washing with Aqueous Sodium Chloride Solution After Removal Reaction of Fmoc An organic layer (solution-1) containing 0.05 mmol/ml of Fmoc-Leu-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy obtained in the above-mentioned step (A), and a dimethylformamide (DMF)solution (solution-2) containing 0.63 mmol/ml of thiomalic acid and 2.26 mmol/ml of 1,8-diazabicyclo[5.4.0]-7-undecene (DBU) were each fed using a plunger pump (may be a syringe pump or a Diaphragm pump) at a flow rate of 0.700, 0.300 ml/min, mixed in a T-shaped mixer (Union Tee SS-100-3; outer diameter ¹⁄₁₆ inch), and then reacted for 8 min in a PFA tube (inner diameter 1.0 mm, length 10.0 m). Dibenzofulvene (DBF) generated during the reaction was reacted with thiomalic acid to convert same into a fulvene adduct. The mixture after removal reaction of Fmoc was merged with 20.0 wt % NaCl aqueous solution by using a Diaphragm pump at a flow rate of 0.50 ml/min in a T-shaped mixer (Union Tee SS-100-3; outer diameter ¹⁄₁₆ inch). After merging, the solution that became a slug flow (flow in which the organic layer and the aqueous layer are alternately repeated) was passed through a PFA tube (inner diameter 1.6 mm, length 5.0 m) for 7 min. The fulvene adduct produced during the removal reaction of Fmoc was removed into the aqueous layer and separated using a separating funnel, and an organic layer was recovered. Furthermore, the obtained organic layer was passed through an oil-water separation membrane (OB-2000-S-10; hydrophobic membrane with pore size 1.0 μm) to remove water slightly remaining in the organic layer, and an organic layer containing H-Leu-Lys(Boc)-Glu(OtBu)-(D)Pro-Pro-Gln(Trt)-Ala-Ala-(D)Pro-Pro-Ile-Pro-Gln(Trt)-Ala-Ala-Leu-OTOBPhy was obtained.

LC/MS $M^{2+}$ m/z 1630.6

INDUSTRIAL APPLICABILITY

The present invention relates to a method for continuously producing peptide, and is useful in the field of peptide synthesis.

Where a numerical limit or range is stated herein, the endpoints are included. Also, all values and subranges within a numerical limit or range are specifically included as if explicitly written out.

As used herein the words "a" and "an" and the like carry the meaning of "one or more." Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for producing a peptide by flow synthesis in a flow reactor wherein the peptide is protected by a pseudo-solid phase protecting group to maintain solubility of the peptide as it elongates, comprising the following (A) or (B), or a combination thereof:
   (A) producing a reaction mix comprising the peptide protected by a pseudo-solid-phase group in a flow reactor; wherein the peptide comprises an N-protected C-protected peptide having an amino acid residue number of from 5 to 100, in which an N-terminal amino group and C-terminal are protected by protecting groups;
   washing the reaction mix that contains the peptide with water and/or a hydrophilic organic solvent
   and then
   separating the peptide into an organic layer via an oil and water type phase separation comprising water or the hydrophilic organic solvent and a solvent immiscible with water or the hydrophilic organic solvent, thereby recovering the protected peptide,
   wherein protected peptide solution is diluted 5- to 100-fold compared to the initial concentration of the substrate peptide in the immiscible solvent
   (B) producing a reaction mix comprising the peptide protected by a pseudo-solid-phase group in a flow reactor; wherein the peptide comprises an N-terminal amino group that is not protected, a C-terminal that is protected by a protecting group having an amino acid residue number of from 5 to 100, in which an N-terminal amino group is not protected and C-terminal are protected by protecting groups:
washing the reaction mix that contains the peptide with water and/or a hydrophilic organic solvent; separating the peptide into an organic layer via an oil and water type phase separation comprising water or the hydrophilic organic solvent and a second solvent immiscible with water or immiscible with the hydrophilic organic solvent, thereby recovering the protected peptide,
wherein protected peptide solution is diluted 2- to 100-fold compared to the initial concentration of the substrate peptide in the immiscible solvent

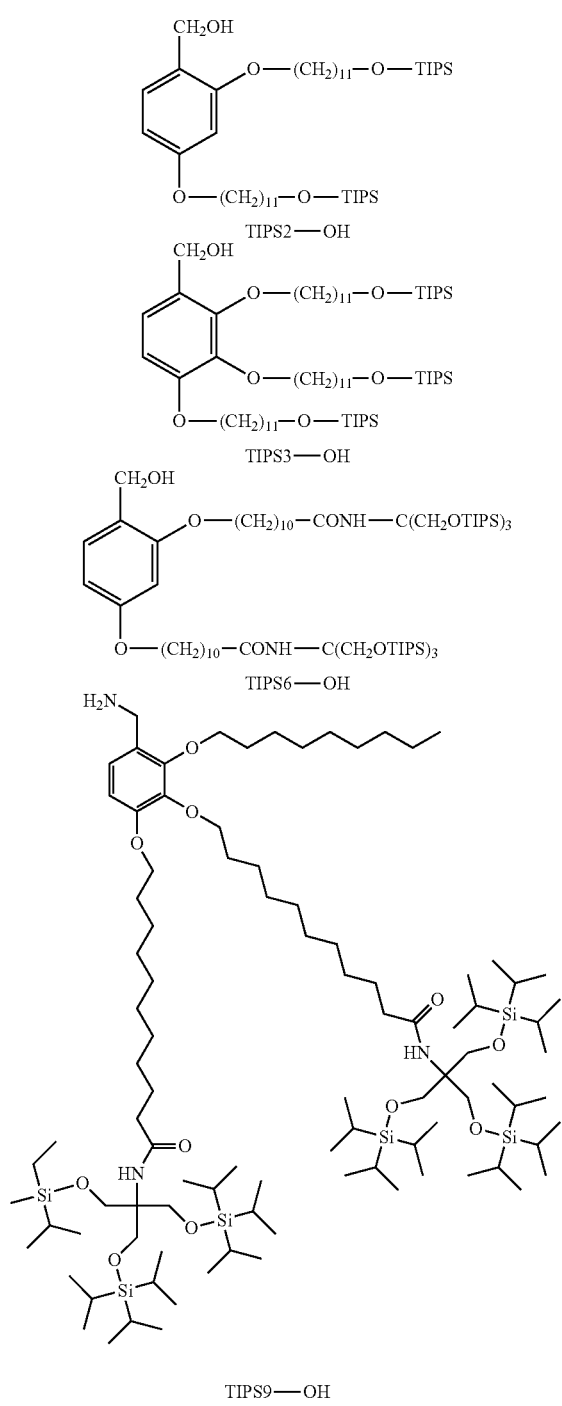

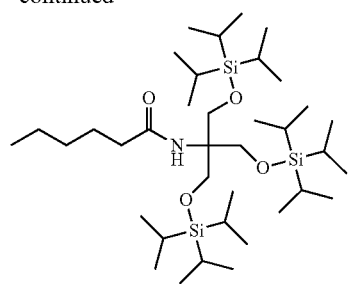

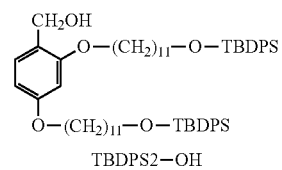

-continued

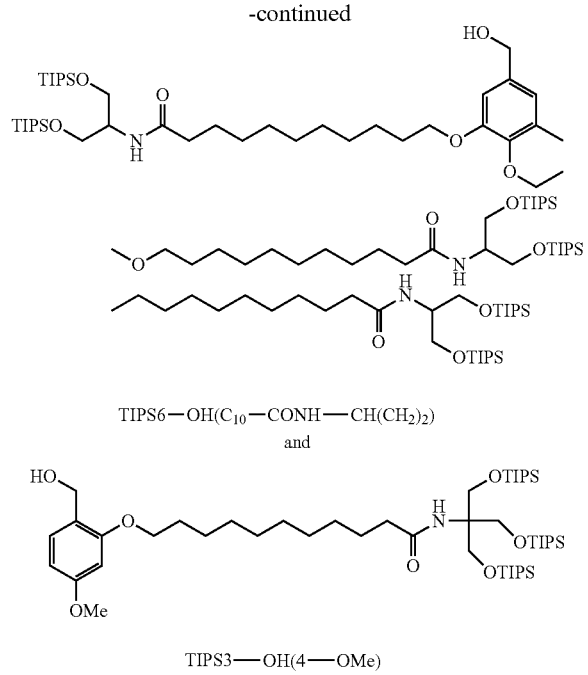

TIPS6—OH(C$_{10}$—CONH—CH(CH$_2$)$_2$)
and

TIPS3—OH(4—OMe)

2. The production method according to claim 1, wherein the oil-water separation is conducted by a continuous layer separation using a filter, or by a Gravity continuous layer separation.

3. The production method according to claim 1, wherein the protecting group of the amino group is a 9-fluorenylmethyloxycarbonyl group, a tert-butoxycarbonyl group, or a benzyloxycarbonyl group.

4. The production method according to claim 3, wherein the protecting group of the amino group is a 9-fluorenylmethyloxycarbonyl group.

5. The production method according to claim 1, further comprising obtaining the organic layer comprising the N-protected C-protected peptide obtained in the (A), or the N-unprotected C-protected peptide obtained in the (B), and then removing all protecting groups.

6. The production method according to claim 1, wherein the pseudo-solid-phase protecting group is selected from the group consisting of:
(4',4'-bis (2,3-dihydrophytyloxy) phenyl) methylamine);
3,4,5-tri (2',3'-dihydrophytyloxy) benzyl alcohol;
2-[3,4,5-tri (2',3'-dihydrophytyloxy) benzyloxy]-4-methoxybenzylalcohol; and
3,4,5-tri (octadecyloxy) cyclohexanemethanol.

7. The method of claim 1 that comprises (A).

8. The method of claim 1, that comprises (B).

9. The method of claim 1, wherein (A) or (B) a side chain functional group is further protected by a protecting group, and at least one of the C-terminal or the side chain functional group is protected by a pseudo-solid-phase protecting group.

10. The method of claim 1, wherein the water or hydrophilic organic solvent comprises a nitril, a ketone, an amide, or a sulfoxide.

11. The method of claim 1, wherein the water or hydrophilic organic solvent comprises acetonitrile, N,N-dimethylformamide (DMF), or N-methylpyrrolidone (NMP).

12. The method of claim 1, wherein the organic solvent immiscible with water comprises a hydrocarbon, an aromatic hydrocarbon or a halogenated hydrocarbon.

13. The method of claim 1, wherein the second organic solvent immiscible with water comprises chloroform, dichloromethane, tetrahydrofuran (THF) or cyclopentylmethylether (CPME).

14. The method of claim 1, wherein the pseudo-solid phase protecting group is at least one selected from the group consisting of:
(4',4'-bis (2,3-dihydrophytyloxy) phenyl) methylamine);
3,4,5-tri (2',3'-dihydrophytyloxy) benzyl alcohol;
2-[3,4,5-tri (2',3'-dihydrophytyloxy) benzyloxy]-4-methoxybenzyl alcohol;
3,4,5-tri (octadecyloxy) cyclohexanemethanol;
[bis-(4-docosoxy-phenyl)-methyl]-amine;
3,4,5-tri (octadecyloxy) benzyl alcohol;
4-methoxy-2-[3',4',5'-tris (octadecyloxy) benzyloxy) benzyl alcohol;
4-methoxy-2-[3',4',5'-tris (octadecyloxy) cyclohexylmethyloxy] benzyl alcohol;
2-docosyloxy-9-(4-chlorophenyl)-9-fluorenol;
2-docosyloxy-9-(4-chlorophenyl)-9-bromofluorene;
2,7-didocosyloxy-9-(4-chlorophenyl)-9-bromofluorene;
2-(12-docosyloxy-dodecanoxy)-9-(3-fluorophenyl)-9-bromofluorene;
1,12-bis-[12-(2'-O-9-(4-chlorophenyl)-9-fluorenol)-dodecyloxy]-dodecane;
1,12-bis-[12-(2'-O-9-(4-chlorophenyl)-9-bromofluorene)-dodecyloxy]-dodecane;
2-(3-octadecyloxy-2,2-bis-octadecyloxymethyl-propoxy)-9-(4-chlorophenyl)-9-fluorenol;
2-(3-octadecyloxy-2,2-bis-octadecyloxymethyl-propoxy)-9-(4-chlorophenyl)-9-bromofluorene;
9-(4-chlorophenyl)-2-(3,4,5-tris (octadecyloxy)-cyclohexylmethoxy)-9-fluorenol;
9-(4-chlorophenyl)-2-(3,4,5-tris (octadecyloxy)-cyclohexylmethoxy)-9-bromofluorene;
3,5-didocosyloxybenzyl alcohol;
2,4-didocosyloxybenzyl alcohol;
2,4-bis octadecyloxybenzyl alcohol;
3-didocosylaminobenzyl alcohol;
3-diphytylaminobenzyl alcohol;
N-(2',3'-dihydrophytyl)-N-(3-hydroxymethylphenyl) acetamide;
N-triacontyl-N-(3-hydroxymethylphenyl) acetamide;
3-(aminomethyl)-N,N-didocosylaniline;

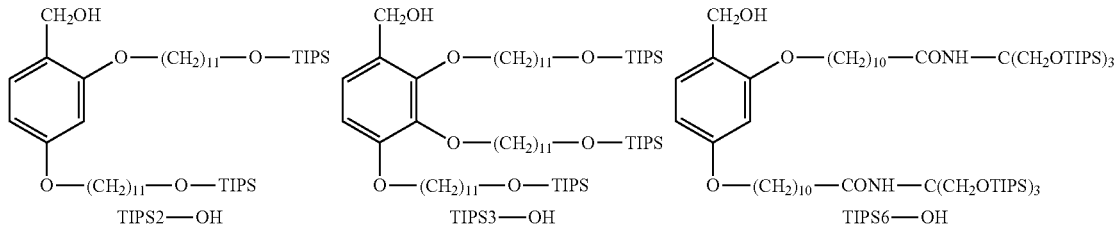

TIPS2—OH     TIPS3—OH     TIPS6—OH

-continued
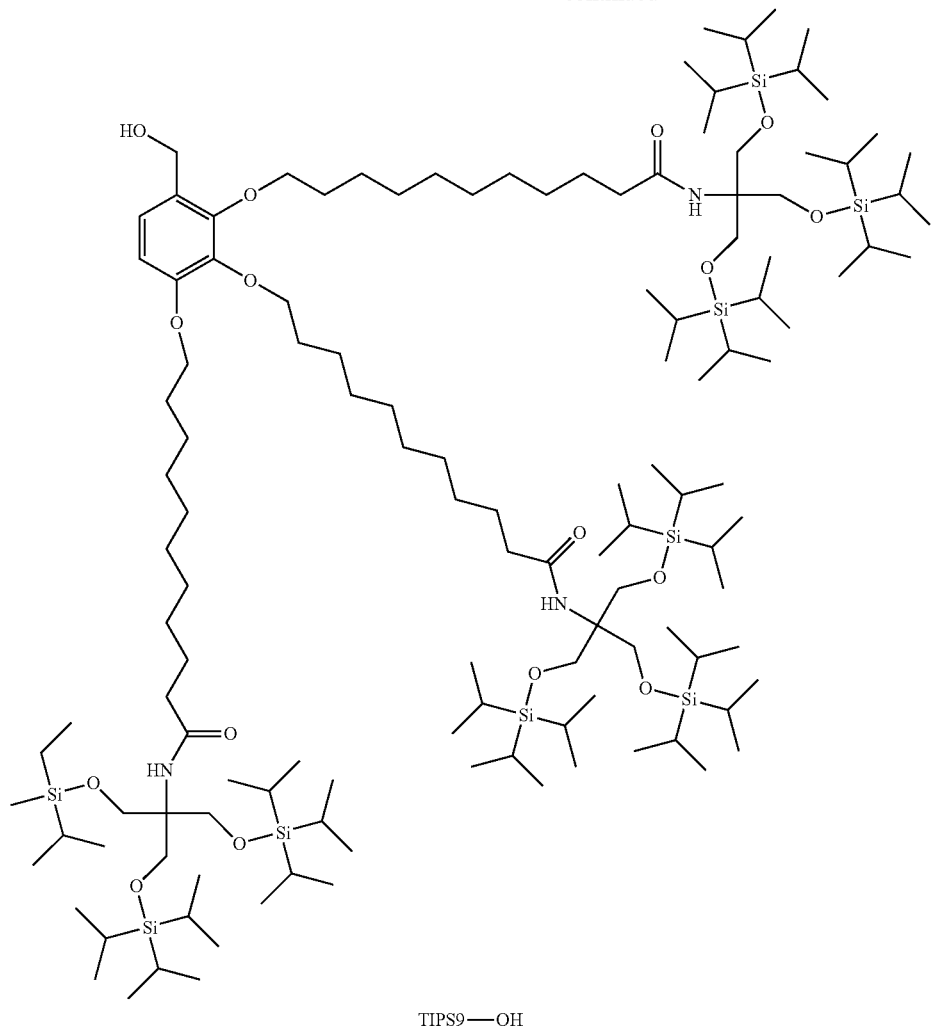
TIPS9—OH
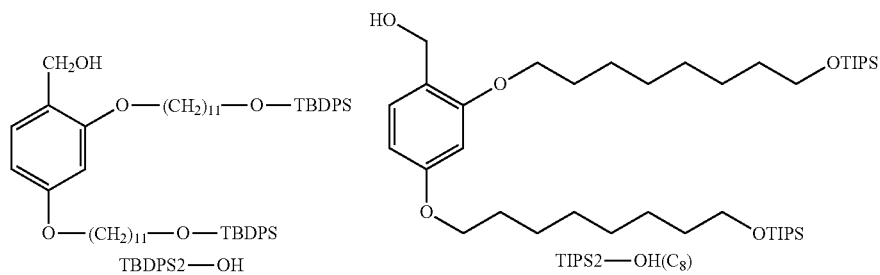
TBDPS2—OH
TIPS2—OH(C$_8$)
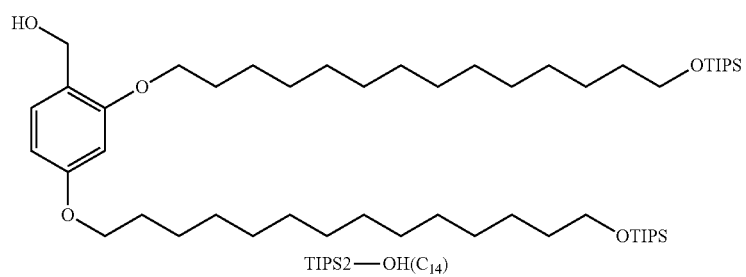
TIPS2—OH(C$_{14}$)

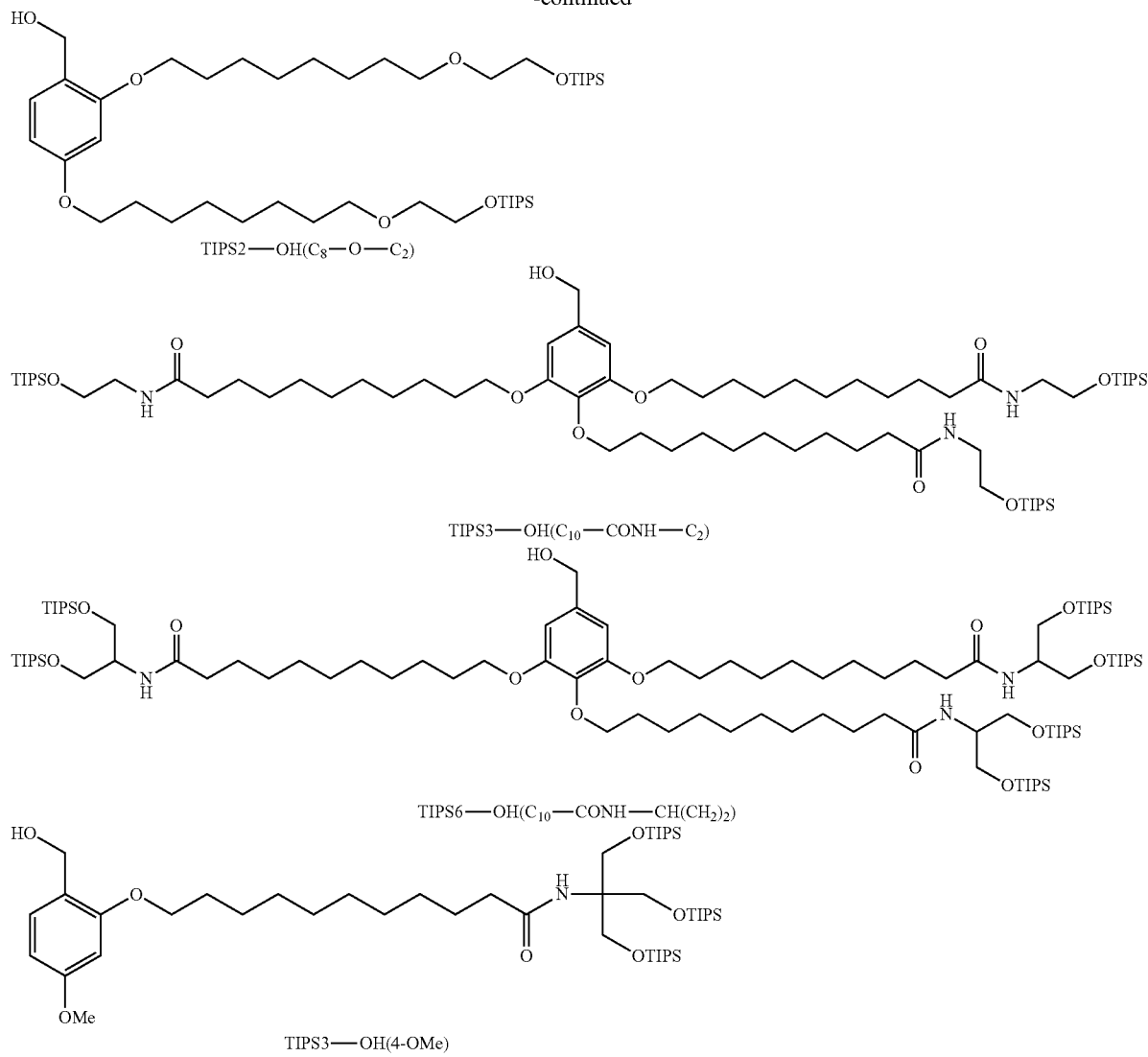

wherein TIPS is a triisopropylsilyl group, and TBDPS is a tert-butyldiphenylsilyl group.

15. A method for producing a peptide, comprising the following (A) or (B), or a combination thereof:
(A) washing a reaction mixture comprising an N-protected C-protected peptide having an amino acid residue number of from 5 to 100, in which an N-terminal amino group and C-terminal are protected by protecting groups, a side chain functional group is optionally further protected by a protecting group, and at least one of the C-terminal or the side chain functional group is protected by a pseudo-solid-phase protecting group in a flow reactor with water and/or a hydrophilic organic solvent in a continuous flow, and then purifying the N-protected C-protected peptide by partitioning in a continuous flow by an oil-water separation and separating an organic layer comprising the N-protected C-protected peptide, under a concentration condition being 5- to 100-fold dilution with respect to the N-protected C-protected peptide as a substrate;
(B) washing a reaction mixture comprising an N-unprotected C-protected peptide having an amino acid residue number of from 5 to 100, in which an N-terminal amino group is not protected, C-terminal is protected by a protecting group, a side chain functional group is optionally further protected by a protecting group, and at least one of the C-terminal or the side chain functional group is protected by a pseudo-solid-phase protecting group in a flow reactor with water and/or a hydrophilic organic solvent in a continuous flow, and then purifying the N-unprotected C-protected peptide by partitioning in a continuous flow by an oil-water separation and separating an organic layer comprising the N-unprotected C-protected peptide under the concentration condition being 2- to 100-fold dilution with respect to the N-unprotected C-protected peptide as a substrate;

wherein said method prior to the washing step in A or B, comprises producing a reaction mix comprising the peptide protected by a pseudo-solid-phase group by flow synthesis in a flow reactor;

wherein the pseudo-solid phase protecting group is at least one selected from the group consisting of:
(4',4'-bis (2,3-dihydrophytyloxy) phenyl) methylamine);
3,4,5-tri (2',3'-dihydrophytyloxy) benzyl alcohol;
2-[3,4,5-tri (2',3'-dihydrophytyloxy) benzyloxy]-4-methoxybenzyl alcohol;

3,4,5-tri (octadecyloxy) cyclohexanemethanol;
[bis-(4-docosoxy-phenyl)-methyl]-amine;
3,4,5-tri (octadecyloxy) benzyl alcohol;
4-methoxy-2-[3',4',5'-tris (octadecyloxy) benzyloxy) benzyl alcohol;
4-methoxy-2-[3',4',5'-tris (octadecyloxy) cyclohexylmethyloxy] benzyl alcohol;
2-docosyloxy-9-(4-chlorophenyl)-9-fluorenol;
2-docosyloxy-9-(4-chlorophenyl)-9-bromofluorene;
2,7-didocosyloxy-9-(4-chlorophenyl)-9-bromofluorene;
2-(12-docosyloxy-dodecanoxy)-9-(3-fluorophenyl)-9-bromofluorene;
1,12-bis-[12-(2'-O-9-(4-chlorophenyl)-9-fluorenol)-dodecyloxy]-dodecane;
1,12-bis-[12-(2'-O-9-(4-chlorophenyl)-9-bromofluorene)-dodecyloxy]-dodecane;
2-(3-octadecyloxy-2,2-bis-octadecyloxymethyl-propoxy)-9-(4-chlorophenyl)-9-fluorenol;
2-(3-octadecyloxy-2,2-bis-octadecyloxymethyl-propoxy)-9-(4-chlorophenyl)-9-bromofluorene;
9-(4-chlorophenyl)-2-(3,4,5-tris (octadecyloxy)-cyclohexylmethoxy)-9-fluorenol;
9-(4-chlorophenyl)-2-(3,4,5-tris (octadecyloxy)-cyclohexylmethoxy)-9-bromofluorene;
3,5-didocosyloxybenzyl alcohol;
2,4-didocosyloxybenzyl alcohol;
2,4-bis octadecyloxybenzyl alcohol;
3-didocosylaminobenzyl alcohol;
3-diphytylaminobenzyl alcohol;
N-(2',3'-dihydrophytyl)-N-(3-hydroxymethylphenyl) acetamide;
N-triacontyl-N-(3-hydroxymethylphenyl) acetamide;
3-(aminomethyl)-N,N-didocosylaniline;

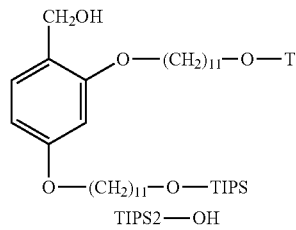
TIPS2—OH

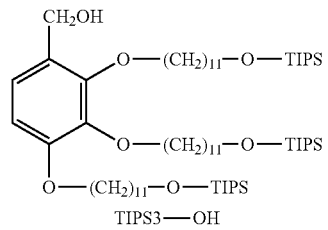
TIPS3—OH

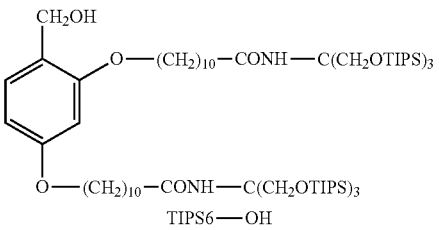
TIPS6—OH

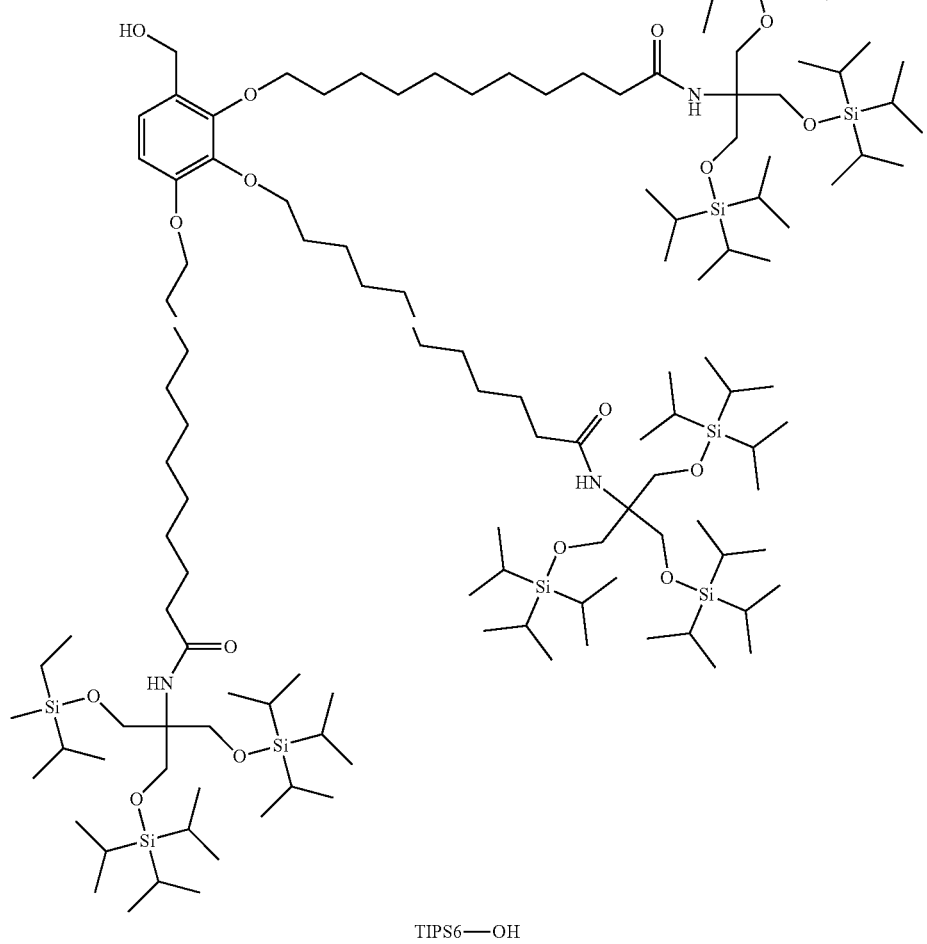
TIPS6—OH

-continued
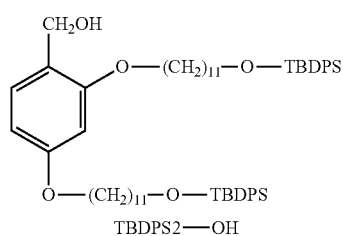
TBDPS2—OH
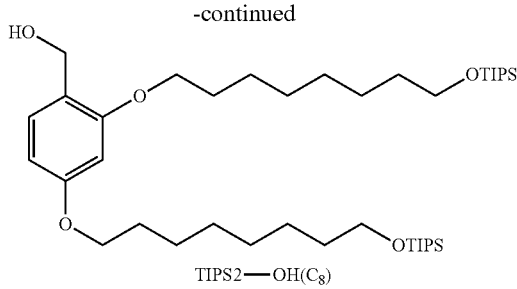
TIPS2—OH(C$_8$)
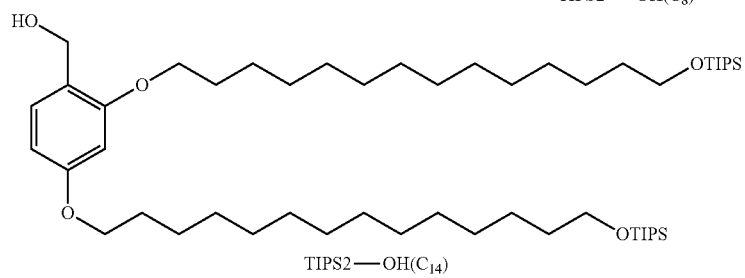
TIPS2—OH(C$_{14}$)
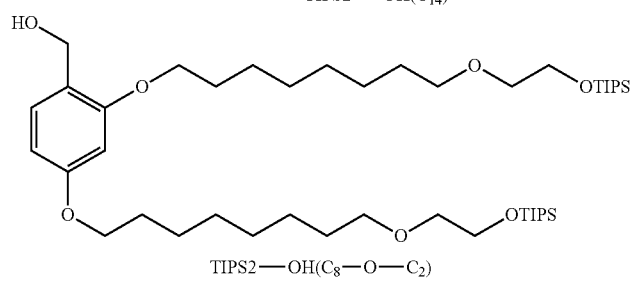
TIPS2—OH(C$_8$—O—C$_2$)
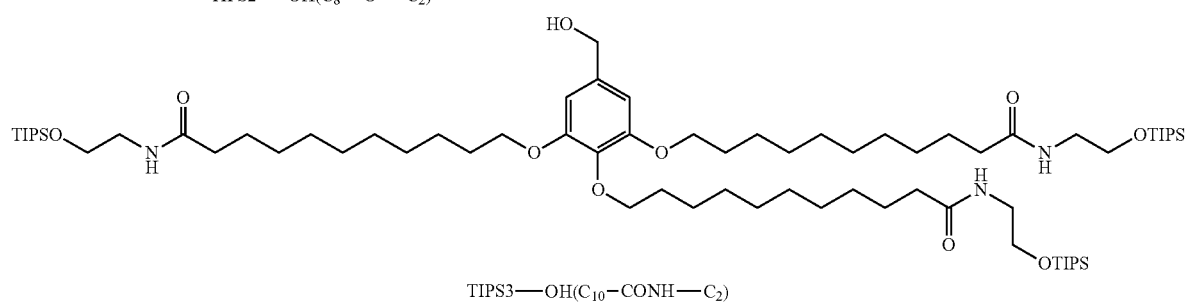
TIPS3—OH(C$_{10}$—CONH—C$_2$)
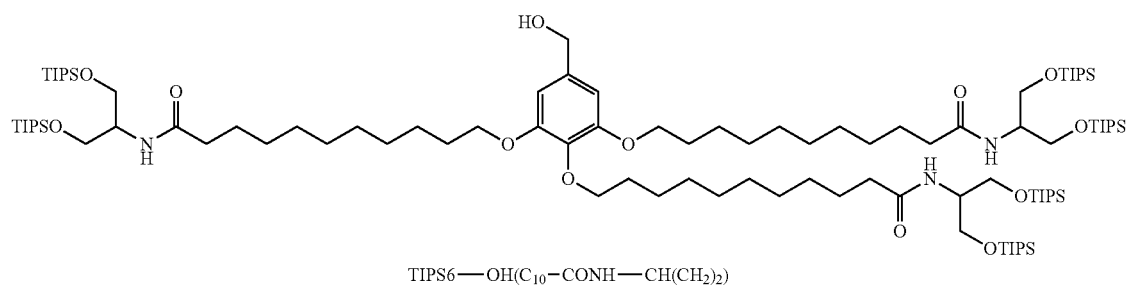
TIPS6—OH(C$_{10}$—CONH—CH(CH$_2$)$_2$) and
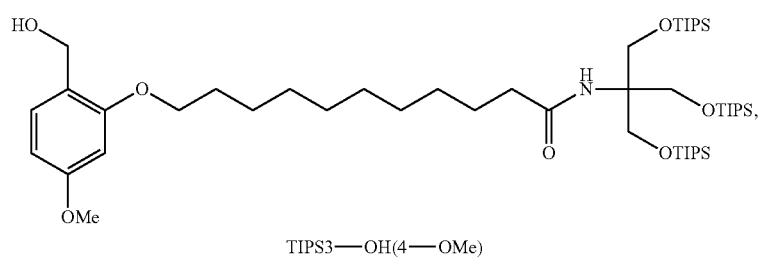
TIPS3—OH(4—OMe)

wherein TIPS is a triisopropylsilyl group, and TBDPS is a tert-butyldiphenylsilyl group.

\* \* \* \* \*